United States Patent [19]

Rempfler et al.

[11] Patent Number: 4,966,622
[45] Date of Patent: Oct. 30, 1990

[54] N-PHENYL-N-PYRIMIDIN-2-YLUREAS

[75] Inventors: Hermann Rempfler, Ettingen; Dieter Dürr, Bottmingen; Rudolf C. Thummel, Courgenay, all of Switzerland

[73] Assignee: Ciba-Geigy Corporation, Ardsley, N.Y.

[21] Appl. No.: 332,193

[22] Filed: Apr. 3, 1989

[30] Foreign Application Priority Data

Apr. 12, 1988 [CH] Switzerland ..................... 1336/88

[51] Int. Cl.$^5$ ..................... A01N 43/54; C07D 239/42
[52] U.S. Cl. ........................................... 71/92; 71/76; 71/86; 71/87; 71/90; 544/243; 544/321; 544/330; 544/331; 544/332
[58] Field of Search ............... 544/243, 321, 330, 331, 544/332; 71/86, 87, 90, 92

[56] References Cited

U.S. PATENT DOCUMENTS

| | | | |
|---|---|---|---|
| 4,659,363 | 4/1987 | Hubele et al. | 71/92 |
| 4,694,009 | 9/1987 | Hubele et al. | 514/269 |
| 4,783,459 | 11/1988 | Buhmann et al. | 514/235.8 |
| 4,802,909 | 2/1989 | Rempfler et al. | 71/92 |

FOREIGN PATENT DOCUMENTS 151404 of 1981 German Democratic Rep. .

OTHER PUBLICATIONS

Rempfler, et al., "Chemical Abstracts", vol. 109, 1988, col. 109;33864g.

*Primary Examiner*—Glennon H. Hollrah
*Assistant Examiner*—James H. Turnipseed
*Attorney, Agent, or Firm*—Kevin T. Mansfield; Edward McC. Roberts

[57] ABSTRACT

The present invention relates to novel N-phenyl-N-pyrimidin-2-ylureas having a herbicidal and plant growth-regulating activity, to agrochemical compositions containing those substances as active ingredients, to the use of the novel ureas for controlling weeds or for regulating plant growth, and to processes for the preparation of the novel compounds. The invention also relates to novel intermediates and to processes for the preparation thereof.

The novel compounds correspond to formula I

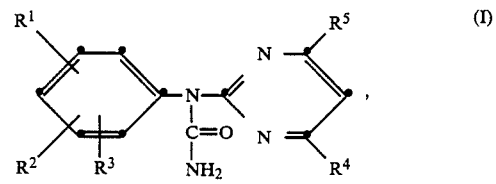

in which $R^1$, $R^2$ and $R^3$ are each, independently of the others, hydrogen; halogen; $C_1$–$C_4$alkyl; $C_1$–$C_4$alkoxy; $C_1$–$C_4$haloalkyl; $C_1$–$C_4$haloalkoxy; $C_1$–$C_4$alkyl-S(O)$_n$-; nitro; cyano; $C_1$–$C_4$alkoxycarbonyl; $C_1$–$C_4$alkylcarbonyl; di-($C_1$–$C_4$alkylamino)-carbonyl; mono-($C_1$–$C_4$alkylamino)carbonyl; carbamoyl; $C_1$–$C_4$haloalkyl-S(O)$_n$-; or -PO[O-($C_1$–$C_4$)-alkyl]$_2$;

$R^4$ is $C_1$–$C_6$alkyl; $C_1$–$C_4$alkoxy; $C_1$–$C_4$alkoxy-S(O)$_n$-; $C_1$–$C_4$haloalkyl; $C_1$–$C_4$haloalkoxy; phenyl that is unsubstituted or is substituted by up to three identical or different substituents from halogen, $C_1$–$C_4$alkyl, $C_1$–$C_4$haloalkyl and $C_1$–$C_4$alkoxy; 2-furanyl; 2-thienyl; 3-thienyl; $C_3$–$C_6$-cycloalkyl that is unsubstituted or is substituted by up to three identical or different $C_1$–$C_4$alkyl radicals; cyano; $C_2$–$C_4$haloalkenyl; $C_1$–$C_4$alkoxy-$C_1$–$C_4$alkyl; $C_1$–$C_4$alkoxy-$C_1$–$C_4$alkoxy; or halogen-$C_1$–$C_4$alkylthio;

$R^5$ is hydrogen; $C_1$–$C_3$alkyl; $C_1$–$C_3$haloalkyl; halogen; or $C_1$–$C_3$haloalkoxy; and n is 0, 1 or 2, with the proviso that when one of the radicals $R^1$, $R^2$ and $R^3$ is nitro, that substituent may not be bonded in the 2- or 6-position of the phenyl ring.

13 Claims, No Drawings

N-PHENYL-N-PYRIMIDIN-2-YLUREAS

The present invention relates to novel N-phenyl-N-pyrimidin-2-ylureas having a herbicidal and plant growth-regulating activity, to agrochemical compositions containing those substances as active ingredients, to the use of the novel ureas for controlling weeds or for regulating plant growth, and to processes for the preparation of the novel compounds. The invention also relates to novel intermediates and to processes for the preparation thereof.

(Pyrimidin-2-yl)-2-nitroanilines are known from Patent Specification DD-151 404 and from European Patent Application EP-A-0 172 786. These compounds are fungicidally active. In contrast, it has surprisingly been found that N-phenyl-N-pyrimidin-2-ylureas have a herbicidal and plant growth-regulating activity.

The invention relates to ureas of formula I

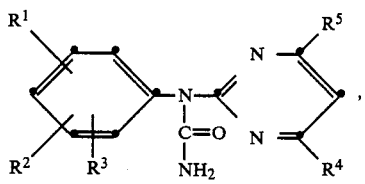

in which
$R^1$, $R^2$ and $R^3$ are each, independently of the others, hydrogen; halogen; $C_1$-$C_4$alkyl; $C_1$-$C_4$alkoxy; $C_1$-$C_4$haloalkyl; $C_1$-$C_4$haloalkoxy; $C_1$-$C_4$alkyl-S(O)$_n$-; nitro; cyano; $C_1$-$C_4$alkoxycarbonyl; di-($C_1$-$C_4$alkylamino)carbonyl; mono-($C_1$-$C_4$alkylamino)carbonyl; carbamoyl; $C_1$-$C_4$haloalkyl-S(O)$_n$-; $C_1$-$C_4$alkylcarbonyl; or -PO[O-($C_1$-$C_4$)-alkyl]$_2$;
$R^4$ is $C_1$-$C_6$alkyl; $C_1$-$C_4$alkoxy; $C_1$-$C_4$alkyl-S(O)$_n$-; $C_1$-$C_4$haloalkyl; $C_1$-$C_4$haloalkoxy; phenyl that is unsubstituted or is substituted by up to three identical or different substituents from halogen, $C_1$-$C_4$alkyl, $C_1$-$C_4$haloalkyl and $C_1$-$C_4$alkoxy; 2-furanyl; 2-thienyl; 3-thienyl; $C_3$-$C_6$-cycloalkyl that is unsubstituted or is substituted by up to three identical or different $C_1$-$C_4$alkyl radicals; cyano; $C_2$-$C_4$haloalkenyl; $C_1$-$C_4$alkoxy-$C_1$-$C_4$alkyl; $C_1$-$C_4$alkoxy-$C_1$-$C_4$alkoxy; or halo-$C_1$-$C_4$alkylthio;
$R^5$ is hydrogen; $C_1$-$C_3$alkyl; $C_1$-$C_3$haloalkyl; halogen; or $C_1$-$C_3$haloalkoxy; and
n is 0, 1 or 2,
with the proviso that when one of the radicals $R^1$, $R^2$ and $R^3$ is nitro, that substituent may not be bonded in the 2- or 6-position of the phenyl ring, and to salts and addition compounds of the compounds of formula I with acids, bases and complex formers.

Within the scope of the invention disclosed herein, the generic terms mentioned include, for example, the following specific individual substituents, without this list implying any limitation of the invention:

Alkyl includes straight-chained or branched $C_1$-$C_6$alkyl radicals, such as methyl, ethyl, n-propyl, isopropyl, n-butyl, sec.-butyl, tert.-butyl, isobutyl, the isomeric pentyl radicals, such as, for example, n-pentyl, tert.-pentyl (1,1-dimethylpropyl), isopentyl (1-ethylpropyl), and the isomeric hexyl radicals. $C_1$-$C_5$alkyl radicals are preferred.

Halogen is fluorine, chlorine, bromine or iodine. Fluorine, chlorine and bromine are preferred.

Haloalkyl indicates alkyl radicals, according to the respective scope of definition given, that are completely or partially substituted by identical or different halogen atoms, such as, for example, trifluoromethyl, difluoromethyl, 1,1,2,2-tetrafluoroethyl, 2-chloroethyl, pentafluoroethyl, chlorodifluoromethyl, dichloromethyl, chlorofluoromethyl, 1,1-dichloro-2,2,2-trifluoroethyl, 1,1-dichloroethyl or heptafluoropropyl.

There may be mentioned as $C_1$-$C_4$alkoxycarbonyl radicals, inter alia, methoxycarbonyl, ethoxycarbonyl and the isomeric propoxycarbonyls and butoxycarbonyls.

Alkoxy within the scope of the respective definition of the isomeric alkoxy radicals is especially methoxy, ethoxy, (i)-propoxy, (n)-propoxy, (i)-butoxy, (t)-butoxy, (n)-butoxy and (sec.)-butoxy.

Haloalkoxy and haloalkylthio within the scope of the respective definition are isomeric alkyl radicals that are mono- or poly-substituted by identical or different halogen atoms, such as, for example, trifluoromethoxy, 2,2,2-trifluoroethoxy, trifluoromethylthio, 2,2,3,3,3-pentafluoropropoxy or 1,1,2,2-tetrafluoroethoxy, difluoromethoxy or 2-chloroethoxy.

There may be mentioned as alkoxyalkyl radicals, inter alia: 2-ethoxyethyl, 2-methoxyethyl, 3-methoxypropyl, 2-methoxy-1-methylethyl and methoxymethyl.

The group $C_1$-$C_4$alkyl-S(O)$_n$- represents the respective alkylthio, alkylsulfinyl and alkylsulfonyl radicals. Methylthio, methylsulfinyl and methylsulfonyl may be mentioned as being especially preferred.

Of the groups PO[O($C_1$-$C_4$)-alkyl]$_2$, PO(OCH$_3$)$_2$ are preferred.

Di-($C_1$-$C_4$alkylamino)carbonyl includes radicals substituted either by identical or different $C_1$-$C_4$alkyl radicals.

Haloalkylthio is especially fluoromethylthio, difluoromethylthio, trifluoromethylthio, 1,1,2,2-tetrafluoroethylthio, chlorodifluoromethylthio and dichlorofluoromethylthio.

In the further substituents that are composed of several base elements, the sub-elements may be freely selected with the scope of the definition and have the above meaning.

Attention is drawn to compounds of formula I unsubstituted in the 4-position of the phenyl ring

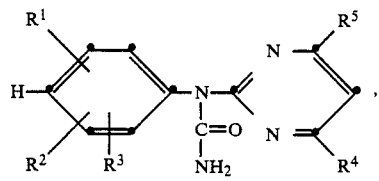

in which
$R^1$ is halogen; cyano; $C_1$-$C_4$alkoxy; $C_1$-$C_4$haloalkoxy; $C_1$-$C_4$alkyl-S(O)$_n$-; $C_1$-$C_4$alkyl; $C_1$-$C_4$haloalkyl; $C_1$-$C_4$alkoxycarbonyl; di-($C_1$-$C_4$alkylamino)carbonyl; mono-($C_1$-$C_4$alkylamino)carbonyl; carbamoyl; $C_1$-$C_4$haloalkyl-S(O)$_n$-; or -PO[O-($C_1$-$C_4$)alkyl]$_2$;
$R^2$ is hydrogen; halogen; cyano; nitro; $C_1$-$C_4$alkyl; $C_1$-$C_4$alkoxy; $C_1$-$C_4$-haloalkyl; $C_1$-$C_4$alkoxycarbonyl; or $C_1$-$C_4$alkylcarbonyl;
$R^3$ is hydrogen; halogen; or $C_1$-$C_4$alkyl, and n and the radicals $R^4$ and $R^5$ are as defined hereinbefore.

Preferred sub-groups are formed by those compounds of formula I in which
(a) the radical $R^1$ is bonded at the 2-position of the phenyl ring,
(b) the radical $R^2$ is bonded at the 3-position of the phenyl ring,
(c) the radical $R^3$ is bonded at the 5-position of the phenyl ring,
(d) the radical $R^2$ is bonded at the 6-position of the phenyl ring,
(e) the radical $R^1$ is bonded at the 3-position of the phenyl ring,
(f) the radical $R^3$ is bonded at the 3-position of the phenyl ring,
(g) the radical $R^2$ is bonded at the 5-position of the phenyl ring.

Attention is drawn to the following combinations of sub-groups: a+b, a+g, a+d, e+g, e+d, a+b+c, a+f+d, a+c+d and e+c+d, the radical $R^3$ being hydrogen in combinations of only two sub-groups.

Attention is drawn especially to compounds of formula I in which
$R^1$ is halogen; cyano; $C_1$–$C_3$alkoxy; $C_1$–$C_2$haloalkoxy; methyl-$S(O)_n$-; $C_1$–$C_3$alkyl; $C_1$–$C_2$haloalkyl; $C_1$–$C_4$alkoxycarbonyl; carbamoyl; difluoromethylthio or -PO[O-($C_1$–$C_2$)-alkyl]$_2$;
$R^2$ is hydrogen; fluorine; chlorine; bromine; cyano; nitro; $C_1$–$C_3$alkyl; $C_1$–$C_2$haloalkyl; or $C_1$–$C_3$alkoxycarbonyl;
$R^3$ is hydrogen; chlorine; fluorine; or $C_1$–$C_3$alkyl;
$R^4$ is $C_1$–$C_5$alkyl; $C_1$–$C_4$alkoxy, $C_1$–$C_4$alkylthio; cyclopropyl; phenyl; furan-2-yl; thiophen-2-yl; cyano; $C_1$–$C_3$haloalkoxy; $C_1$–$C_2$alkoxy-$C_1$–$C_2$alkyl; $C_1$–$C_2$alkoxy-$C_1$–$C_2$alkoxy; methylsulfinyl; methylsulfonyl; or $C_2$–$C_3$haloalkenyl;
$R^5$ is $C_1$–$C_3$alkyl; fluorine; chlorine; bromine; $C_1$–$C_3$haloalkyl; or $C_1$–$C_3$haloalkoxy; and
n is 0, 1 or 2.

Especially preferred are compounds of formula I in which
$R^1$ is halogen; methyl; trifluoromethyl; trifluoromethoxy; difluoromethoxy; $C_1$–$C_3$alkoxy; methylthio; methylsulfinyl; methylsulfonyl; cyano; $C_1$–$C_4$alkoxycarbonyl; carbamoyl; difluoromethylthio; or -PO(O-$C_2H_5$)$_2$;
$R^2$ is hydrogen; fluorine; chlorine; bromine; nitro; ethyl; methyl; trifluoromethyl; methoxy; or $C_1$–$C_3$alkoxycarbonyl;
$R^3$ is hydrogen; chlorine; or methyl;
$R^4$ is $C_1$–$C_5$alkyl; $C_1$–$C_4$alkoxy; $C_1$–$C_4$alkylthio; cyclopropyl; phenyl; furan-2-yl; thiophen-2-yl; cyano; 1,1,2,2-tetrafluoroethoxy; 2-chloroethoxy; methoxymethyl; 2-methoxy-ethoxy; methylsulfinyl; methylsulfonyl; or 2,2-dichlorovinyl;
$R^5$ is $C_1$–$C_3$alkyl; fluorine; chlorine, bromine; difluoromethoxy; trifluoromethyl; pentafluoroethyl; chlorodifluoromethyl; difluoromethyl; dichloromethyl; chlorofluoromethyl; 1,1-dichloro-2,2,2-trifluoroethyl; 1,1-dichloroethyl; or heptafluoropropyl.

The invention relates especially to compounds of formula I in which
$R^1$ is fluorine; chlorine; bromine; iodine; trifluoromethyl; methyl; difluoromethoxy; methoxy; methylthio; PO(O$C_2H_5$)$_2$; methoxycarbonyl; methylsulfonyl; or cyano;
$R^2$ is hydrogen; fluorine; chlorine; bromine; nitro; methyl; ethyl; trifluoromethyl; or methoxycarbonyl;
$R^3$ is hydrogen; or methyl;
$R^4$ is $C_1$–$C_5$alkyl; butylthio; thiophen-2-yl; furan-2-yl; $C_1$–$C_4$alkoxy; methylthio; methylsulfinyl; methylsulfonyl; or cyclopropyl; and
$R^5$ is methyl; chlorine; dichloromethyl; pentafluoroethyl; difluoromethyl; chlorofluoromethyl; trifluoromethyl; or chlorodifluoromethyl.

Attention is drawn furthermore to compounds of formula I in which
(a) $R^1$ is fluorine, chlorine, bromine, trifluoromethyl, cyano, difluoromethoxy, trifluoromethoxy, methyl or methoxy, each bonded in the 2-position of the phenyl ring,
$R^2$ and $R^3$ are each hydrogen,
$R^4$ is methyl, furan-2-yl or cyclopropyl, and
$R^5$ is chlorine, methyl, trifluoromethyl or chlorodifluoromethyl, or
(b) $R^1$ is fluorine, chlorine, bromine, trifluoromethyl, difluoromethoxy, trifluoromethoxy, cyano or methoxy, each bonded in the 2-position of the phenyl ring,
$R^2$ is fluorine or chlorine, each bonded in the 3-, 5- or 6-position of the phenyl ring,
$R^4$ is methyl, furan-2-yl or cyclopropyl, and
$R^5$ is chlorine, methyl, trifluoromethyl or chlorodifluoromethyl, or
(c) $R^1$ is chlorine bonded in the 3-position of the phenyl ring,
$R^2$ is chlorine bonded in the 5-position of the phenyl ring,
$R^4$ is methyl, furan-2-yl or cyclopropyl, and
$R^5$ is chlorine, methyl, trifluoromethyl or chlorodifluoromethyl.

The following compounds may be mentioned specifically on account of their herbicidal activity:
N-(2-bromophenyl)-N-(4-chloro-6-methyl-pyrimidin-2-yl)-urea,
N-(4-methyl-6-trifluoromethyl-pyrimidin-2-yl)-N-(2-trifluoromethylphenyl)-urea,
N-(2,3-dichlorophenyl)-N-(4-methyl-6-trifluoromethyl-pyrimidin-2-yl)-urea,
N-(2,5-dichlorophenyl)-N-(4,6-dimethyl-pyrimidin-2-yl)-urea,
N-(4-chloro-6-methyl-pyrimidin-2-yl)-N-(2,5-dichlorophenyl)-urea,
N-(2,5-dichlorophenyl)-N-(4-methyl-6-trifluoromethyl-pyrimidin-2-yl)-urea,
N-[4-(chlorodifluoromethyl)-6-methyl-pyrimidin-2-yl]-N-(2,5-dichlorophenyl)-urea,
N-(4-chloro-6-methyl-pyrimidin-2-yl)-N-(2,6-dichlorophenyl)-urea,
N-(2,6-dichlorophenyl)-N-(4-methyl-6-trifluoromethyl-pyrimidin-2-yl)-urea,
N-(4-cyclopropyl-6-trifluoromethyl-pyrimidin-2-yl)-N-(2,6-dichlorophenyl)-urea,
N-(3,5-dichlorophenyl)-N-(4-methyl-6-trifluoromethyl-pyrimidin-2-yl)-urea,
N-(5-chloro-2-methyl-phenyl)-N-(4-chloro-6-methyl-pyrimidin-2-yl)-urea,
N-(5-chloro-2-methoxyphenyl)-N-(4-methyl-6-trifluoromethyl-pyrimidin-2-yl)-urea,
N-(2-iodophenyl)-N-(4-methyl-6-trifluoromethyl-pyrimidin-2-yl)-urea,
N-(2-chloro-6-methylphenyl)-N-(4-chloro-6-methyl-pyrimidin-2-yl)-urea,
N-(3-chloro-2-methoxyphenyl)-N-(4-methyl-6-trifluoromethylpyridin-2-yl)-urea,
N-(2,6-difluorophenyl)-N-(4-methyl-6-trifluoromethylpyridin-2-yl)-urea, N-(2,5-difluorophenyl)-N-(4-methyl-6-trifluoromethyl-pyrimidin-2-yl)-urea,
N-(2-cyanophenyl)-N-(4-methyl-6-trifluoromethyl-pyrimidin-2-yl)-urea
N-(2-bromophenyl)-N-(4-cyclopropyl-6-trifluoromethyl-pyrimidin-2-yl)-urea,
N-(4-isopropyl-6-trifluoromethyl-pyrimidin-2-yl)-N-2-(trifluoromethylphenyl)-urea,
N-(2-fluorophenyl)-N-(4-methyl-6-trifluoromethyl-pyrimidin-2-yl)-urea,
N-(2-fluorophenyl)-N-(4-isopropyl-6-trifluoromethyl-pyrimidin-2-yl)-urea,
N-(2,5-dichlorophenyl)-N-(4-ethyl-6-trifluoromethyl-pyrimidin-2-yl)-urea,
N-(2,6-dichlorophenyl)-N-(4-difluoromethyl-6-methyl-pyrimidin-2-yl)-urea,
N-(2,6-dichlorophenyl)-N-(4-methylthio-6-trifluoromethyl-pyrimidin-2-yl)-urea,
N-(2,6-dichloro-3-methyl)-N-(4-methyl-6-trifluoromethyl-pyrimidin-2-yl)-urea,
N-(2,6-dichloro-3-methylphenyl)-N-(4-isopropyl-6-trifluoromethylpyrimidin-2-yl)-urea,
N-(2-chloro-6-trifluoromethyl-phenyl)-N-(4-methyl-6-trifluoromethylpyrimidin-2-yl)-urea,
N-(2-chloro-6-methyl-phenyl)-N-(4-methyl-6-trifluoromethyl-pyrimidin-2-yl)-urea,
N-(2-methyl-6-trifluoromethyl-phenyl)-N-(4-methyl-6-trifluoromethylpyrimidin-2-yl)-urea,
N-(5-chloro-2-difluoromethoxy-phenyl)-N-(4-methyl-6-trifluoromethylpyrimidin-2-yl)-urea,
N-(2-methylthio-phenyl)-N-(4-methyl-6-trifluoromethyl-pyrimidin-2-yl)-urea,
N-(4-cyclopropyl-6-trifluoromethyl-pyrimidin-2-yl)-N-(2,5-difluorophenyl)-urea,
N-(2,6-difluorophenyl)-N-(4-ethyl-6-trifluoromethyl-pyrimidin-2-yl)-urea,
N-(6-chloro-2-fluoro-phenyl)-N-(4-methyl-6-trifluoromethyl-pyrimidin-2-yl)urea,
N-(6-chloro-2-fluoro-phenyl)-N-(4-cyclopropyl-6-trifluoromethyl-pyrimidin2-yl)-urea,
N-(2-difluoromethoxyphenyl)-N-(4-methyl-6-trifluoromethyl-pyrimidin-2-yl)urea,
N-(6-chloro-2-methoxycarbonyl-phenyl)-N-(4-methyl-6-trifluoromethylpyrimidin-2-yl)-urea,
N-(2-bromophenyl)-N-[4-(furan-2-yl)-6-trifluoromethyl-pyrimidin-2-yl]-urea,
N-(2-chloro-6-methyl-phenyl)-N-(4-methoxymethyl-6-trifluoromethylpyrimidin-2-yl)-urea and
N-(2-difluoromethoxy-6-methyl-phenyl)-N-(4-methyl-6-trifluoromethylpyrimidin-2-yl)-urea.

The compounds of formula I can be prepared by (a) reacting an aniline of formula II with phosgene to form a carbamoyl chloride of formula III and reacting this with NH3 in a second step

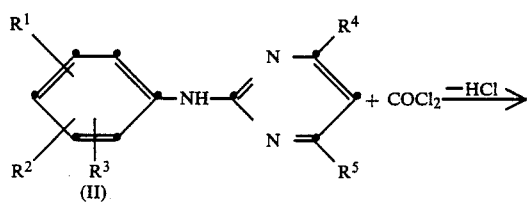

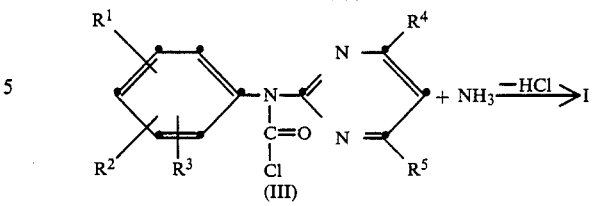

to form a urea of formula I, or (b) reacting an aniline of formula II with a halosulfonyl isocyanate IX to form a halosulfonylurea of formula IV

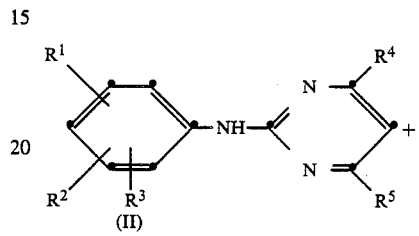

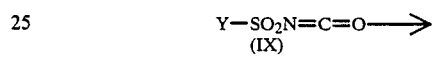

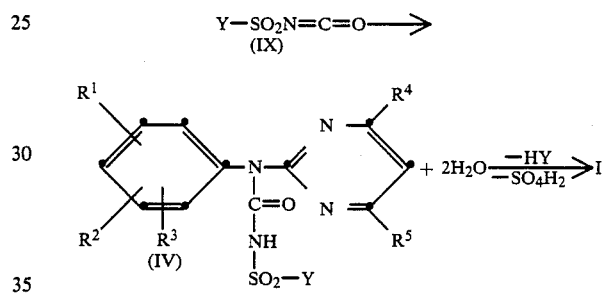

and hydrolysing this in a second step, or directly, to a compound of formula I, Y being a group that can be removed under the reaction conditions, such as halogen, preferably chlorine.

The reactions II→III, III→I and IV→I, which proceed with the removal of hydrogen halide or the elimination of HY, are preferably carried out using acid-binding agents (bases).

Suitable acid-binding agents are organic or inorganic bases, for example tertiary amines, such as trialkylamines (trimethylamine, triethylamine, tripropylamine etc.), pyridines (pyridine, 4-dimethylaminopyridine, 4-pyrrolidylaminopyridine etc.), and alcoholates, such as, for example, potassium-tert.-butoxide, sodium methoxide or sodium ethoxide. The afore-mentioned reactions, including also the reaction VII→II (which will be described hereinafter), can also be carried out with bases under phase transfer conditions according to processes that are known per se. (Lit. Dehmlow & Dehmlow, Phase Transfer Catalysis Verlag Chemie, Weinheim, 1983).

It is possible, in principle, for one or more solvents or diluents that are inert towards the reaction to be present in process variants (a) and (b), should there be no specific details given. Suitable solvents or diluents are, for example, aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butylmethyl ether etc.), anisole, dioxan, tetrahydrofuran; nitriles, such as acetonitrile, propionitrile; N,N-dialkylated amides, such as dimethylformamide; dimethyl sulfoxide; ketones, such as acetone, diethyl ketone, methyl ethyl ketone; and mixtures of such solvents with each other.

The anilines of formula II, like the carbamoyl chlorides of formula III and the ureas of formula IV, are valuable intermediates. The carbamoyl chlorides III and the ureas IV are novel, whereas some of the compounds of formula II are already known from DD-B-151 404.

The invention accordingly relates also to the novel compounds of formula II

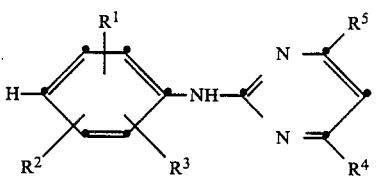

in which
$R^1$ is halogen; cyano; $C_1$-$C_4$alkoxy; $C_1$-$C_4$haloalkoxy; $C_1$-$C_4$alkyl-S(O)$_n$-; $C_1$-$C_4$alkyl; $C_1$-$C_4$haloalkyl; $C_1$-$C_4$-alkoxycarbonyl; di-($C_1$-$C_4$alkylamino)carbonyl; mono-($C_1$-$C_4$alkylamino)carbonyl; carbamoyl; $C_1$-$C_4$haloalkyl-S(O)-; or -PO[O-($C_1$-$C_4$)-alkyl]$_2$;
$R^2$ is hydrogen; halogen; cyano; nitro; $C_1$-$C_4$alkyl; $C_1$-$C_4$alkoxy; $C_1$-$C_4$haloalkyl; $C_1$-$C_4$alkoxycarbonyl; or $C_1$-$C_4$alkylcarbonyl;
$R^3$ is hydrogen; halogen; or $C_1$-$C_4$alkyl;
$R^4$ is $C_1$-$C_6$alkyl; $C_1$-$C_4$alkoxy; $C_1$-$C_4$alkyl-S(O)$_n$-; $C_1$-$C_4$haloalkyl; $C_1$-$C_4$haloalkoxy; phenyl that is unsubstituted or is substituted by up to three identical or different substituents from halogen, $C_1$-$C_4$alkyl, $C_1$-$C_4$haloalkyl and $C_1$-$C_4$alkoxy; 2-furanyl; 2-thienyl; 3-thienyl; $C_3$-$C_6$cycloalkyl that is unsubstituted or is substituted by up to three identical or different $C_1$-$C_4$alkyl radicals; cyano; $C_2$-$C_4$haloalkenyl; $C_1$-$C_4$alkoxy-$C_1$-$C_4$alkyl; $C_1$-$C_4$alkoxy-$C_1$-$C_4$alkoxy; or halo-$C_1$-$C_4$alkylthio;
$R^5$ is hydrogen; $C_1$-$C_3$alkyl; $C_1$-$C_3$haloalkyl; halogen; or $C_1$-$C_3$haloalkoxy; and
n is 0, 1 or 2,
with the proviso that (a) when one of the radicals $R^2$ and $R^3$ is nitro, that substituent may not be bonded in the 2- or 6-position of the phenyl ring and, when the radicals $R^4$ and $R^5$ are methyl, $R^1$ is not chlorine, methoxy, ethoxy, fluorine, iodine, methyl or bromine and that, furthermore, the following individual compounds are not included: N-[(4,6-bis-trifluoromethyl)-pyrimidin-2-yl]-2,6-dichloroaniline and N-(4-chloro-6-methyl-pyrimidin-2-yl)-3-chloroaniline.

The invention also relates to novel N,N-disubstituted carbamoyl chlorides of formula III

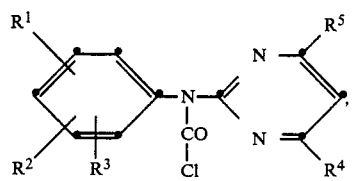

in which the radicals $R^1$ to $R^5$ are as defined for formula I, and to novel ureas of formula IV

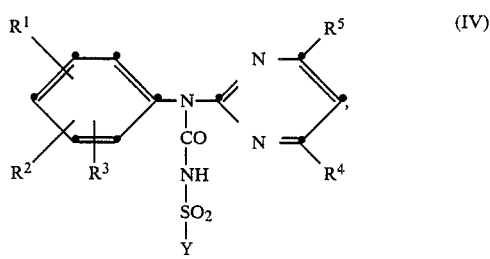

in which the radicals $R^1$ to $R^5$ are as defined for formula I, and Y is halogen, $C_1$-$C_4$alkoxy or phenoxy.

The compounds of formulae III and IV are intermediates of processes (a) and (b) and can be prepared, as described, from the corresponding anilines of formula II.

The novel anilines of formula II can be prepared analogously to processes known from the literature, for example by (aa) reacting guanidines of formula V with 1,3-dicarbonyl compounds of formula VI

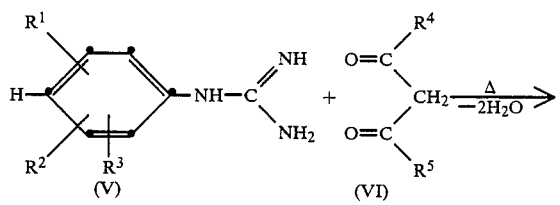

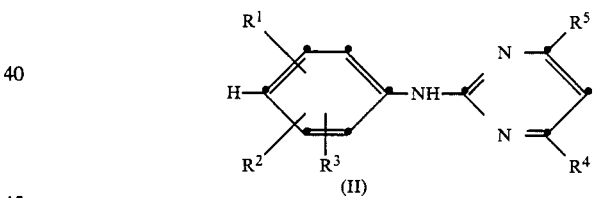

the condensation reaction if desired being carried out in the presence of water-binding agents (Lit.: D. J. Brown in "The Chemistry of Heterocyclic Compounds" Vol. VI 1962, Interscience Publ. New York; J. Am. Chem. Soc. 69 1819 (1947); J. Am. Chem. Soc. 72 2948 (1950); J. Org. Chem. 29 1439 (1964) or J. Org. Chem. 29 1883 (1964), Houben-Weyl "Methoden d. org. Chemie" Vol. VIII p. 180 ff), or (bb) reacting an aniline of formula VII with a pyrimidine of formula VIII under the action of a base,

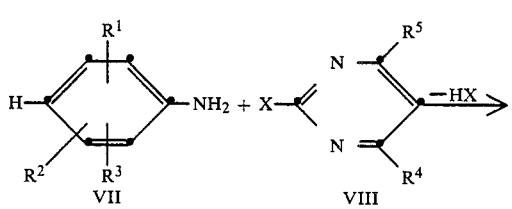

-continued

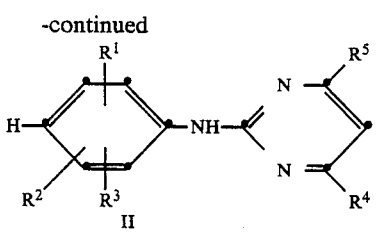

II in which formulae the radicals $R^1$ to $R^5$ are as defined hereinbefore and X is a nucleofugal group, such as halogen, $C_1$-$C_4$alkylsulfonyl or phenylsulfonyl.

Suitable bases for carrying out this process are, inter alia, potassium tert.-butoxide, $Na_2CO_3$, $K_2CO_3$ or NaH.

These processes are generally available for the synthesis of compounds of formula II and are applicable to all educts of formulae V, VI, VII and VIII (in which the radicals $R^1$ to $R^5$ are as defined within the scope of the formula of compounds I).

The invention furthermore relates to herbicidal and plant growth-regulating compositions containing a compound of formula I together with suitable adjuvants and/or carriers.

The active ingredients of the formula I are in general used successfully at application rates of from 0.005 to 5 kg/ha, especially from 0.1 to 3 kg/ha. The dosage necessary to achieve the desired effect can be ascertained by tests. It is dependent upon the nature of the action, the stage of development of the crop plants and of the weed and on the application (locus, time, method), and may vary within wide ranges, subject to these parameters.

At lower rates of application the compounds of formula I are distinguished by growth-inhibiting and herbicidal properties, which make them excellent for use in crops of useful plants, especially cereals, cotton, soybeans, sunflowers, rape, maize and rice.

The compounds of formula I also have plant growth-regulating properties. The growth of both monocotyledons and dicotyledons is affected. Inhibition of the vegetative growth makes it possible with many crop plants for the crop to be more densely planted, so that it is possible to achieve a higher yield per unit area of soil. Another mechanism of the increase in yield when using growth regulators is based on the fact that the nutrients are used to the greater advantage of the formation of the flowers and fruit whilst the vegetative growth is restricted. At higher rates of application, weeds and grasses are damaged in their development to such an extent that they die.

In an especially advantageous manner, the growth-regulating compounds of formula I can be used for regulating the growth of intersown plants in maize crops.

Plants that are suitable in principle for intersowing in maize crops are those that cover the soil between the individual maize plants and thus, especially, counteract soil erosion in maize crops. Suitable plants for intersowing are, inter alia, rape, trefoil, grasses or leguminosae.

At suitable rates of application, the compounds of formula I inhibit the new growth of grasses. This makes it possible to reduce the number of cuts necessary, or to increase the intervals between cutting, in grassed areas (parks, gardens, etc.). In an especially advantageous manner, it is possible to use granulate formulations of the active ingredients of formula I for this purpose. Either the granulate may contain the active ingredient on its own together with the customary adjuvants and carriers, or the active ingredient is formulated as a granulate together with a mineral fertiliser and/or, if desired, other active ingredients for controlling moss or other plant growth that is undesirable in grassed areas. Application in the form of a strewing granulate (for direct soil application) makes it possible, using equipment customary for maintaining grassed areas, to inhibit the new growth of grasses for a relatively long period. The granulate can be prepared in a manner known per se, and it preferably has a granule size of 0.1 to 2.0 mm, especially 0.25 to 1.0 mm.

The invention relates also to herbicidal and plant growth-regulating compositions that contain an active ingredient of formula I, and to methods of controlling weeds pre-emergence and post-emergence and of influencing the growth of monocotyledonous and dicotyledonous plants, especially grasses, tropical cover crops and suckers.

The compounds of formula I are used in unmodified form or, preferably, in the form of compositions together with the adjuvants conventionally employed in the art of formulation, and are therefore advantageously formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. The active substances of formula I can thus also be applied to mineral fertilisers (dressing). The composition so obtainable is advantageously suitable as a growth regulator for grasses.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Agglutinants are especially those adjuvants that in the case of granulation cause the carrier material, the adjuvants and the active ingredients to stick together, such as gum arabic or carboxymethylcellulose.

Surfactants customary in the art of formulation are described, inter alia, in the following publications:

"1987 International McCutcheon's Emulsifiers and Detergents", Glen Rock, N.J., USA.

Dr. Helmut Stache "Tensid Taschenbuch"

Carl Hanser Varlag, Munich/Vienna 1981.

The preparations usually contain 0.1 to 95%, preferably 0.1 to 80%, of a compound of formula I, 1 to 99% of a solid or liquid adjuvant, and 0 to 25%, preferably 0.1 to 25%, of a surfactant.

Preferred formulations are composed especially as follows (%=percent by weight).

| Emulsifiable concentrates: | |
|---|---|
| a compound of formula I: | 1 to 20%, preferably 5 to 10% |
| surfactant: | 5 to 30%, preferably 10 to 20% |
| liquid carrier: | 50 to 94%, preferably 70 to 85%. |
| Dusts: | |
| a compound of formula I: | 0.1 to 10%, preferably 0.1 to 1% |
| solid carrier: | 99.9 to 90%, preferably 99.9 to 99%. |
| Suspension concentrates: | |
| a compound of formula I: | 5 to 75%, preferably 10 to 50% |
| water: | 94 to 25%, preferably 90 to 30% |
| surfactant: | 1 to 40%, preferably 2 to 30%. |
| Wettable powders: | |
| a compound of formula I: | 0.5 to 90%, preferably 1 to 80% |
| surfactant: | 0.5 to 20%, preferably 1 to 15% |
| solid carrier: | 5 to 95%, preferably 15 to 90%. |
| Granulates: | |
| a compound of formula I: | 0.5 to 30%, preferably 3 to 15% |
| solid carrier: | 99.5 to 70%, preferably 97 to 85%. |
| Strewing granulate: | |
| a compound of formula I: | 0.01 to 30%, preferably 0.05 to 15% |
| agglutinant: | 0.05 to 5%, preferably 0.1 to 2% |
| surfactant: | 0.5 to 20%, preferably 1 to 15% |
| solid carrier: | 99.44 to 45%, preferably 95 to 65% |

Whereas commercial products will preferably be formulated as concentrates, the end user will normally employ dilute formulations. The formulations can be diluted to a concentration of as low as 0.001% active ingredient. The rates of application are normally from 0.005 to 5 kg active ingredient/ha.

The compositions may also contain further additives such as stabilisers, antifoams, viscosity regulators, binders, tackifiers and also fertilisers, or other active ingredients for obtaining special effects.

PREPARATION EXAMPLES

The (uncorrected) melting points in the following Preparation Examples are in °C.

P. 1. Compounds of formula I

P. 1.1
N-(4-methyl-6-trifluoromethyl-pyrimidin-2-yl)-N-(2-trifluoromethylphenyl)-urea At 3° C., 3.6 g (0.026 mole) of chlorosulfonyl isocyanate are added to a solution of 6.4 g (0.02 mole) of N-(4-methyl-6-trifluoromethyl-pyrimidin-2-yl)-2-trifluoromethylaniline in 100 ml of ethyl acetate. After stirring the batch for 2 hours at 3° C., 100 ml of ethyl acetate and 50 ml of ice-water are added. The aqueous phase is separated off, and the organic phase is washed with sodium chloride solution, dried with sodium sulfate and concentrated by evaporation in a rotary evaporator. The crystals remaining are triturated with hexane, filtered off and dried in vacuo at 40° C.

6.1 g (83.8%) of the title compound of formula

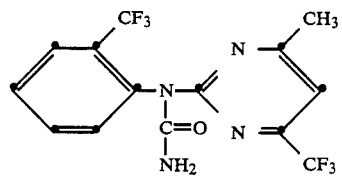

are isolated in the form of crystals having a melting point of 150°-153° C. (Comp. No. 1.020).

P. 1.2.
N-(2,5-dichlorophenyl)-N-(4,6-dimethylpyrimidin-2-yl)-urea 4.0 g (0.012 mole) of N-chlorocarbonyl-N-(4,6-dimethylpyrimidin-2-yl)-2,5-dichloroaniline are dissolved in 50 ml of chloroform. An excess of ammonia gas is introduced into the solution. When the exothermic reaction has subsided, the reaction mixture is washed twice with water, dried with magnesium sulfate and concentrated by evaporation.

Recrystallisation from ethanol yields 2.4 g (64.9%) of the title compound of formula

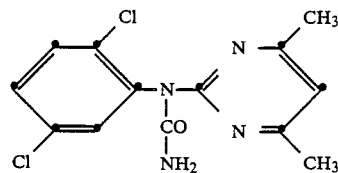

in the form of crystals having a melting point of 153° C. (decomp.) (Comp. No. 1.050).

The compounds of Table I can be obtained analogously to the P.1 Preparation Examples.

TABLE I

Compounds of formula

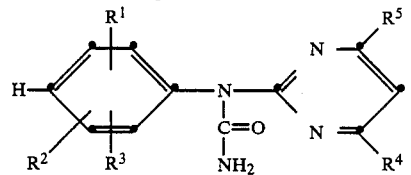

| Comp. No. | R¹ | R² | R³ | R⁴ | R⁵ | Physical data |
|---|---|---|---|---|---|---|
| 1.001 | 2-Cl | H | H | $CH_3$ | $CH_3$ | from 147° C. decomp. |
| 1.002 | 2-Cl | H | H | $CH_3$ | $OCHF_2$ | |
| 1.003 | 2-Cl | H | H | $CH_3$ | Cl | |
| 1.004 | 2-Cl | H | H | $CH_3$ | $CF_3$ | |
| 1.005 | 2-Cl | H | H | $CH_3$ | $CF_2CF_3$ | |
| 1.006 | 2-Cl | H | H | $CH_2CH_3$ | $CF_3$ | |
| 1.007 | 2-Cl | H | H | $CH_3$ | $CF_2Cl$ | |
| 1.008 | 2-Cl | H | H | $CH_3$ | $CHF_2$ | |
| 1.009 | 2-Br | H | H | $CH_3$ | Cl | m.p. 149–150° C. |
| 1.010 | 2-Br | H | H | $OCH_3$ | $CF_3$ | |
| 1.011 | 2-Br | H | H | $CH_3$ | $CF_3$ | |
| 1.012 | 2-Br | H | H | $SCH_3$ | $CF_3$ | |
| 1.013 | 2-Br | H | H | $CH_2CH_3$ | $CF_3$ | |
| 1.014 | 2-Br | H | H | $CH_3$ | $CHCl_2$ | |
| 1.015 | 2-Br | H | H | $CH_3$ | $CHFCl$ | |
| 1.016 | 2-Br | H | H | Cyclopropyl | $CF_3$ | m.p. 183–184° C. |
| 1.017 | 2-$CF_3$ | H | H | Phenyl | $CF_3$ | |
| 1.018 | 2-$CF_3$ | H | H | 2-Furyl | $CF_3$ | |
| 1.019 | 2-$CF_3$ | H | H | $CH_3$ | Cl | |
| 1.020 | 2-$CF_3$ | H | H | $CH_3$ | $CF_3$ | m.p. 150–153° C. |
| 1.021 | 2-$CF_3$ | H | H | $CH_3$ | $CH_3$ | m.p. 145–146° C. |
| 1.022 | 2-$CF_3$ | H | H | $CH_2CH_3$ | $CF_3$ | |
| 1.023 | 2-$CF_3$ | H | H | $CH(CH_3)_2$ | $CF_3$ | m.p. 137–138° C. |
| 1.024 | 2-$CF_3$ | H | H | (n)$C_3H_7$ | $CF_3$ | m.p. 153–154° C. |
| 1.025 | 2-$CF_3$ | H | H | $OCH_3$ | $CF_3$ | |
| 1.026 | 2-$CF_3$ | H | H | $OC_2H_5$ | $CF_3$ | |
| 1.027 | 2-$CF_3$ | H | H | $SCH_3$ | $CF_3$ | |
| 1.028 | 2-$CF_3$ | H | H | $SCH(CH_3)_2$ | $CF_3$ | |
| 1.029 | 2-$CF_3$ | H | H | $CH_3$ | $CF_2CF_3$ | |
| 1.030 | 2-$CF_3$ | H | H | $CH_3$ | $CHFCl$ | |
| 1.031 | 2-J | H | H | $CH_3$ | Cl | |
| 1.032 | 2-J | H | H | $CH_3$ | $CF_3$ | m.p. 168–160° C. |
| 1.033 | 2-J | H | H | $CH_2CH_3$ | $CF_3$ | |
| 1.034 | 2-J | H | H | $CH_3$ | $CF_2Cl$ | |
| 1.035 | 2-F | H | H | $CH_3$ | $CH_3$ | from 159° C. decomp. |

TABLE I-continued

Compounds of formula I

| Comp. No. | R¹ | R² | R³ | R⁴ | R⁵ | Physical data |
|---|---|---|---|---|---|---|
| 1.036 | 2-F | H | H | $CH_3$ | Cl | |
| 1.037 | 2-F | H | H | $CH_3$ | $CF_3$ | from 169° C. decomp. |
| 1.038 | 2-F | H | H | $CH(CH_3)_2$ | $CF_3$ | m.p. 144–146° C. |
| 1.039 | 2-F | H | H | Cl | $CF_3$ | |
| 1.040 | 2-F | H | H | $OC_2H_5$ | $CF_3$ | |
| 1.041 | 2-Cl | 3-Cl | H | $CH_3$ | Cl | m.p. 143–144° C. |
| 1.042 | 2-Cl | 3-Cl | H | $CH_3$ | $CF_3$ | m.p. 139–140° C. |
| 1.043 | 2-Cl | 3-Cl | H | $OCH_3$ | $CF_3$ | |
| 1.044 | 2-Cl | 3-Cl | H | $OC_4H_9(n)$ | $CF_3$ | |
| 1.045 | 2-Cl | 3-Cl | H | $SC_2H_5$ | $CF_3$ | |
| 1.046 | 2-Cl | 3-Cl | H | Phenyl | $CF_3$ | |
| 1.047 | 2-Cl | 3-Cl | H | $CH_3$ | $CF_2Cl$ | |
| 1.048 | 2-Cl | 3-Cl | H | $CH_3$ | CHFCl | |
| 1.049 | 2-Cl | 3-Cl | H | $CH_3$ | $CH_3$ | from 163° C. decomp. |
| 1.050 | 2-Cl | 5-Cl | H | $CH_3$ | $CH_3$ | from 153° C. decomp. |
| 1.051 | 2-Cl | 5-Cl | H | $CH_3$ | $OCHF_2$ | |
| 1.052 | 2-Cl | 5-Cl | H | $CH_3$ | Cl | m.p. 123–125° C. |
| 1.053 | 2-Cl | 5-Cl | H | $OCH_3$ | $CH_3$ | |
| 1.054 | 2-Cl | 5-Cl | H | $CH_3$ | Br | |
| 1.055 | 2-Cl | 5-Cl | H | $CH_3$ | $CF_3$ | m.p. 150–151° C. |
| 1.056 | 2-Cl | 5-Cl | H | $CH_2CH_3$ | $CF_3$ | m.p. 149–150° C. |
| 1.057 | 2-Cl | 5-Cl | H | $C_3H_7(n)$ | $CF_3$ | m.p. 148–149° C. |
| 1.058 | 2-Cl | 5-Cl | H | $C_3H_7(i)$ | $CF_3$ | m.p. 156–157° C. |
| 1.059 | 2-Cl | 5-Cl | H | Cyclopropyl | $CF_3$ | m.p. 174–175° C. |
| 1.060 | 2-Cl | 5-Cl | H | Phenyl | $CF_3$ | |
| 1.061 | 2-Cl | 5-Cl | H | 2-Thienyl | $CF_3$ | m.p. 177–178° C. |
| 1.062 | 2-Cl | 5-Cl | H | 2-Furyl | $CF_3$ | m.p. 168–169° C. |
| 1.063 | 2-Cl | 5-Cl | H | $CH_3$ | $CF_2CF_3$ | m.p. 157–158° C. |
| 1.064 | 2-Cl | 5-Cl | H | $CH_3$ | $CF_2Cl$ | m.p. 178–179° C. |
| 1.065 | 2-Cl | 5-Cl | H | $CH_3$ | $CHF_2$ | m.p. 159–160° C. |
| 1.066 | 2-Cl | 5-Cl | H | $CH_3$ | CHClF | m.p. 153–154° C. |
| 1.067 | 2-Cl | 5-Cl | H | $CH_2CH_3$ | $CF_2Cl$ | |
| 1.068 | 2-Cl | 5-Cl | H | $C_3H_7(i)$ | $CF_2Cl$ | m.p. 161–162° C. |
| 1.069 | 2-Cl | 5-Cl | H | $OCH_3$ | $CF_3$ | |
| 1.070 | 2-Cl | 5-Cl | H | $OC_2H_5$ | $CF_3$ | |
| 1.071 | 2-Cl | 5-Cl | H | $OC_3H_7$ | $CF_3$ | |
| 1.072 | 2-Cl | 5-Cl | H | $OC_3H_7(i)$ | $CF_3$ | |
| 1.073 | 2-Cl | 5-Cl | H | $OC_4H_9(n)$ | $CF_3$ | |
| 1.074 | 2-Cl | 5-Cl | H | $OC_4H_9(i)$ | $CF_3$ | |
| 1.075 | 2-Cl | 5-Cl | H | $SCH_3$ | $CF_3$ | |
| 1.076 | 2-Cl | 5-Cl | H | $SC_2H_5$ | $CF_3$ | |
| 1.077 | 2-Cl | 5-Cl | H | $SC_3H_7(n)$ | $CF_3$ | |
| 1.078 | 2-Cl | 5-Cl | H | $SC_3H_7(i)$ | $CF_3$ | |
| 1.079 | 2-Cl | 5-Cl | H | $SC_4H_9(n)$ | $CF_3$ | |
| 1.080 | 2-Cl | 5-Cl | H | $C_4H_9(n)$ | $CF_3$ | m.p. 123–124° C. |
| 1.081 | 2-Cl | 5-Cl | H | $C_4H_9(i)$ | $CF_3$ | |
| 1.082 | 2-Cl | 5-Cl | H | $C_4H_9(t)$ | $CF_3$ | m.p. 159–160° C. |
| 1.083 | 2-Cl | 5-Cl | H | $C_2H_5$ | $CF_2CF_3$ | m.p. 157–158° C. |
| 1.084 | 2-Cl | 5-Cl | H | $C_3H_7(i)$ | $CF_2CF_3$ | m.p. 161–162° C. |
| 1.085 | 2-Cl | 5-Cl | H | $C_3H_7(n)$ | $CF_2CF_3$ | |
| 1.086 | 2-Cl | 5-Cl | H | $OCF_2CHF_2$ | $CF_3$ | |
| 1.087 | 2-Cl | 5-Cl | H | $CH_3$ | $CCl_2CF_3$ | |
| 1.088 | 2-Cl | 5-Cl | H | $C_2H_5$ | $CCl_2CF_3$ | |
| 1.089 | 2-Cl | 5-Cl | H | $CH_3$ | $CHCl_2$ | m.p. 157–159° C. |
| 1.090 | 2-Cl | 5-Cl | H | $C_2H_5$ | $CHCl_2$ | |
| 1.091 | 2-Cl | 5-Cl | H | $CH_3$ | $CCl_2CH_3$ | |
| 1.092 | 2-Cl | 5-Cl | H | $C_2H_5$ | $CCl_2CH_3$ | |
| 1.093 | 2-Cl | 6-Cl | H | $CH_3$ | $CH_3$ | m.p. 173–174° C. |
| 1.094 | 2-Cl | 6-Cl | H | $CH_3$ | $C_2H_5$ | |
| 1.095 | 2-Cl | 6-Cl | H | $CH_3$ | $C_3H_7(i)$ | |
| 1.096 | 2-Cl | 6-Cl | H | $CH_3$ | Cl | m.p. 184–185° C. |
| 1.097 | 2-Cl | 6-Cl | H | $CH_3$ | $CCl_2CH_3$ | |
| 1.098 | 2-Cl | 6-Cl | H | $C_2H_5$ | $CCl_2CH_3$ | |
| 1.099 | 2-Cl | 6-Cl | H | $CH_3$ | $CHCl_2$ | |
| 1.100 | 2-Cl | 6-Cl | H | $C_2H_5$ | $CHCl_2$ | |
| 1.101 | 2-Cl | 6-Cl | H | $CH_3$ | $CCl_2CF_3$ | |
| 1.102 | 2-Cl | 6-Cl | H | $C_3H_7(i)$ | $CCl_2CF_3$ | |
| 1.103 | 2-Cl | 6-Cl | H | $CH_3$ | CHClF | |
| 1.104 | 2-Cl | 6-Cl | H | $C_2H_5$ | CHClF | |
| 1.105 | 2-Cl | 6-Cl | H | $CH_3$ | $CF_2Cl$ | |

TABLE I-continued

Compounds of formula I

| Comp. No. | R¹ | R² | R³ | R⁴ | R⁵ | Physical data |
|---|---|---|---|---|---|---|
| 1.106 | 2-Cl | 6-Cl | H | $C_2H_5$ | $CF_2Cl$ | |
| 1.107 | 2-Cl | 6-Cl | H | $C_3H_7(i)$ | $CF_2Cl$ | |
| 1.108 | 2-Cl | 6-Cl | H | $C_3H_7(n)$ | $CF_2Cl$ | |
| 1.109 | 2-Cl | 6-Cl | H | $CH_3$ | $CF_3$ | m.p. 156–157° C. |
| 1.110 | 2-Cl | 6-Cl | H | $C_2H_5$ | $CF_3$ | |
| 1.111 | 2-Cl | 6-Cl | H | $C_3H_7(n)$ | $CF_3$ | |
| 1.112 | 2-Cl | 6-Cl | H | $C_3H_7(i)$ | $CF_3$ | |
| 1.113 | 2-Cl | 6-Cl | H | Cyclopropyl | $CF_3$ | m.p. 187–188° C. |
| 1.114 | 2-Cl | 6-Cl | H | Phenyl | $CF_3$ | |
| 1.115 | 2-Cl | 6-Cl | H | 2-Thienyl | $CF_3$ | m.p. 201–202° C. |
| 1.116 | 2-Cl | 6-Cl | H | 2-Furyl | $CF_3$ | |
| 1.117 | 2-Cl | 6-Cl | H | $CH_3$ | $CF_2CF_3$ | |
| 1.118 | 2-Cl | 6-Cl | H | $C_2H_5$ | $CF_2CF_3$ | m.p. 168–169° C. |
| 1.119 | 2-Cl | 6-Cl | H | $C_3H_7(i)$ | $CF_2CF_3$ | m.p. 154–155° C. |
| 1.120 | 2-Cl | 6-Cl | H | $C_3H_7(n)$ | $CF_2CF_3$ | |
| 1.121 | 2-Cl | 6-Cl | H | Cyclopropyl | $CF_2CF_3$ | |
| 1.122 | 2-Cl | 6-Cl | H | $CH_3$ | $OCHF_2$ | |
| 1.123 | 2-Cl | 6-Cl | H | $C_4H_9(n)$ | $CF_3$ | |
| 1.124 | 2-Cl | 6-Cl | H | $C_4H_9(i)$ | $CF_3$ | |
| 1.125 | 2-Cl | 6-Cl | H | $C_4H_9(t)$ | $CF_3$ | m.p. 174–175° C. |
| 1.126 | 2-Cl | 6-Cl | H | $OCH_3$ | $CF_3$ | |
| 1.127 | 2-Cl | 6-Cl | H | $OC_2H_5$ | $CF_3$ | |
| 1.128 | 2-Cl | 6-Cl | H | $OC_3H_7(n)$ | $CF_3$ | |
| 1.129 | 2-Cl | 6-Cl | H | $OC_3H_7(i)$ | $CF_3$ | |
| 1.130 | 2-Cl | 6-Cl | H | $OC_4H_9(n)$ | $CF_3$ | |
| 1.131 | 2-Cl | 6-Cl | H | $OC_4H_9(i)$ | $CF_3$ | |
| 1.132 | 2-Cl | 6-Cl | H | $SCH_3$ | $CF_3$ | m.p. 158–159° C. |
| 1.133 | 2-Cl | 6-Cl | H | $SC_2H_5$ | $CF_3$ | |
| 1.134 | 2-Cl | 6-Cl | H | $SC_3H_7(n)$ | $CF_3$ | |
| 1.135 | 2-Cl | 6-Cl | H | $SC_3H_7(i)$ | $CF_3$ | |
| 1.136 | 2-Cl | 6-Cl | H | $SC_4H_9(n)$ | $CF_3$ | |
| 1.137 | 2-Cl | 6-Cl | H | $OCH_3$ | $CH_3$ | |
| 1.138 | 2-Cl | 6-Cl | H | $C_2H_5$ | Cl | |
| 1.139 | 2-Cl | 6-Cl | H | $OCH_3$ | $C_2H_5$ | |
| 1.140 | 2-Cl | 6-Cl | H | $C_2H_5$ | $OCHF_2$ | |
| 1.141 | 2-Cl | 6-Cl | 3-$CH_3$ | $CH_3$ | $CF_3$ | m.p. 182° C. decomp. |
| 1.142 | 2-Cl | 6-Cl | 3-$CH_3$ | $C_2H_5$ | $CF_3$ | |
| 1.143 | 2-Cl | 6-Cl | 3-$CH_3$ | $C_3H_7(n)$ | $CF_3$ | |
| 1.144 | 2-Cl | 6-Cl | 3-$CH_3$ | $C_3H_7(i)$ | $CF_3$ | m.p. 160–162° C. |
| 1.145 | 2-Cl | 6-Cl | 3-$CH_3$ | $CH_3$ | $CF_2CF_3$ | m.p. 164–166° C. |
| 1.146 | 2-Cl | 6-Cl | 3-$CH_3$ | $C_2H_5$ | $CF_2CF_3$ | |
| 1.147 | 2-Cl | 6-Cl | 3-$CH_3$ | Cl | $CF_3$ | |
| 1.148 | 2-Cl | 6-Cl | 3-$CH_3$ | $OCH_3$ | $CF_3$ | |
| 1.149 | 2-Cl | 6-Cl | 3-$CH_3$ | $OC_2H_5$ | $CF_3$ | |
| 1.150 | 2-Cl | 6-Cl | 3-$CH_3$ | $SCH_3$ | $CF_3$ | |
| 1.151 | 2-Cl | 6-Cl | 3-$CH_3$ | $SC_4H_9(n)$ | $CF_3$ | |
| 1.152 | 2-Cl | 6-Cl | 3-$CH_3$ | $CH_3$ | $CF_2Cl$ | |
| 1.153 | 2-Cl | 6-Cl | 3-$CH_3$ | $CH_3$ | $CHF_2$ | |
| 1.154 | 2-Cl | 6-Cl | 3-$CH_3$ | $CH_3$ | $CHCl_2$ | |
| 1.155 | 2-Cl | 3-$CF_3$ | H | $CH_3$ | Cl | |
| 1.156 | 2-Cl | 3-$CF_3$ | H | $CH_3$ | $CH_3$ | |
| 1.157 | 2-Cl | 3-$CF_3$ | H | $CH_3$ | $CF_3$ | |
| 1.158 | 2-Cl | 3-$CF_3$ | H | $C_2H_5$ | $CF_3$ | |
| 1.159 | 2-Cl | 3-$CF_3$ | H | $C_3H_7(n)$ | $CF_3$ | |
| 1.160 | 2-Cl | 3-$CF_3$ | H | $CH_3$ | $CF_2CF_3$ | |
| 1.161 | 2-Cl | 3-$CF_3$ | H | $CH_3$ | $CClF_2$ | |
| 1.162 | 2-Cl | 3-$CF_3$ | H | $CH_3$ | $CHClF$ | |
| 1.163 | 2-Cl | 5-$CF_3$ | H | $CH_3$ | Cl | m.p. 148–149° C. |
| 1.164 | 2-Cl | 5-$CF_3$ | H | $CH_3$ | $CF_3$ | m.p. 144–145° C. |
| 1.165 | 2-Cl | 5-$CF_3$ | H | $CH_3$ | $CClF_2$ | |
| 1.166 | 2-Cl | 5-$CF_3$ | H | $C_2H_5$ | $CF_3$ | |
| 1.167 | 2-Cl | 5-$CF_3$ | H | $OCH_3$ | $CF_3$ | |
| 1.168 | 2-Cl | 6-$CF_3$ | H | $CH_3$ | Cl | |
| 1.169 | 2-Cl | 6-$CF_3$ | H | $CH_3$ | $CH_3$ | |
| 1.170 | 2-Cl | 6-$CF_3$ | H | $CH_3$ | $CF_3$ | m.p. 155–156° C. |
| 1.171 | 2-Cl | 6-$CF_3$ | H | $C_2H_5$ | $CF_3$ | |
| 1.172 | 2-Cl | 6-$CF_3$ | H | $C_3H_7(n)$ | $CF_3$ | |
| 1.173 | 2-Cl | 6-$CF_3$ | H | $C_3H_7(i)$ | $CF_3$ | |
| 1.174 | 2-Cl | 6-$CF_3$ | H | Cyclopropyl | $CF_3$ | |
| 1.175 | 2-Cl | 6-$CF_3$ | H | $C_4H_9(n)$ | $CF_3$ | |

TABLE I-continued

Compounds of formula I

| Comp. No. | $R^1$ | $R^2$ | $R^3$ | $R^4$ | $R^5$ | Physical data |
|---|---|---|---|---|---|---|
| 1.176 | 2-Cl | 6-CF$_3$ | H | C$_4$H$_9$(i) | CF$_3$ | |
| 1.177 | 2-Cl | 6-CF$_3$ | H | C$_4$H$_9$(t) | CF$_3$ | |
| 1.178 | 2-Cl | 6-CF$_3$ | H | CH$_3$ | CF$_2$CF$_3$ | |
| 1.179 | 2-Cl | 6-CF$_3$ | H | C$_2$H$_5$ | CF$_2$CF$_3$ | |
| 1.180 | 2-Cl | 6-CF$_3$ | H | CH$_3$ | CHCl$_2$ | |
| 1.181 | 2-Cl | 6-CF$_3$ | H | CH$_3$ | CClF$_2$ | |
| 1.182 | 2-Cl | 6-CF$_3$ | H | C$_2$H$_5$ | CClF$_2$ | |
| 1.183 | 2-Cl | 6-CF$_3$ | H | CH$_3$ | CHF$_2$ | |
| 1.184 | 2-Cl | 6-CF$_3$ | H | CH$_3$ | OCHF$_2$ | |
| 1.185 | 2-Cl | 6-CF$_3$ | H | OCH$_3$ | CF$_3$ | |
| 1.186 | 2-Cl | 6-CF$_3$ | H | OC$_2$H$_5$ | CF$_3$ | |
| 1.187 | 2-Cl | 6-CF$_3$ | H | SC$_2$H$_5$ | CF$_3$ | |
| 1.188 | 2-Cl | 6-CF$_3$ | H | CH$_3$ | CCl$_2$CF$_3$ | |
| 1.189 | 2-Cl | 6-CF$_3$ | H | CH$_3$ | CCl$_2$CH$_3$ | |
| 1.190 | 2-Cl | 6-CF$_3$ | H | Phenyl | CF$_3$ | |
| 1.191 | 2-Cl | 3-CH$_3$ | H | CH$_3$ | CF$_3$ | |
| 1.192 | 2-Cl | 3-CH$_3$ | H | CH$_3$ | CF$_2$CF$_3$ | |
| 1.193 | 2-Cl | 3-CH$_3$ | H | C$_2$H$_5$ | CF$_3$ | |
| 1.194 | 2-Cl | 3-CH$_3$ | H | C$_3$H$_7$(n) | CF$_3$ | |
| 1.195 | 2-Cl | 3-CH$_3$ | H | C$_3$H$_7$(i) | CF$_3$ | |
| 1.196 | 2-Cl | 3-CH$_3$ | H | CH$_3$ | Cl | |
| 1.197 | 2-Cl | 3-CH$_3$ | H | CH$_3$ | CF$_2$Cl | |
| 1.198 | 2-Cl | 3-CH$_3$ | H | CH$_3$ | CHCl$_2$ | |
| 1.199 | 2-Cl | 3-CH$_3$ | H | CH$_3$ | CHClF | |
| 1.200 | 2-Cl | 3-CH$_3$ | H | OCH$_3$ | CF$_3$ | |
| 1.201 | 2-Cl | 5-CH$_3$ | H | CH$_3$ | Cl | m.p. 140–141° C. |
| 1.202 | 2-Cl | 5-CH$_3$ | H | CH$_3$ | CHCl$_2$ | |
| 1.203 | 2-Cl | 5-CH$_3$ | H | CH$_3$ | CCl$_2$CF$_3$ | |
| 1.204 | 2-Cl | 5-CH$_3$ | H | CH$_3$ | CHClF | |
| 1.205 | 2-Cl | 5-CH$_3$ | H | CH$_3$ | CF$_2$Cl | |
| 1.206 | 2-Cl | 5-CH$_3$ | H | C$_2$H$_5$ | CF$_2$Cl | |
| 1.207 | 2-Cl | 5-CH$_3$ | H | CH$_3$ | CF$_3$ | |
| 1.208 | 2-Cl | 5-CH$_3$ | H | C$_2$H$_5$ | CF$_3$ | |
| 1.209 | 2-Cl | 5-CH$_3$ | H | C$_3$H$_7$(n) | CF$_3$ | |
| 1.210 | 2-Cl | 5-CH$_3$ | H | C$_3$H$_7$(i) | CF$_3$ | |
| 1.211 | 2-Cl | 5-CH$_3$ | H | C$_4$H$_9$(n) | CF$_3$ | |
| 1.212 | 2-Cl | 5-CH$_3$ | H | C$_4$H$_9$(t) | CF$_3$ | |
| 1.213 | 2-Cl | 5-CH$_3$ | H | 2-Furyl | CF$_3$ | |
| 1.214 | 2-Cl | 5-CH$_3$ | H | CH$_3$ | CF$_2$CF$_3$ | |
| 1.215 | 2-Cl | 5-CH$_3$ | H | C$_2$H$_4$ | CF$_2$CF$_3$ | |
| 1.216 | 2-Cl | 5-CH$_3$ | H | OCH$_3$ | CF$_3$ | |
| 1.217 | 2-Cl | 5-CH$_3$ | H | OC$_2$H$_5$ | CF$_3$ | |
| 1.218 | 2-Cl | 5-CH$_3$ | H | SCH$_3$ | CF$_3$ | |
| 1.219 | 2-Cl | 6-CH$_3$ | H | CH$_3$ | Cl | m.p. 167–168° C. |
| 1.220 | 2-Cl | 6-CH$_3$ | H | CN | CH$_3$ | |
| 1.221 | 2-Cl | 6-CH$_3$ | H | CH$_3$ | CF$_3$ | m.p. 192–193° C. |
| 1.222 | 2-Cl | 6-CH$_3$ | H | CH$_3$ | CF$_2$Cl | m.p. 185–187° C. |
| 1.223 | 2-Cl | 6-CH$_3$ | H | CH$_3$ | CF$_2$CF$_3$ | |
| 1.224 | 2-Cl | 6-CH$_3$ | H | CH$_3$ | CCl$_2$CF$_3$ | |
| 1.225 | 2-Cl | 6-CH$_3$ | H | CH$_3$ | CHF$_2$ | |
| 1.226 | 2-Cl | 6-CH$_3$ | H | CH$_3$ | CHCl$_2$ | |
| 1.227 | 2-Cl | 6-CH$_3$ | H | C$_2$H$_5$ | CF$_3$ | m.p. 155–157° C. |
| 1.228 | 2-Cl | 6-CH$_3$ | H | C$_3$H$_7$(i) | CF$_3$ | m.p. 146–148° C. |
| 1.229 | 2-Cl | 6-CH$_3$ | H | Cyclopropyl | CF$_3$ | m.p. 177–178° C. |
| 1.230 | 2-Cl | 6-CH$_3$ | H | C$_4$H$_9$(i) | CF$_3$ | |
| 1.231 | 2-Cl | 6-CH$_3$ | H | C$_2$H$_5$ | CF$_2$CF$_3$ | |
| 1.232 | 2-Cl | 6-CH$_3$ | H | OCH$_3$ | CF$_3$ | |
| 1.233 | 2-Cl | 6-CH$_3$ | H | OCH$_2$CH$_2$Cl | CF$_3$ | |
| 1.234 | 2-Cl | 6-CH$_3$ | H | OCH$_2$CH$_2$OCH$_3$ | CF$_3$ | |
| 1.235 | 2-Cl | 6-CH$_3$ | H | OC$_2$H$_5$ | CF$_3$ | |
| 1.236 | 2-Cl | 6-CH$_3$ | H | SCH$_3$ | CF$_3$ | |
| 1.237 | 2-Cl | 6-CH$_3$ | H | SC$_2$H$_5$ | CF$_3$ | |
| 1.238 | 2-Cl | 6-CH$_3$ | H | SC$_3$H$_7$(i) | CF$_3$ | |
| 1.239 | 2-Cl | 6-CH$_3$ | H | SC$_4$H$_9$(i) | CF$_3$ | |
| 1.240 | 2-Cl | 5-OCH$_3$ | H | CH$_3$ | CF$_3$ | |
| 1.241 | 2-Cl | 5-OCH$_3$ | H | C$_2$H$_5$ | CF$_3$ | |
| 1.242 | 2-Cl | 5-OCH$_3$ | H | CH$_3$ | Cl | |
| 1.243 | 2-Cl | 5-OCH$_3$ | H | OCH$_3$ | CF$_3$ | |
| 1.244 | 2-Cl | 5-OCH$_3$ | H | CH$_3$ | CHF$_2$ | |
| 1.245 | 2-Cl | 5-OCH$_3$ | H | CH$_3$ | CF$_2$CF$_3$ | |

TABLE I-continued

Compounds of formula I

| Comp. No. | R$^1$ | R$^2$ | R$^3$ | R$^4$ | R$^5$ | Physical data |
|---|---|---|---|---|---|---|
| 1.246 | 2-Cl | 5-OCH$_3$ | H | CH$_3$ | CF$_2$Cl | |
| 1.247 | 2-Cl | 5-COOCH$_3$ | H | CH$_3$ | CF$_3$ | m.p. 152–153° C. |
| 1.248 | 2-Cl | 5-COOCH$_3$ | H | C$_2$H$_5$ | CF$_3$ | |
| 1.249 | 2-Cl | 5-COOC$_2$H$_5$ | H | CH$_3$ | CF$_3$ | |
| 1.250 | 2-Cl | 5-COOC$_2$H$_5$ | H | CH$_3$ | CF$_2$CF$_3$ | |
| 1.251 | 2-Cl | 5-COOC$_3$H$_7$(i) | H | CH$_3$ | CF$_3$ | |
| 1.252 | 2-Cl | 5-COOC$_3$H$_7$(i) | H | C$_3$H$_7$(i) | CF$_3$ | |
| 1.253 | 2-Cl | 5-COOC$_3$H$_7$(i) | H | CH$_3$ | CF$_2$Cl | |
| 1.254 | 2-Cl | 5-COOC$_3$H$_7$(i) | H | Phenyl | CF$_3$ | |
| 1.255 | 2-Cl | 5-COOC$_3$H$_7$(i) | H | Cyclopropyl | CF$_3$ | |
| 1.256 | 2-Cl | 5-COOC$_3$H$_7$(i) | H | CH$_3$ | CHFCl | |
| 1.257 | 3-Cl | 5-Cl | H | CH$_3$ | Cl | m.p. 117–118° C. |
| 1.258 | 3-Cl | 5-Cl | H | CH$_3$ | CF$_3$ | m.p. 129–130° C. |
| 1.259 | 3-Cl | 5-Cl | H | C$_2$H$_5$ | CF$_3$ | |
| 1.260 | 3-Cl | 5-Cl | H | C$_3$H$_7$(n) | CF$_3$ | |
| 1.261 | 3-Cl | 5-Cl | H | C$_3$H$_7$(i) | CF$_3$ | |
| 1.262 | 3-Cl | 5-Cl | H | Cyclopropyl | CF$_3$ | |
| 1.263 | 3-Cl | 5-Cl | H | Phenyl | CF$_3$ | |
| 1.264 | 3-Cl | 5-Cl | H | CH$_3$ | CHF$_2$ | |
| 1.265 | 3-Cl | 5-Cl | H | CH$_3$ | CF$_2$Cl | |
| 1.266 | 3-Cl | 5-Cl | H | C$_2$H$_5$ | CF$_2$Cl | |
| 1.267 | 3-Cl | 5-Cl | H | OCH$_3$ | CF$_3$ | |
| 1.268 | 3-Cl | 5-Cl | H | OC$_2$H$_5$ | CF$_3$ | |
| 1.269 | 3-Cl | 5-Cl | H | SCH$_3$ | CF$_3$ | |
| 1.270 | 3-Cl | 5-Cl | H | SC$_3$H$_7$(i) | CF$_3$ | |
| 1.271 | 2-CH$_3$ | 5-Cl | H | CH$_3$ | Cl | m.p. 141–142° C. |
| 1.272 | 2-CH$_3$ | 5-Cl | H | CH$_3$ | CF$_3$ | |
| 1.273 | 2-CH$_3$ | 5-Cl | H | CN | CF$_3$ | |
| 1.274 | 2-CH$_3$ | 5-Cl | H | C$_2$H$_5$ | Cl | |
| 1.275 | 2-CH$_3$ | 5-Cl | H | CH$_3$ | OCHF$_2$ | |
| 1.276 | 2-CH$_3$ | 5-Cl | H | CH$_3$ | Br | |
| 1.277 | 2-CH$_3$ | 5-Cl | H | CH$_3$ | F | |
| 1.278 | 2-CH$_3$ | 5-Cl | H | CH$_3$ | CH$_3$ | m.p. 150–151° C. |
| 1.279 | 2-CH$_3$ | 5-Cl | H | OCH$_3$ | CH$_3$ | |
| 1.280 | 2-CH$_3$ | 5-Cl | H | C$_2$H$_5$ | CF$_3$ | |
| 1.281 | 2-CH$_3$ | 5-Cl | H | C$_3$H$_7$(n) | CF$_3$ | |
| 1.282 | 2-CH$_3$ | 5-Cl | H | C$_3$H$_7$(i) | CF$_3$ | |
| 1.283 | 2-CH$_3$ | 5-Cl | H | Cyclopropyl | CF$_3$ | |
| 1.284 | 2-CH$_3$ | 5-Cl | H | Phenyl | CF$_3$ | |
| 1.285 | 2-CH$_3$ | 5-Cl | H | C$_4$H$_9$(n) | CF$_3$ | |
| 1.286 | 2-CH$_3$ | 5-Cl | H | C$_4$H$_9$(i) | CF$_3$ | |
| 1.287 | 2-CH$_3$ | 5-Cl | H | C$_4$H$_9$(t) | CF$_3$ | |
| 1.288 | 2-CH$_3$ | 5-Cl | H | CH$_3$ | CF$_2$CF$_3$ | |
| 1.289 | 2-CH$_3$ | 5-Cl | H | C$_2$H$_5$ | CF$_2$CF$_3$ | |
| 1.290 | 2-CH$_3$ | 5-Cl | H | C$_3$H$_7$(i) | CF$_3$CF$_3$ | |
| 1.291 | 2-CH$_3$ | 5-Cl | H | CH$_3$ | CF$_2$Cl | |
| 1.292 | 2-CH$_3$ | 5-Cl | H | C$_2$H$_5$ | CF$_2$Cl | |
| 1.293 | 2-CH$_3$ | 5-Cl | H | CH$_3$ | CHF$_2$ | |
| 1.294 | 2-CH$_3$ | 5-Cl | H | C$_2$H$_5$ | CHF$_2$ | |
| 1.295 | 2-CH$_3$ | 5-Cl | H | CH$_3$ | CHFCl | |
| 1.296 | 2-CH$_3$ | 5-Cl | H | C$_2$H$_5$ | CHFCl | |
| 1.297 | 2-CH$_3$ | 5-Cl | H | CH$_3$ | CHCl$_2$ | |
| 1.298 | 2-CH$_3$ | 5-Cl | H | C$_2$H$_5$ | CHCl$_2$ | |
| 1.299 | 2-CH$_3$ | 5-Cl | H | CH$_3$ | CCl$_2$CF$_3$ | |
| 1.300 | 2-CH$_3$ | 5-Cl | H | CH$_3$ | CCl$_2$CH$_3$ | |
| 1.301 | 2-CH$_3$ | 5-Cl | H | OCH$_3$ | CF$_3$ | |
| 1.302 | 2-CH$_3$ | 5-Cl | H | OC$_2$H$_5$ | CF$_3$ | |
| 1.303 | 2-CH$_3$ | 5-Cl | H | SCH$_3$ | CF$_3$ | |
| 1.304 | 2-CH$_3$ | 5-Cl | H | SC$_2$H$_5$ | CF$_3$ | |
| 1.305 | 2-CH$_3$ | 5-Cl | H | SC$_4$H$_9$(i) | CF$_3$ | |
| 1.306 | 2-CH$_3$ | 3-Cl | H | CH$_3$ | Cl | m.p. 155–156° C. |
| 1.307 | 2-CH$_3$ | 3-Cl | H | CH$_3$ | CF$_3$ | |
| 1.308 | 2-CH$_3$ | 3-Cl | H | C$_2$H$_5$ | CF$_3$ | |
| 1.309 | 2-CH$_3$ | 3-Cl | H | C$_3$H$_7$(i) | CF$_3$ | |
| 1.310 | 2-CH$_3$ | 3-Cl | H | Cyclopropyl | CF$_3$ | |
| 1.311 | 2-CH$_3$ | 3-Cl | H | CH$_3$ | CF$_2$Cl | |
| 1.312 | 2-CH$_3$ | 3-Cl | H | CH$_3$ | CF$_2$CF$_3$ | |
| 1.313 | 2-CH$_3$ | 3-Cl | H | C$_2$H$_5$ | CF$_2$CF$_3$ | |
| 1.314 | 2-CH$_3$ | 3-Cl | H | OCH$_3$ | CF$_3$ | |
| 1.315 | 2-CH$_3$ | 3-Cl | H | SCH$_3$ | CF$_3$ | |

TABLE I-continued

Compounds of formula I

| Comp. No. | R¹ | R² | R³ | R⁴ | R⁵ | Physical data |
|---|---|---|---|---|---|---|
| 1.316 | 2-CH₃ | 5-NO₂ | H | CH₃ | Cl | m.p. 142–143° C. |
| 1.317 | 2-CH₃ | 5-NO₂ | H | CH₃ | CF₃ | |
| 1.318 | 2-CH₃ | 5-NO₂ | H | CH₃ | CF₂Cl | |
| 1.319 | 2-CH₃ | 5-NO₂ | H | CH₃ | CHF₂ | |
| 1.320 | 2-CH₃ | 5-NO₂ | H | C₂H₅ | CF₃ | |
| 1.321 | 2-CH₃ | 5-NO₂ | H | C₃H₇(n) | CF₃ | |
| 1.322 | 2-CH₃ | 5-NO₂ | H | C₃H₇(i) | CF₃ | |
| 1.323 | 2-CH₃ | 5-NO₂ | H | C₄H₉(t) | CF₃ | |
| 1.324 | 2-CH₃ | 3-NO₂ | H | CH₃ | Cl | m.p. 158–159° C. |
| 1.325 | 2-CH₃ | 3-NO₂ | H | CH₃ | CF₃ | |
| 1.326 | 2-CH₃ | 3-NO₂ | H | CH₃ | CF₂CF₃ | |
| 1.327 | 2-CH₃ | 3-NO₂ | H | C₂H₅ | CF₂CF₃ | |
| 1.328 | 2-CH₃ | 3-NO₂ | H | Phenyl | CF₃ | |
| 1.329 | 2-CH₃ | 3-NO₂ | H | C₂H₅ | CF₃ | |
| 1.330 | 2-CH₃ | 3-NO₂ | H | C₃H₇(i) | CF₃ | |
| 1.331 | 2-CH₃ | 6-CF₃ | H | CH₃ | Cl | |
| 1.332 | 2-CH₃ | 6-CF₃ | H | CH₃ | CF₃ | m.p. 164–165° C. |
| 1.333 | 2-CH₃ | 6-CF₃ | H | CH₃ | CHF₂ | |
| 1.334 | 2-CH₃ | 6-CF₃ | H | CH₃ | CF₂Cl₂ | |
| 1.335 | 2-CH₃ | 6-CF₃ | H | CH₃ | CHCl₂ | |
| 1.336 | 2-CH₃ | 6-CF₃ | H | OCH₃ | CF₃ | |
| 1.337 | 2-CH₃ | 6-CF₃ | H | OC₂H₅ | CF₃ | |
| 1.338 | 2-CH₃ | 6-CF₃ | H | SCH₃ | CF₃ | |
| 1.339 | 2-CH₃ | 6-CF₃ | H | SC₂H₅ | CF₃ | |
| 1.340 | 2-CH₃ | 6-CF₃ | H | C₂H₅ | CF₃ | |
| 1.341 | 2-CH₃ | 6-CF₃ | H | CH₃ | CF₂CF₃ | |
| 1.342 | 2-CH₃ | 6-CF₃ | H | C₂H₅ | CF₂CF₃ | |
| 1.343 | 2-CH₃ | 6-CF₃ | H | C₃H₇(i) | CF₃ | |
| 1.344 | 2-CH₃ | 6-CF₃ | H | C₃H₇(n) | CF₃ | |
| 1.345 | 2-CH₃ | 6-CF₃ | H | Cyclopropyl | CF₃ | |
| 1.346 | 2-OCHF₂ | 5-Cl | H | CH₃ | Cl | m.p. 138–139° C. |
| 1.347 | 2-OCHF₂ | 5-Cl | H | CH₃ | CH₃ | |
| 1.348 | 2-OCHF₂ | 5-Cl | H | CH₃ | CHCl₂ | |
| 1.349 | 2-OCHF₂ | 5-Cl | H | CH₃ | CHFCl | |
| 1.350 | 2-OCHF₂ | 5-Cl | H | CH₃ | CHF₂ | |
| 1.351 | 2-OCHF₂ | 5-Cl | H | CH₃ | CF₂Cl | |
| 1.352 | 2-OCHF₂ | 5-Cl | H | CH₃ | CF₃ | m.p. 142–143° C. |
| 1.353 | 2-OCHF₂ | 5-Cl | H | CH₃ | CF₂CF₃ | |
| 1.354 | 2-OCHF₂ | 5-Cl | H | CH₃ | CCl₂CF₃ | |
| 1.355 | 2-OCHF₂ | 5-Cl | H | CH₃ | CCl₂CH₃ | |
| 1.356 | 2-OCHF₂ | 5-Cl | H | C₂H₅ | CF₃ | |
| 1.357 | 2-OCHF₂ | 5-Cl | H | C₃H₇(n) | CF₃ | |
| 1.358 | 2-OCHF₂ | 5-Cl | H | C₃H₇(i) | CF₃ | |
| 1.359 | 2-CH₃ | 6-Cl | H | Cyclopropyl | CF₃ | |
| 1.360 | 2-CH₃ | 6-Cl | H | C₄H₉(n) | CF₃ | |
| 1.361 | 2-CH₃ | 6-Cl | H | C₄H₉(i) | CF₃ | |
| 1.362 | 2-CH₃ | 6-Cl | H | C₄H₉(t) | CF₃ | |
| 1.363 | 2-CH₃ | 6-Cl | H | Phenyl | CF₃ | |
| 1.364 | 2-CH₃ | 6-Cl | H | 2-Furyl | CF₃ | |
| 1.365 | 2-CH₃ | 6-Cl | H | 2-Thienyl | CF₃ | |
| 1.366 | 2-CH₃ | 6-Cl | H | C₂H₅ | CF₂CF₃ | |
| 1.367 | 2-CH₃ | 6-Cl | H | C₂H₅ | CCl₂CH₃ | |
| 1.368 | 2-CH₃ | 6-Cl | H | OCH₃ | CF₃ | |
| 1.369 | 2-CH₃ | 6-Cl | H | OC₂H₅ | CF₃ | |
| 1.370 | 2-CH₃ | 6-Cl | H | SCH₃ | CF₃ | |
| 1.371 | 2-Cl | 6-Cl | 3-Cl | CH₃ | Cl | |
| 1.372 | 2-Cl | 6-Cl | 3-Cl | CH₃ | CF₃ | |
| 1.373 | 2-Cl | 6-Cl | 3-Cl | C₂H₅ | CF₃ | |
| 1.374 | 2-Cl | 6-Cl | 3-Cl | C₃H₇(i) | CF₃ | |
| 1.375 | 2-Cl | 6-Cl | 3-Cl | CH₃ | CF₂CF₃ | |
| 1.376 | 2-Cl | 6-Cl | 3-Cl | Phenyl | CF₃ | |
| 1.377 | 2-Cl | 6-Cl | 3-Cl | OCH₃ | CF₃ | |
| 1.378 | 2-Cl | 6-Cl | 3-Cl | OC₂H₅ | CF₃ | |
| 1.379 | 2-Cl | 6-Cl | 3-Cl | SC₂H₅ | CF₃ | |
| 1.380 | 2-OCH₃ | 3-Cl | H | CH₃ | CF₃ | m.p. 179–180° C. |
| 1.381 | 2-OCH₃ | 3-Cl | H | C₂H₅ | CF₃ | |
| 1.382 | 2-OCH₃ | 3-Cl | H | C₃H₇(n) | CF₃ | |
| 1.383 | 2-OCH₃ | 3-Cl | H | Cyclopropyl | CF₃ | |
| 1.384 | 2-OCH₃ | 3-Cl | H | CH₃ | Cl | |
| 1.385 | 2-OCH₃ | 3-Cl | H | CH₃ | CF₂CF₃ | |

TABLE I-continued

Compounds of formula I

| Comp. No. | $R^1$ | $R^2$ | $R^3$ | $R^4$ | $R^5$ | Physical data |
|---|---|---|---|---|---|---|
| 1.386 | 2-OCH$_3$ | 3-Cl | H | OCH$_3$ | CF$_3$ | |
| 1.387 | 2-OCH$_3$ | 3-Cl | H | SCH$_3$ | CF$_3$ | |
| 1.388 | 2-OCH$_3$ | 3-Cl | H | CH$_3$ | CF$_2$Cl | |
| 1.389 | 2-OCH$_3$ | 3-Cl | H | CH$_3$ | CHF$_2$ | |
| 1.390 | 2-OCH$_3$ | 5-Cl | H | CH$_3$ | Cl | |
| 1.391 | 2-OCH$_3$ | 5-Cl | H | CH$_3$ | CH$_3$ | m.p. 157–158° C. |
| 1.392 | 2-OCH$_3$ | 5-Cl | H | CH$_3$ | CF$_3$ | m.p. 158–159° C. |
| 1.393 | 2-OCH$_3$ | 5-Cl | H | CH$_3$ | Br | |
| 1.394 | 2-OCH$_3$ | 5-Cl | H | CN | CH$_3$ | |
| 1.395 | 2-OCH$_3$ | 5-Cl | H | CH$_3$ | CF$_2$Cl | |
| 1.396 | 2-OCH$_3$ | 5-Cl | H | CH$_3$ | CHF$_2$ | |
| 1.397 | 2-OCH$_3$ | 5-Cl | H | CH$_3$ | CHCl$_2$ | |
| 1.398 | 2-OCH$_3$ | 5-Cl | H | CH$_3$ | CF$_2$CF$_3$ | m.p. 125–126° C. |
| 1.399 | 2-OCH$_3$ | 5-Cl | H | CH$_3$ | CCl$_2$CF$_3$ | |
| 1.400 | 2-OCH$_3$ | 5-Cl | H | CH$_3$ | CHClF | |
| 1.401 | 2-OCH$_3$ | 5-Cl | H | CH$_3$ | CCl$_2$CH$_3$ | |
| 1.402 | 2-OCH$_3$ | 5-Cl | H | C$_2$H$_5$ | CF$_3$ | |
| 1.403 | 2-OCH$_3$ | 5-Cl | H | C$_2$H$_5$ | CF$_2$CF$_3$ | m.p. 148–150° C. |
| 1.404 | 2-OCH$_3$ | 5-Cl | H | C$_2$H$_5$ | CF$_2$Cl | |
| 1.405 | 2-OCH$_3$ | 5-Cl | H | C$_3$H$_7$(n) | CF$_3$ | m.p. 168–169° C. |
| 1.406 | 2-OCH$_3$ | 5-Cl | H | C$_3$H$_7$(i) | | m.p. 167–168° C. |
| 1.407 | 2-OCH$_3$ | 5-Cl | H | C$_3$H$_7$(i) | CF$_2$CF$_3$ | |
| 1.408 | 2-OCH$_3$ | 5-Cl | H | Cyclopropyl | CF$_3$ | |
| 1.409 | 2-OCH$_3$ | 5-Cl | H | C$_4$H$_9$(n) | CF$_3$ | |
| 1.410 | 2-OCH$_3$ | 5-Cl | H | C$_2$H$_5$(i) | CF$_3$ | |
| 1.411 | 2-OCH$_3$ | 5-Cl | H | C$_4$H$_9$(t) | CF$_3$ | m.p. 156–157° C. |
| 1.412 | 2-OCH$_3$ | 5-Cl | H | OCH$_3$ | CF$_3$ | |
| 1.413 | 2-OCH$_3$ | 5-Cl | H | OC$_4$H$_9$(n) | CF$_3$ | |
| 1.414 | 2-OCH$_3$ | 5-Cl | H | SCH$_3$ | CF$_3$ | |
| 1.415 | 2-OCH$_3$ | 5-Cl | H | SC$_2$H$_5$ | CF$_3$ | |
| 1.416 | 2-OCH$_3$ | 5-Cl | H | SC$_3$H$_7$(n) | CF$_3$ | |
| 1.417 | 2-OCH$_3$ | 5-Cl | H | SC$_3$H$_7$(i) | CF$_3$ | |
| 1.418 | 2-OC$_2$H$_5$ | 5-Cl | H | CH$_3$ | Cl | |
| 1.419 | 2-OC$_2$H$_5$ | 5-Cl | H | CH$_3$ | CF$_3$ | |
| 1.420 | 2-OC$_2$H$_5$ | 5-Cl | H | C$_2$H$_5$ | CF$_3$ | |
| 1.421 | 2-OC$_2$H$_5$ | 5-Cl | H | C$_3$H$_7$(i) | CF$_3$ | |
| 1.422 | 2-OC$_2$H$_5$ | 5-Cl | H | Cyclopropyl | CF$_3$ | |
| 1.423 | 2-OC$_2$H$_5$ | 5-Cl | H | Phenyl | CF$_3$ | |
| 1.424 | 2-OC$_2$H$_5$ | 5-Cl | H | OCH$_3$ | CF$_3$ | |
| 1.425 | 2-OC$_2$H$_5$ | 5-Cl | H | CH$_3$ | CF$_2$CF$_3$ | |
| 1.426 | 2-OC$_3$H$_7$(i) | 5-Cl | H | CH$_3$ | Cl | |
| 1.427 | 2-OC$_3$H$_7$(i) | 5-Cl | H | CH$_3$ | CF$_3$ | |
| 1.428 | 2-OC$_3$H$_7$(i) | 5-Cl | H | CH$_3$ | CF$_2$Cl | |
| 1.429 | 2-OC$_3$H$_7$(i) | 5-Cl | H | C$_2$H$_5$ | CF$_3$ | |
| 1.430 | 2-OC$_3$H$_7$(i) | 5-Cl | H | C$_3$H$_7$(n) | CF$_3$ | |
| 1.431 | 2-OC$_3$H$_7$(i) | 5-Cl | H | CH$_3$ | CHF$_3$ | |
| 1.432 | 2-OC$_3$H$_7$(i) | 5-Cl | H | OCH$_3$ | CF$_3$ | |
| 1.433 | 2-OC$_3$H$_7$(i) | 5-Cl | H | SCH$_3$ | CF$_3$ | |
| 1.434 | 2-OCF$_3$ | H | H | CH$_3$ | Cl | |
| 1.435 | 2-OCF$_3$ | H | H | CH$_3$ | CF$_3$ | |
| 1.436 | 2-OCF$_3$ | H | H | CH$_3$ | CF$_2$Cl | |
| 1.437 | 2-OCF$_3$ | H | H | CH$_3$ | CHF$_2$ | |
| 1.438 | 2-OCF$_3$ | H | H | CH$_3$ | CHFCl | |
| 1.439 | 2-OCF$_3$ | H | H | C$_2$H$_5$ | CF$_3$ | |
| 1.440 | 2-OCF$_3$ | H | H | C$_3$H$_7$(i) | CF$_3$ | |
| 1.441 | 2-OCF$_3$ | H | H | C$_4$H$_9$(n) | CF$_3$ | |
| 1.442 | 2-OCF$_3$ | H | H | C$_4$H$_9$(t) | CF$_3$ | |
| 1.443 | 2-OCF$_3$ | 5-Cl | H | CH$_3$ | CF$_3$ | |
| 1.444 | 2-OCF$_3$ | 5-Cl | H | CH$_3$ | Cl | |
| 1.445 | 2-OCF$_3$ | 5-Cl | H | CH$_3$ | CF$_3$ | |
| 1.446 | 2-OCF$_3$ | 5-Cl | H | CH$_3$ | CF$_2$Cl | |
| 1.447 | 2-OCF$_3$ | 5-Cl | H | CH$_3$ | CHF$_2$ | |
| 1.448 | 2-OCF$_3$ | 5-Cl | H | CH$_3$ | CHCl$_2$ | |
| 1.449 | 2-OCF$_3$ | 5-Cl | H | CH$_3$ | CHFCl | |
| 1.450 | 2-OCF$_3$ | 5-Cl | H | CH$_3$ | CF$_2$CF$_3$ | |
| 1.451 | 2-OCF$_3$ | 5-Cl | H | C$_2$H$_5$ | CF$_2$CF$_3$ | |
| 1.452 | 2-OCF$_3$ | 5-Cl | H | C$_2$H$_5$ | CF$_3$ | |
| 1.453 | 2-OCF$_3$ | 5-Cl | H | C$_3$H$_7$(i) | CF$_3$ | |
| 1.454 | 2-OCF$_3$ | 5-Cl | H | Cyclopropyl | CF$_3$ | |

TABLE I-continued

Compounds of formula I

| Comp. No. | R¹ | R² | R³ | R⁴ | R⁵ | Physical data |
|---|---|---|---|---|---|---|
| 1.455 | 2-OCF$_3$ | 5-Cl | H | Phenyl | CF$_3$ | |
| 1.456 | 2-OCF$_3$ | 5-Cl | H | OC$_2$H$_5$ | CF$_3$ | |
| 1.457 | 2-OCF$_3$ | 5-Cl | H | SC$_2$H$_5$ | CF$_3$ | |
| 1.458 | 2-SCH$_3$ | H | H | CH$_3$ | Cl | |
| 1.459 | 2-SCH$_3$ | H | H | CH$_3$ | CF$_3$ | m.p. 156–157° C. |
| 1.460 | 2-SCH$_3$ | H | H | CH$_3$ | CHF$_2$ | |
| 1.461 | 2-SCH$_3$ | H | H | CH$_3$ | CF$_2$CF$_3$ | |
| 1.462 | 2-SCH$_3$ | H | H | C$_2$H$_5$ | CF$_3$ | |
| 1.463 | 2-SCH$_3$ | H | H | C$_3$H$_7$(i) | CF$_3$ | m.p. 170–171° C. |
| 1.464 | 2-SCH$_3$ | H | H | C$_4$H$_9$(n) | CF$_3$ | |
| 1.465 | 2-SCH$_3$ | H | H | C$_4$H$_9$(t) | CF$_3$ | |
| 1.466 | 2-SCH$_3$ | 5-Cl | H | CH$_3$ | Cl | |
| 1.467 | 2-SCH$_3$ | 5-Cl | H | CH$_3$ | CF$_3$ | m.p. 162–163° C. |
| 1.468 | 2-SCH$_3$ | 5-Cl | H | CH$_3$ | CF$_2$CF$_3$ | |
| 1.469 | 2-SCH$_3$ | 5-Cl | H | CH$_3$ | CF$_2$Cl | |
| 1.470 | 2-SCH$_3$ | 5-Cl | H | C$_2$H$_5$ | CF$_3$ | |
| 1.471 | 2-SOCH$_3$ | H | H | CH$_3$ | Cl | |
| 1.472 | 2-SOCH$_3$ | H | H | CH$_3$ | CF$_3$ | m.p. 80–82° C. |
| 1.473 | 2-SOCH$_3$ | H | H | CH$_3$ | CHF$_2$ | |
| 1.474 | 2-SOCH$_3$ | H | H | CH$_3$ | CF$_2$CF$_3$ | |
| 1.475 | 2-SOCH$_3$ | H | H | C$_2$H$_5$ | CF$_3$ | |
| 1.476 | 2-SOCH$_3$ | H | H | C$_3$H$_7$(i) | CF$_3$ | |
| 1.477 | 2-SOCH$_3$ | H | H | C$_4$H$_9$(n) | CF$_3$ | |
| 1.478 | 2-SOCH$_3$ | H | H | C$_4$H$_9$(t) | CF$_3$ | |
| 1.479 | 2-SO$_2$CH$_3$ | H | H | CH$_3$ | Cl | m.p. 164–165° C. |
| 1.480 | 2-SO$_2$CH$_3$ | H | H | CH$_3$ | CF$_3$ | m.p. 166–167° C. |
| 1.481 | 2-SO$_2$CH$_3$ | H | H | C$_2$H$_5$ | CF$_3$ | |
| 1.482 | 2-SO$_2$CH$_3$ | H | H | C$_3$H$_7$(n) | CF$_3$ | |
| 1.483 | 2-SO$_2$CH$_3$ | H | H | C$_3$H$_7$(i) | CF$_3$ | |
| 1.484 | 2-SO$_2$CH$_3$ | H | H | Cyclopropyl | CF$_3$ | |
| 1.485 | 2-SO$_2$CH$_3$ | H | H | C$_4$H$_9$(i) | CF$_3$ | |
| 1.486 | 2-SO$_2$CH$_3$ | H | H | CH$_3$ | CF$_2$CF$_3$ | |
| 1.487 | 2-SO$_2$CH$_3$ | H | H | C$_2$H$_5$ | CF$_2$CF$_3$ | |
| 1.488 | 2-SO$_2$CH$_3$ | H | H | C$_3$H$_7$(i) | CF$_2$CF$_3$ | |
| 1.489 | 2-SOCH$_3$ | 5-Cl | H | CH$_3$ | Cl | |
| 1.490 | 2-SOCH$_3$ | 5-Cl | H | CH$_3$ | CF$_3$ | m.p. 132–133° C. |
| 1.491 | 2-SOCH$_3$ | 5-Cl | H | C$_2$H$_5$ | CF$_3$ | |
| 1.492 | 2-SOCH$_3$ | 5-Cl | H | CH$_3$ | CF$_2$CF$_3$ | |
| 1.493 | 2-SOCH$_3$ | 5-Cl | H | C$_3$H$_7$(i) | CF$_3$ | |
| 1.494 | 2-SO$_2$CH$_3$ | 5-Cl | H | CH$_3$ | Cl | |
| 1.495 | 2-SO$_2$CH$_3$ | 5-Cl | H | CH$_3$ | CF$_3$ | m.p. 154–155° C. |
| 1.496 | 2-SO$_2$CH$_3$ | 5-Cl | H | C$_2$H$_5$ | CF$_3$ | |
| 1.497 | 2-SO$_2$CH$_3$ | 5-Cl | H | CH$_3$ | CF$_2$CF$_3$ | |
| 1.498 | 2-SO$_2$CH$_3$ | 5-Cl | H | C$_3$H$_7$(i) | CF$_3$ | |
| 1.499 | 2-F | 5-F | H | CH$_3$ | OCHF$_2$ | |
| 1.500 | 2-F | 5-F | H | CH$_3$ | Cl | |
| 1.501 | 2-F | 5-F | H | CH$_3$ | CF$_3$ | m.p. 152–153° C. |
| 1.502 | 2-F | 5-F | H | C$_2$H$_5$ | CF$_3$ | |
| 1.503 | 2-F | 5-F | H | C$_3$H$_7$(n) | CF$_3$ | |
| 1.504 | 2-F | 5-F | H | C$_3$H$_7$(i) | CF$_3$ | |
| 1.505 | 2-F | 5-F | H | Cyclopropyl | CF$_3$ | m.p. 174–175° C. |
| 1.506 | 2-F | 5-F | H | CH$_3$ | CF$_3$CF$_3$ | |
| 1.507 | 2-F | 5-F | H | CH$_3$ | CF$_2$CF$_2$CF$_3$ | |
| 1.508 | 2-F | 5-F | H | CH$_3$ | CF$_2$Cl | |
| 1.509 | 2-F | 5-F | H | CH$_3$ | CHF$_2$ | |
| 1.510 | 2-F | 5-F | H | CH$_3$ | CHClF | |
| 1.511 | 2-F | 5-F | H | C$_2$H$_5$ | CF$_2$Cl | |
| 1.512 | 2-F | 5-F | H | C$_3$H$_7$(i) | CF$_2$Cl | m.p. 161–162° C. |
| 1.513 | 2-F | 5-F | H | C$_4$H$_9$(n) | CF$_3$ | |
| 1.514 | 2-F | 5-F | H | C$_4$H$_9$(t) | CF$_3$ | m.p. 156–157° C. |
| 1.515 | 2-F | 5-F | H | C$_2$H$_5$ | CF$_2$CF$_3$ | |
| 1.516 | 2-F | 5-F | H | C$_3$H$_7$(i) | CF$_2$CF$_3$ | m.p. 150–151° C. |
| 1.517 | 2-F | 5-F | H | C$_3$H$_8$(n) | CF$_2$CF$_3$ | |
| 1.518 | 2-F | 5-F | H | CH$_3$ | CCl$_2$CF$_3$ | |
| 1.519 | 2-F | 5-F | H | CH$_3$ | CHCl$_2$ | |
| 1.520 | 2-F | 5-F | H | C$_2$H$_5$ | CHCl$_2$ | m.p. 144–145° C. |
| 1.521 | 2-F | 5-F | H | CH$_3$ | CCl$_2$CH$_3$ | |
| 1.522 | 2-F | 5-F | H | OCH$_3$ | CF$_3$ | |
| 1.523 | 2-F | 5-F | H | OC$_3$H$_7$(i) | CF$_3$ | |
| 1.524 | 2-F | 5-F | H | SCH$_3$ | CF$_3$ | |

TABLE I-continued

Compounds of formula I

| Comp. No. | R$^1$ | R$^2$ | R$^3$ | R$^4$ | R$^5$ | Physical data |
|---|---|---|---|---|---|---|
| 1.525 | 2-F | 5-F | H | SC$_3$H$_7$(i) | CF$_3$ | |
| 1.526 | 2-F | 6-F | H | CH$_3$ | Cl | |
| 1.527 | 2-F | 6-F | H | CH$_3$ | CF$_3$ | m.p. 177–178° C. |
| 1.528 | 2-F | 6-F | H | C$_2$H$_5$ | CF$_3$ | m.p. 151–153° C. |
| 1.529 | 2-F | 6-F | H | C$_3$H$_7$(n) | CF$_3$ | |
| 1.530 | 2-F | 6-F | H | C$_3$H$_7$(i) | | m.p. 158–159° C. |
| 1.531 | 2-F | 6-F | H | CH$_3$ | CF$_2$CF$_3$ | |
| 1.532 | 2-F | 6-F | H | C$_2$H$_5$ | CF$_2$CF$_3$ | m.p. 137–139° C. |
| 1.533 | 2-F | 6-F | H | CH$_3$ | CF$_2$Cl | m.p. 178–179° C. |
| 1.534 | 2-F | 6-F | H | CH$_3$ | CHF$_2$ | |
| 1.535 | 2-F | 6-F | H | CH$_3$ | CHClF | |
| 1.536 | 2-F | 6-F | H | OCH$_3$ | CF$_3$ | |
| 1.537 | 2-F | 6-F | H | SCH$_3$ | CF$_3$ | |
| 1.538 | 2-F | 6-Cl | H | CH$_3$ | Cl | |
| 1.539 | 2-F | 6-Cl | H | CH$_3$ | CH$_3$ | |
| 1.540 | 2-F | 6-Cl | H | CH$_3$ | CF$_3$ | m.p. 184–185° C. |
| 1.541 | 2-F | 6-Cl | H | C$_2$H$_5$ | CF$_3$ | |
| 1.542 | 2-F | 6-Cl | H | C$_3$H$_7$(i) | CF$_3$ | m.p. 146–147° C. |
| 1.543 | 2-F | 6-Cl | H | Cyclopropyl | CF$_3$ | m.p. 172–173° C. |
| 1.544 | 2-F | 6-Cl | H | CH$_3$ | CF$_2$CF$_3$ | |
| 1.545 | 2-F | 6-Cl | H | C$_3$H$_7$(i) | CF$_2$CF$_3$ | |
| 1.546 | 2-F | 6-Cl | H | CH$_3$ | CCl$_2$CF$_3$ | |
| 1.547 | 2-F | 6-Cl | H | CH$_3$ | CHCl$_2$ | |
| 1.548 | 2-F | 6-Cl | H | CH$_3$ | CHF$_2$ | |
| 1.549 | 2-F | 6-Cl | H | CH$_3$ | CHFCl | |
| 1.550 | 2-F | 6-Cl | H | CH$_3$ | CF$_2$Cl | |
| 1.551 | 2-F | 6-Cl | H | C$_3$H$_7$(i) | CF$_2$Cl | |
| 1.552 | 2-F | 6-Cl | H | OCH$_3$ | CF$_3$ | |
| 1.553 | 2-CN | H | H | CH$_3$ | CF$_3$ | m.p. 142–143° C. |
| 1.554 | 2-CN | H | H | C$_2$H$_5$ | CF$_3$ | |
| 1.555 | 2-CN | H | H | C$_3$H$_7$(i) | CF$_3$ | |
| 1.556 | 2-CN | H | H | CH$_3$ | CF$_2$CF$_3$ | |
| 1.557 | 2-CN | H | H | C$_2$H$_5$ | CF$_2$CF$_3$ | |
| 1.558 | 2-CN | H | H | C$_3$H$_7$(i) | CF$_2$CF$_3$ | |
| 1.559 | 2-CN | H | H | CH$_3$ | CHF$_2$ | |
| 1.560 | 2-CN | H | H | CH$_3$ | CF$_2$Cl | |
| 1.561 | 2-CN | H | H | OCH$_3$ | CF$_3$ | |
| 1.562 | 2-CN | H | H | OC$_2$H$_5$ | CF$_3$ | |
| 1.563 | 2-PO(OC$_2$H$_5$)$_2$ | H | H | CH$_3$ | CF$_3$ | m.p. 144–145° C. |
| 1.564 | 2-PO(OC$_2$H$_5$)$_2$ | H | H | C$_2$H$_5$ | CF$_3$ | |
| 1.565 | 2-PO(OC$_2$H$_5$)$_2$ | H | H | C$_3$H$_7$(i) | CF$_3$ | |
| 1.566 | 2-Cl | 5-Cl | H | SOCH$_3$ | CF$_3$ | |
| 1.567 | 2-Cl | 5-Cl | H | SO$_2$CH$_3$ | CF$_3$ | |
| 1.568 | 2-Cl | 6-Cl | H | SOCH$_3$ | CF$_3$ | |
| 1.569 | 2-Cl | 6-Cl | H | SO$_2$CH$_3$ | CF$_3$ | |
| 1.570 | 2-Cl | 6-Cl | H | SOCH$_3$ | CH$_3$ | |
| 1.571 | 2-Cl | 6-Cl | H | SO$_2$CH$_3$ | CH$_3$ | |
| 1.572 | 2-Cl | 6-Cl | H | CN | CH$_3$ | |
| 1.573 | 2-Cl | 6-Cl | H | CN | CF$_3$ | |
| 1.574 | 2-Cl | 6-Cl | H | CH=CCl$_2$ | Cl | |
| 1.575 | 2-Cl | 5-Cl | H | CH=CCl$_2$ | Cl | |
| 1.576 | 2-CF$_3$ | H | H | CH=CCl$_2$ | Cl | |
| 1.577 | 2-Cl | 6-Cl | H | CH$_2$OCH$_3$ | CF$_3$ | |
| 1.578 | 2-Cl | 6-Cl | H | CH$_2$OCH$_3$ | C$_2$F$_5$ | |
| 1.579 | 2-Cl | 5-Cl | H | CH$_2$OCH$_3$ | CF$_3$ | |
| 1.580 | 2-Cl | 5-Cl | H | CH$_2$OCH$_3$ | CF$_2$Cl | |
| 1.581 | 2-OCH$_3$ | 5-Cl | H | CH$_2$OCH$_3$ | CF$_3$ | |
| 1.582 | 2-OCH$_3$ | 5-Cl | H | CH$_2$OCH$_3$ | CF$_2$CF$_3$ | |
| 1.583 | 2-F | 5-F | H | CH$_2$OCH$_3$ | CF$_3$ | |
| 1.584 | 2-OCHF$_2$ | 5-Cl | H | CH$_2$OCH$_3$ | CF$_3$ | |
| 1.585 | 2-OCHF$_2$ | 5-Cl | H | CH$_2$OCH$_3$ | CF$_2$Cl | |
| 1.586 | 3-Br | H | H | CH$_3$ | Cl | m.p. 133–134° C. |
| 1.587 | 3-Br | H | H | CH$_3$ | CF$_3$ | |
| 1.588 | 2-Br | 5-Br | H | CH$_3$ | Cl | |
| 1.589 | 2-Br | 5-Br | H | CH$_3$ | CF$_3$ | m.p. 155–156° C. |
| 1.590 | 2-Br | 5-Br | H | OCH$_3$ | CF$_3$ | |
| 1.591 | 2-Br | 5-Br | H | C$_2$H$_5$ | CF$_3$ | |
| 1.592 | 2-Br | 5-Br | H | CH$_3$ | CF$_2$Cl | |
| 1.593 | 2-Br | 5-Br | H | CH$_3$ | CHF$_2$ | |

TABLE I-continued

Compounds of formula I

| Comp. No. | R¹ | R² | R³ | R⁴ | R⁵ | Physical data |
|---|---|---|---|---|---|---|
| 1.594 | 2-CF$_3$ | 5-Cl | H | CH$_3$ | CF$_3$ | m.p. 152–153° C. |
| 1.595 | 2-CF$_3$ | 5-Cl | H | CH$_3$ | Cl | m.p. 142–143° C. |
| 1.596 | 2-CF$_3$ | 5-Cl | H | C$_2$H$_5$ | CF$_3$ | |
| 1.597 | 2-CF$_3$ | 5-Cl | H | C$_3$H$_7$(i) | CF$_3$ | |
| 1.598 | 2-CF$_3$ | 5-Cl | H | Cyclopropyl | CF$_3$ | |
| 1.599 | 2-CF$_3$ | 5-Cl | H | CH$_3$ | CH$_2$Cl | |
| 1.600 | 2-CF$_3$ | 5-Cl | H | CH$_3$ | CHF$_2$ | |
| 1.601 | 2-CF$_3$ | 5-Cl | H | C$_2$H$_5$ | CF$_2$Cl | |
| 1.602 | 2-CF$_3$ | 5-Cl | H | C$_3$H$_7$(i) | CF$_2$Cl | |
| 1.603 | 2-CF$_3$ | 5-Cl | H | CH$_3$ | CF$_2$CF$_3$ | |
| 1.604 | 2-CF$_3$ | 5-Cl | H | OCH$_3$ | CF$_3$ | |
| 1.605 | 2-CF$_3$ | 5-Cl | H | SCH$_3$ | CF$_3$ | |
| 1.606 | 2-CF$_3$ | 5-Cl | H | SOCH$_3$ | CF$_3$ | |
| 1.607 | 2-CF$_3$ | 5-Cl | H | SO$_2$CH$_3$ | CH$_3$ | |
| 1.608 | 2-CH$_3$ | 3-CH$_3$ | H | CH$_3$ | Cl | |
| 1.609 | 2-CH$_3$ | 3-CH$_3$ | H | CH$_3$ | CF$_3$ | |
| 1.610 | 2-CH$_3$ | 5-CH$_3$ | H | CH$_3$ | Cl | |
| 1.611 | 2-CH$_3$ | 5-CH$_3$ | H | CH$_3$ | CF$_3$ | |
| 1.612 | 2-CH$_3$ | 6-CH$_3$ | H | CH$_3$ | Cl | |
| 1.613 | 2-CH$_3$ | 6-CH$_3$ | H | CH$_3$ | CF$_3$ | m.p. 160–161° C. |
| 1.614 | 2-CH$_3$ | 6-CH$_3$ | H | CH$_3$ | CF$_2$Cl | m.p. 169–170° C. |
| 1.615 | 2-CH$_3$ | 6-CH$_3$ | H | CH$_3$ | CH$_2$CF$_3$ | |
| 1.616 | 2-CH$_3$ | 6-CH$_3$ | H | OCH$_3$ | CF$_3$ | |
| 1.617 | 2-CH$_3$ | 6-CH$_3$ | H | SCH$_3$ | CF$_3$ | |
| 1.618 | 2-CH$_3$ | 6-C$_2$H$_5$ | H | CH$_3$ | Cl | |
| 1.619 | 2-CH$_3$ | 6-C$_2$H$_5$ | H | CH$_3$ | CF$_3$ | m.p. 140–144° C. |
| 1.620 | 2-CH$_3$ | 6-C$_2$H$_5$ | H | OCH$_3$ | CF$_3$ | |
| 1.621 | 2-CH$_3$ | 5-F | H | CH$_3$ | Cl | |
| 1.622 | 2-CH$_3$ | 5-F | H | CH$_3$ | CF$_3$ | m.p. 170–172° C. |
| 1.623 | 2-CH$_3$ | 5-F | H | CH$_3$ | CHF$_2$ | |
| 1.624 | 2-CH$_3$ | 5-F | H | CH$_3$ | CF$_2$Cl | |
| 1.625 | 2-CH$_3$ | 5-F | H | C$_2$H$_5$ | CF$_3$ | |
| 1.626 | 2-CH$_3$ | 5-F | H | C$_3$H$_7$(i) | CF$_3$ | |
| 1.627 | 2-CH$_3$ | 5-F | H | OCH$_3$ | CF$_3$ | |
| 1.628 | 2-CH$_3$ | 5-F | H | OC$_2$H$_5$ | CF$_3$ | |
| 1.629 | 2-Br | 6-Br | H | CH$_3$ | Cl | |
| 1.630 | 2-Br | 6-Br | H | CH$_3$ | CF$_3$ | |
| 1.631 | 2-Br | 6-Br | H | C$_2$H$_5$ | CF$_3$ | m.p. 157–158° C. |
| 1.632 | 2-Br | 6-Br | H | C$_3$H$_7$(i) | CF$_3$ | |
| 1.633 | 2-Br | 6-Br | H | Cyclopropyl | CF$_3$ | |
| 1.634 | 2-Br | 6-Br | H | CH$_3$ | CHCl$_2$ | |
| 1.635 | 2-Br | 6-Br | H | CH$_3$ | CF$_2$CF$_3$ | |
| 1.636 | 2-Br | H | H | C$_3$H$_7$(i) | CF$_2$CF$_3$ | m.p. 149–150° C. |
| 1.637 | 2-CF$_3$ | H | H | CH$_3$ | CHCl$_2$ | m.p. 161–162° C. |
| 1.638 | 2-OCHF$_2$ | H | H | CH$_3$ | CF$_3$ | m.p. 145–146° C. |
| 1.639 | 2-OCHF$_2$ | H | H | C$_3$H$_7$(i) | CF$_3$ | |
| 1.640 | 2-OCHF$_2$ | H | H | Cyclopropyl | CF$_3$ | m.p. 137–138° C. |
| 1.641 | 2-OCHF$_2$ | H | H | CH$_3$ | CHF$_2$ | |
| 1.642 | 2-OCHF$_2$ | H | H | CH$_3$ | CHFCl | |
| 1.643 | 2-CF$_3$ | H | H | CH$_3$ | CHF$_2$ | |
| 1.644 | 2-CF$_3$ | H | H | CH$_3$ | CF$_2$Cl | |
| 1.645 | 2-CF$_3$ | H | H | C$_3$H$_7$(i) | CF$_2$Cl | m.p. 140–141° C. |
| 1.646 | 2-CF$_3$ | H | H | Cyclopropyl | CF$_3$ | m.p. 169–170° C. |
| 1.647 | 2-CF$_3$ | H | H | 2-Thienyl | CF$_3$ | m.p. 170–171° C. |
| 1.648 | 2-Br | H | H | C$_4$H$_9$(n) | CF$_3$ | m.p. 144–145° C. |
| 1.649 | 2-Br | H | H | C$_3$H$_7$(i) | CF$_3$ | m.p. 169–170° C. |
| 1.650 | 2-Br | H | H | CH$_3$ | CHF$_2$ | |
| 1.651 | 2-Br | H | H | CH$_3$ | CF$_2$Cl | |
| 1.652 | 2-Br | H | H | Cyclopropyl | CF$_2$Cl | |
| 1.653 | 2-Br | H | H | C$_2$H$_5$ | CHF$_2$ | |
| 1.654 | 2-Cl | 6-CH$_3$ | H | CH$_3$ | CH$_3$ | m.p. 165–167° C. |
| 1.655 | 2-Cl | 6-Cl | H | CH$_3$ | CHF$_2$ | m.p. 182–183° C. |
| 1.656 | 2-Cl | 6-Cl | H | C$_2$H$_5$ | CHF$_2$ | |
| 1.657 | 2-Cl | 5-Cl | H | C$_5$H$_{11}$(n) | CF$_3$ | m.p. 118–119° C. |
| 1.658 | 2-COOCH$_3$ | H | H | CH$_3$ | CF$_3$ | m.p. 138–139° C. |
| 1.659 | 2-COOCH$_3$ | H | H | C$_2$H$_5$ | CF$_3$ | |
| 1.660 | 2-COOCH$_3$ | H | H | C$_3$H$_7$(i) | CF$_3$ | |
| 1.661 | 2-COOCH$_3$ | H | H | Cyclopropyl | CF$_3$ | |
| 1.662 | 2-COOCH$_3$ | H | H | CH$_3$ | CF$_2$Cl | |
| 1.663 | 2-COOCH$_3$ | H | H | CH$_3$ | CHF$_2$ | |

TABLE I-continued

Compounds of formula I

| Comp. No. | R¹ | R² | R³ | R⁴ | R⁵ | Physical data |
|---|---|---|---|---|---|---|
| 1.664 | 2-COOC$_2$H$_5$ | H | H | CH$_3$ | CF$_3$ | |
| 1.665 | 2-COOC$_3$H$_7$(n) | H | H | CH$_3$ | CF$_3$ | |
| 1.666 | 2-COOC$_3$H$_7$(i) | H | H | CH$_3$ | CF$_3$ | |
| 1.667 | 2-COOC$_4$H$_9$(n) | H | H | CH$_3$ | CF$_3$ | |
| 1.668 | 2-OCH$_3$ | 5-F | H | CH$_3$ | CF$_3$ | m.p. 141–142° C. |
| 1.669 | 2-OCH$_3$ | 5-F | H | CH$_3$ | CHF$_2$ | |
| 1.670 | 2-OCH$_3$ | 5-F | H | C$_2$H$_5$ | CHF$_2$ | |
| 1.671 | 2-OCH$_3$ | 5-F | H | C$_3$H$_7$(i) | CF$_3$ | |
| 1.672 | 2-OCH$_3$ | 5-F | H | Cyclopropyl | CF$_3$ | |
| 1.673 | 2-OCH$_3$ | 5-F | H | Cyclopropyl | CF$_3$Cl | |
| 1.674 | 2-OCHF$_2$ | 5-F | H | CH$_3$ | CF$_3$ | |
| 1.675 | 2-OCHF$_2$ | 5-F | H | CH$_3$ | CHF$_2$ | |
| 1.676 | 2-OCHF$_2$ | 5-F | H | CH$_3$ | CF$_2$Cl | |
| 1.677 | 2-COOCH$_3$ | 6-CH$_3$ | H | CH$_3$ | CF$_3$ | m.p. 161–162° C. |
| 1.678 | 2-COOCH$_3$ | 6-CH$_3$ | H | CH$_3$ | CHF$_2$ | |
| 1.679 | 2-COOCH$_3$ | 6-CH$_3$ | H | C$_3$H$_7$(i) | CF$_3$ | |
| 1.680 | 2-COOCH$_3$ | 6-CH$_3$ | H | Cyclopropyl | CF$_3$ | |
| 1.681 | 2-COOCH$_3$ | 6-Cl | H | CH$_3$ | CF$_3$ | m.p. 144–145° C. |
| 1.682 | 2-COOCH$_3$ | 6-Cl | H | CH$_3$ | CHF$_2$ | |
| 1.683 | 2-Br | H | H | 2-Furyl | CF$_3$ | m.p. 176–177° C. |
| 1.684 | 2-Cl | 6-Cl | 3-CH$_3$ | CH$_3$ | Cl | |
| 1.685 | 2-CF$_3$ | H | H | C$_2$H$_5$ | CHCl$_2$ | m.p. 155–156° C. |
| 1.686 | 2-Cl | 5-Cl | H | Cl | CF$_3$ | |
| 1.687 | 2-CONH$_2$ | H | H | CH$_3$ | CF$_3$ | |
| 1.688 | 2-Cl | 6-Cl | H | CH$_3$<br>\|<br>CHCH$_2$CH$_3$ | CF$_3$ | m.p. 124–125° C. |
| 1.689 | 2-F | H | H | C$_2$H$_5$ | CF$_3$ | m.p. 136–137° C. |
| 1.690 | 2-F | H | H | CH$_2$OCH$_3$ | CF$_3$ | m.p. 122–124° C. |
| 1.691 | 2-F | H | H | CH$_2$OCH$_3$ | CF$_2$Cl | m.p. 145–147° C. |
| 1.692 | 2-OCH$_3$ | 6-Cl | H | CH$_3$ | CF$_3$ | m.p. 191–192° C. |
| 1.693 | 2-OCH$_3$ | 6-Cl | H | C$_2$H$_5$ | CF$_3$ | m.p. 147–149° C. |
| 1.694 | 2-OCH$_3$ | 6-Cl | H | C$_3$H$_7$(i) | CF$_3$ | m.p. 143–146° C. |
| 1.695 | 2-CH$_3$ | 6-CH$_3$ | H | C$_2$H$_5$ | CF$_3$ | m.p. 158–160° C. |
| 1.696 | 2-CH$_3$ | 6-CH$_3$ | H | C$_3$H$_7$(i) | CF$_3$ | m.p. 143–146° C. |
| 1.697 | 2-F | 6-F | H | C$_4$H$_9$(i) | CF$_3$ | m.p. 135–137° C. |
| 1.698 | 2-F | 6-F | H | Cyclopropyl | CF$_3$ | m.p. 158–159° C. |
| 1.699 | 2-F | 6-F | H | CH$_2$OCH$_3$ | CF$_3$ | m.p. 138–139° C. |
| 1.700 | 2-F | 6-F | H | C$_2$H$_5$ | CHCl$_2$ | m.p. 169–171° C. |
| 1.701 | 2-F | 6-F | H | 2-Furyl | CF$_3$ | m.p. 152–153° C. |
| 1.702 | 2-CH$_3$ | 5-F | H | C$_2$H$_5$ | CHCl$_2$ | |
| 1.703 | 2-Cl | 6-CH$_3$ | H | CH$_2$OCH$_3$ | CF$_3$ | m.p. 137–138° C. |
| 1.704 | 2-Cl | 6-CH$_3$ | H | CH$_2$OCH$_3$ | CF$_2$Cl | m.p. 133–134° C. |
| 1.705 | 2-Cl | 6-CH$_3$ | H | C$_3$H$_7$(i) | CF$_2$Cl | m.p. 142–144° C. |
| 1.706 | 2-Cl | 6-CH$_3$ | H | Cl | CF$_3$ | |
| 1.707 | 2-Cl | 6-CH$_3$ | H | CH$_2$OCH$_3$ | CHF$_2$ | m.p. 142–144° C. |
| 1.708 | 2-F | H | H | CH$_2$OCH$_3$ | CHF$_2$ | m.p. 116–118° C. |
| 1.709 | 2-OCH$_3$ | 6-CH$_3$ | H | CH$_3$ | CF$_3$ | m.p. 180–181° C. |
| 1.710 | 2-Cl | 6-Cl | H | Cl | CF$_3$ | m.p. 189–190° C. |
| 1.711 | 2-SCHF$_2$ | H | H | CH$_3$ | CF$_3$ | |
| 1.712 | 2-OCHF$_2$ | 6-CH$_3$ | H | CH$_3$ | CF$_3$ | |
| 1.713 | 2-OCHF$_2$ | 6-CH$_3$ | C$_2$H$_5$ | CF$_3$ | | |
| 1.714 | 2-F | 6-Cl | H | 2-Furyl | CF$_3$ | |
| 1.715 | 2-CH$_3$ | 6-F | H | C$_2$H$_5$ | CHCl$_2$ | m.p. 141–142° C. |

P.2. Compounds of formula II

P. 2.1.
N-(4-methyl-6-trifluoromethyl-pyrimidin-2-yl)-2-tri-fluoromethylaniline

A suspension of 24 g (0.1 mole) of 2-trifluoromethylphenyl-guanidinium hydrochloride in 80 ml of tetrahydrofuran is added to a solution of 12 g (0.1 mole) of potassium tert.-butoxide in 100 ml of tetrahydrofuran. When the exothermic reaction has subsided, 15.4 g (0.1 mole) of α,α,α-trifluoroacetylacetone in 20 ml of tetrahydrofuran are added. The reaction mixture is stirred for 2 hours at 60° C., then concentrated by evaporation in a rotary evaporator. The residue is chromatographed on silica gel with a mixture of ethyl acetate and hexane (ratio 1:2). 18.7 g (58.2% of the theoretical amount) of the title compound of formula

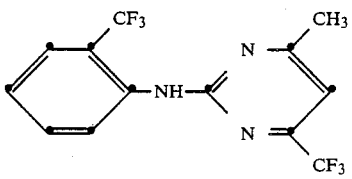

are obtained in the form of crystals having a melting point of 65°-66° C. (Comp. No. 2.020).

The compounds of Table II can be obtained analogously to Example P. 2:

TABLE II

Compounds of formula II

| Comp. No. | $R^1$ | $R^2$ | $R^3$ | $R^4$ | $R^5$ | Physical data |
|---|---|---|---|---|---|---|
| 2.001 | 2-Cl | H | H | $CH_3$ | $CH_3$ | |
| 2.002 | 2-Cl | H | H | $CH_3$ | $OCHF_2$ | |
| 2.003 | 2-Cl | H | H | $CH_3$ | Cl | |
| 2.004 | 2-Cl | H | H | $CH_3$ | $CF_3$ | |
| 2.005 | 2-Cl | H | H | $CH_3$ | $CF_2CF_3$ | |
| 2.006 | 2-Cl | H | H | $CH_2CH_3$ | $CF_3$ | |
| 2.007 | 2-Cl | H | H | $CH_3$ | $CF_2Cl$ | |
| 2.008 | 2-Cl | H | H | $CH_3$ | $CHF_2$ | |
| 2.009 | 2-Br | H | H | $CH_3$ | Cl | m.p. 109–110° C. |
| 2.010 | 2-Br | H | H | $OCH_3$ | $CF_3$ | |
| 2.011 | 2-Br | H | H | $CH_3$ | $CF_3$ | |
| 2.012 | 2-Br | H | H | $SCH_3$ | $CF_3$ | |
| 2.013 | 2-Br | H | H | $CH_2CH_3$ | $CF_3$ | |
| 2.014 | 2-Br | H | H | $CH_3$ | $CHCl_2$ | |
| 2.015 | 2-Br | H | H | $CH_3$ | $CHFCl$ | |
| 2.016 | 2-Br | H | H | Cyclopropyl | $CF_3$ | m.p. 85–86° C. |
| 2.017 | 2-$CF_3$ | H | H | Phenyl | $CF_3$ | |
| 2.018 | 2-$CF_3$ | H | H | 2-Furyl | $CF_3$ | |
| 2.019 | 2-$CF_3$ | H | H | $CH_3$ | Cl | |
| 2.020 | 2-$CF_3$ | H | H | $CH_3$ | $CF_3$ | m.p. 65–66° C. |
| 2.021 | 2-$CF_3$ | H | H | $CH_3$ | $CH_3$ | m.p. 70–72° C. |
| 2.022 | 2-$CF_3$ | H | H | $CH_2CH_3$ | $CF_3$ | |
| 2.023 | 2-$CF_3$ | H | H | $CH(CH_3)_2$ | $CF_3$ | $n_D^{25}$: 1.4960 |
| 2.024 | 2-$CF_3$ | H | H | $(n)C_3H_7$ | $CF_3$ | $n_D^{25}$: 1.4970 |
| 2.025 | 2-$CF_3$ | H | H | $OCH_3$ | $CF_3$ | |
| 2.026 | 2-$CF_3$ | H | H | $OC_2H_5$ | $CF_3$ | |
| 2.027 | 2-$CF_3$ | H | H | $SCH_3$ | $CF_3$ | |
| 2.028 | 2-$CF_3$ | H | H | $SCH(CH_3)_2$ | $CF_3$ | |
| 2.029 | 2-$CF_3$ | H | H | $CH_3$ | $CF_2CF_3$ | |
| 2.030 | 2-$CF_3$ | H | H | $CH_3$ | $CHFCl$ | |
| 2.031 | 2-J | H | H | $CH_3$ | Cl | |
| 2.032 | 2-J | H | H | $CH_3$ | $CF_3$ | m.p. 109–110° C. |
| 2.033 | 2-J | H | H | $CH_2CH_3$ | $CF_3$ | |
| 2.034 | 2-J | H | H | $CH_3$ | $CF_2Cl$ | |
| 2.035 | 2-F | H | H | $CH_3$ | $CH_3$ | |
| 2.036 | 2-F | H | H | $CH_3$ | Cl | |
| 2.037 | 2-F | H | H | $CH_3$ | $CF_3$ | m.p. 64–66° C. |
| 2.038 | 2-F | H | H | $CH(CH_3)_2$ | $CF_3$ | $n_D^{25}$: 1.5240 |
| 2.039 | 2-F | H | H | Cl | $CF_3$ | |
| 2.040 | 2-F | H | H | $OC_2H_5$ | $CF_3$ | |
| 2.041 | 2-Cl | 3-Cl | H | $CH_3$ | Cl | m.p. 123–124° C. |
| 2.042 | 2-Cl | 3-Cl | H | $CH_3$ | $CF_3$ | m.p. 109–110° C. |
| 2.043 | 2-Cl | 3-Cl | H | $OCH_3$ | $CF_3$ | |
| 2.044 | 2-Cl | 3-Cl | H | $OC_4H_9(n)$ | $CF_3$ | |
| 2.045 | 2-Cl | 3-Cl | H | $SC_2H_5$ | $CF_3$ | |
| 2.046 | 2-Cl | 3-Cl | H | Phenyl | $CF_3$ | |
| 2.047 | 2-Cl | 3-Cl | H | $CH_3$ | $CF_2Cl$ | |
| 2.048 | 2-Cl | 3-Cl | H | $CH_3$ | $CHFCl$ | |
| 2.049 | 2-Cl | 3-Cl | H | $CH_3$ | $CH_3$ | |
| 2.050 | 2-Cl | 5-Cl | H | $CH_3$ | $CH_3$ | |
| 2.051 | 2-Cl | 5-Cl | H | $CH_3$ | $OCHF_2$ | |
| 2.052 | 2-Cl | 5-Cl | H | $CH_3$ | Cl | m.p. 99–100° C. |
| 2.053 | 2-Cl | 5-Cl | H | $OCH_3$ | $CH_3$ | |

TABLE II-continued

Compounds of formula II

| Comp. No. | R¹ | R² | R³ | R⁴ | R⁵ | Physical data |
|---|---|---|---|---|---|---|
| 2.054 | 2-Cl | 5-Cl | H | $CH_3$ | Br | |
| 2.055 | 2-Cl | 5-Cl | H | $CH_3$ | $CF_3$ | m.p. 79-80° C. |
| 2.056 | 2-Cl | 5-Cl | H | $CH_2CH_3$ | $CF_3$ | m.p. 62-63° C. |
| 2.057 | 2-Cl | 5-Cl | H | $C_3H_7(n)$ | $CF_3$ | $n_D^{25}$: 1,5490 |
| 2.058 | 2-Cl | 5-Cl | H | $C_3H_7(i)$ | $CF_3$ | m.p. 60-61° C. |
| 2.059 | 2-Cl | 5-Cl | H | Cyclopropyl | $CF_3$ | m.p. 106-107° C. |
| 2.060 | 2-Cl | 5-Cl | H | Phenyl | $CF_3$ | |
| 2.061 | 2-Cl | 5-Cl | H | 2-Thienyl | $CF_3$ | m.p. 112-113° C. |
| 2.062 | 2-Cl | 5-Cl | H | 2-Furyl | $CF_3$ | m.p. 102-103° C. |
| 2.063 | 2-Cl | 5-Cl | H | $CH_3$ | $CF_2CF_3$ | m.p. 99-100° C. |
| 2.064 | 2-Cl | 5-Cl | H | $CH_3$ | $CF_2Cl$ | m.p. 67° C. |
| 2.065 | 2-Cl | 5-Cl | H | $CH_3$ | $CHF_2$ | m.p. 72-74° C. |
| 2.066 | 2-Cl | 5-Cl | H | $CH_3$ | $CHClF$ | m.p. 66-67° C. |
| 2.067 | 2-Cl | 5-Cl | H | $CH_2CH_3$ | $CF_2Cl$ | |
| 2.068 | 2-Cl | 5-Cl | H | $C_3H_7(i)$ | $CF_2Cl$ | $n_D^{25}$: 1,5682 |
| 2.069 | 2-Cl | 5-Cl | H | $OCH_3$ | $CF_3$ | |
| 2.070 | 2-Cl | 5-Cl | H | $OC_2H_5$ | $CF_3$ | |
| 2.071 | 2-Cl | 5-Cl | H | $OC_3H_7$ | $CF_3$ | |
| 2.072 | 2-Cl | 5-Cl | H | $OC_3H_7(i)$ | $CF_3$ | |
| 2.073 | 2-Cl | 5-Cl | H | $OC_4H_9(n)$ | $CF_3$ | |
| 2.074 | 2-Cl | 5-Cl | H | $OC_4H_9(i)$ | $CF_3$ | |
| 2.075 | 2-Cl | 5-Cl | H | $SCH_3$ | $CF_3$ | |
| 2.076 | 2-Cl | 5-Cl | H | $SC_2H_5$ | $CF_3$ | |
| 2.077 | 2-Cl | 5-Cl | H | $SC_3H_7(n)$ | $CF_3$ | |
| 2.078 | 2-Cl | 5-Cl | H | $SC_3H_7(i)$ | $CF_3$ | |
| 2.079 | 2-Cl | 5-Cl | H | $SC_4H_9(n)$ | $CF_3$ | |
| 2.080 | 2-Cl | 5-Cl | H | $C_4H_9(n)$ | $CF_3$ | $n_D^{25}$: 1,5475 |
| 2.081 | 2-Cl | 5-Cl | H | $C_4H_9(i)$ | $CF_3$ | |
| 2.082 | 2-Cl | 5-Cl | H | $C_4H_9(t)$ | $CF_3$ | m.p. 106-107° C. |
| 2.083 | 2-Cl | 5-Cl | H | $C_2H_5$ | $CF_2CF_3$ | m.p. 70-72° C. |
| 2.084 | 2-Cl | 5-Cl | H | $C_3H_7(i)$ | $CF_2CF_3$ | m.p. 39-41° C. |
| 2.085 | 2-Cl | 5-Cl | H | $C_3H_7(n)$ | $CF_2CF_3$ | |
| 2.086 | 2-Cl | 5-Cl | H | $OCF_2CHF_2$ | $CF_3$ | |
| 2.087 | 2-Cl | 5-Cl | H | $CH_3$ | $CCl_2CF_3$ | |
| 2.088 | 2-Cl | 5-Cl | H | $C_2H_5$ | $CCl_2CF_3$ | |
| 2.089 | 2-Cl | 5-Cl | H | $CH_3$ | $CHCl_2$ | m.p. 80-82° C. |
| 2.090 | 2-Cl | 5-Cl | H | $C_2H_5$ | $CHCl_2$ | $n_D^{25}$: 1,6115 |
| 2.091 | 2-Cl | 5-Cl | H | $CH_3$ | $CCl_2CH_3$ | |
| 2.092 | 2-Cl | 5-Cl | H | $C_2H_5$ | $CCl_2CH_3$ | |
| 2.093 | 2-Cl | 6-Cl | H | $CH_3$ | $CH_3$ | m.p. 185-186° C. |
| 2.094 | 2-Cl | 6-Cl | H | $CH_3$ | $C_2H_5$ | |
| 2.095 | 2-Cl | 6-Cl | H | $CH_3$ | $C_3H_7(i)$ | |
| 2.096 | 2-Cl | 6-Cl | H | $CH_3$ | Cl | m.p. 190-191° C. |
| 2.097 | 2-Cl | 6-Cl | H | $CH_3$ | $CCl_2CH_3$ | |
| 2.098 | 2-Cl | 6-Cl | H | $C_2H_5$ | $CCl_2CH_3$ | |
| 2.099 | 2-Cl | 6-Cl | H | $CH_3$ | $CHCl_2$ | |
| 2.100 | 2-Cl | 6-Cl | H | $C_2H_5$ | $CHCl_2$ | |
| 2.101 | 2-Cl | 6-Cl | H | $CH_3$ | $CCl_2CF_3$ | |
| 2.102 | 2-Cl | 6-Cl | H | $C_3H_7(i)$ | $CCl_2CF_3$ | |
| 2.103 | 2-Cl | 6-Cl | H | $CH_3$ | $CHClF$ | |
| 2.104 | 2-Cl | 6-Cl | H | $C_2H_5$ | $CHClF$ | |
| 2.105 | 2-Cl | 6-Cl | H | $CH_3$ | $CF_2Cl$ | |
| 2.106 | 2-Cl | 6-Cl | H | $C_2H_5$ | $CF_2Cl$ | |
| 2.107 | 2-Cl | 6-Cl | H | $C_3H_7(i)$ | $CF_2Cl$ | |
| 2.108 | 2-Cl | 6-Cl | H | $C_3H_7(n)$ | $CF_2Cl$ | |
| 2.109 | 2-Cl | 6-Cl | H | $CH_3$ | $CF_3$ | m.p. 138-139° C. |
| 2.110 | 2-Cl | 6-Cl | H | $C_2H_5$ | $CF_3$ | |
| 2.111 | 2-Cl | 6-Cl | H | $C_3H_7(n)$ | $CF_3$ | |
| 2.112 | 2-Cl | 6-Cl | H | $C_3H_7(i)$ | $CF_3$ | |
| 2.113 | 2-Cl | 6-Cl | H | Cyclopropyl | $CF_3$ | m.p. 70-73° C. |
| 2.114 | 2-Cl | 6-Cl | H | Phenyl | $CF_3$ | |
| 2.115 | 2-Cl | 6-Cl | H | 2-Thienyl | $CF_3$ | m.p. 119-120° C. |
| 2.116 | 2-Cl | 6-Cl | H | 2-Furyl | $CF_3$ | |
| 2.117 | 2-Cl | 6-Cl | H | $CH_3$ | $CF_2CF_3$ | |
| 2.118 | 2-Cl | 6-Cl | H | $C_2H_5$ | $CF_2CF_3$ | m.p. 96-98° C. |
| 2.119 | 2-Cl | 6-Cl | H | $C_3H_7(i)$ | $CF_2CF_3$ | m.p. 88-90° C. |
| 2.120 | 2-Cl | 6-Cl | H | $C_3H_7(n)$ | $CF_2CF_3$ | |
| 2.121 | 2-Cl | 6-Cl | H | Cyclopropyl | $CF_2CF_3$ | |

TABLE II-continued

Compounds of formula II $$\text{H-C}_6\text{H}_2(R^1)(R^2)(R^3)\text{-NH-C(CH}_3\text{)=N-N=C(R^4)(R^5)}$$

| Comp. No. | $R^1$ | $R^2$ | $R^3$ | $R^4$ | $R^5$ | Physical data |
|---|---|---|---|---|---|---|
| 2.122 | 2-Cl | 6-Cl | H | $CH_3$ | $OCHF_2$ | |
| 2.123 | 2-Cl | 6-Cl | H | $C_4H_9(n)$ | $CF_3$ | |
| 2.124 | 2-Cl | 6-Cl | H | $C_4H_9(i)$ | $CF_3$ | |
| 2.125 | 2-Cl | 6-Cl | H | $C_4H_9(t)$ | $CF_3$ | m.p. 79–81° C. |
| 2.126 | 2-Cl | 6-Cl | H | $OCH_3$ | $CF_3$ | |
| 2.127 | 2-Cl | 6-Cl | H | $OC_2H_5$ | $CF_3$ | |
| 2.128 | 2-Cl | 6-Cl | H | $OC_3H_7(n)$ | $CF_3$ | |
| 2.129 | 2-Cl | 6-Cl | H | $OC_3H_7(i)$ | $CF_3$ | |
| 2.130 | 2-Cl | 6-Cl | H | $OC_4H_9(n)$ | $CF_3$ | |
| 2.131 | 2-Cl | 6-Cl | H | $OC_4H_9(i)$ | $CF_3$ | |
| 2.132 | 2-Cl | 6-Cl | H | $SCH_3$ | $CF_3$ | m.p. 70–71° C. |
| 2.133 | 2-Cl | 6-Cl | H | $SC_2H_5$ | $CF_3$ | |
| 2.134 | 2-Cl | 6-Cl | H | $SC_3H_7(n)$ | $CF_3$ | |
| 2.135 | 2-Cl | 6-Cl | H | $SC_3H_7(i)$ | $CF_3$ | |
| 2.136 | 2-Cl | 6-Cl | H | $SC_4H_9(n)$ | $CF_3$ | |
| 2.137 | 2-Cl | 6-Cl | H | $OCH_3$ | $CH_3$ | |
| 2.138 | 2-Cl | 6-Cl | H | $C_2H_5$ | Cl | |
| 2.139 | 2-Cl | 6-Cl | H | $OCH_3$ | $C_2H_5$ | |
| 2.140 | 2-Cl | 6-Cl | H | $C_2H_5$ | $OCHF_2$ | |
| 2.141 | 2-Cl | 6-Cl | 3-$CH_3$ | $CH_3$ | $CF_3$ | m.p. 124–125° C. |
| 2.142 | 2-Cl | 6-Cl | 3-$CH_3$ | $C_2H_5$ | $CF_3$ | m.p. 90–91° C. |
| 2.143 | 2-Cl | 6-Cl | 3-$CH_3$ | $C_3H_7(n)$ | $CF_3$ | |
| 2.144 | 2-Cl | 6-Cl | 3-$CH_3$ | $C_3H_7(i)$ | $CF_3$ | m.p. 74–75° C. |
| 2.145 | 2-Cl | 6-Cl | 3-$CH_3$ | $CH_3$ | $CF_2CF_3$ | m.p. 119–121° C. |
| 2.146 | 2-Cl | 6-Cl | 3-$CH_3$ | $C_2H_5$ | $CF_2CF_3$ | |
| 2.147 | 2-Cl | 6-Cl | 3-$CH_3$ | Cl | $CF_3$ | |
| 2.148 | 2-Cl | 6-Cl | 3-$CH_3$ | $OCH_3$ | $CF_3$ | |
| 2.149 | 2-Cl | 6-Cl | 3-$CH_3$ | $OC_2H_5$ | $CF_3$ | |
| 2.150 | 2-Cl | 6-Cl | 3-$CH_3$ | $SCH_3$ | $CF_3$ | |
| 2.151 | 2-Cl | 6-Cl | 3-$CH_3$ | $SC_4H_9(n)$ | $CF_3$ | |
| 2.152 | 2-Cl | 6-Cl | 3-$CH_3$ | $CH_3$ | $CF_2Cl$ | |
| 2.153 | 2-Cl | 6-Cl | 3-$CH_3$ | $CH_3$ | $CHF_2$ | |
| 2.154 | 2-Cl | 6-Cl | 3-$CH_3$ | $CH_3$ | $CHCl_2$ | |
| 2.155 | 2-Cl | 3-$CF_3$ | H | $CH_3$ | Cl | |
| 2.156 | 2-Cl | 3-$CF_3$ | H | $CH_3$ | $CH_3$ | |
| 2.157 | 2-Cl | 3-$CF_3$ | H | $CH_3$ | $CF_3$ | |
| 2.158 | 2-Cl | 3-$CF_3$ | H | $C_2H_5$ | $CF_3$ | |
| 2.159 | 2-Cl | 3-$CF_3$ | H | $C_3H_7(n)$ | $CF_3$ | |
| 2.160 | 2-Cl | 3-$CF_3$ | H | $CH_3$ | $CF_2CF_3$ | |
| 2.161 | 2-Cl | 3-$CF_3$ | H | $CH_3$ | $CClF_2$ | |
| 2.162 | 2-Cl | 3-$CF_3$ | H | $CH_3$ | $CHClF$ | |
| 2.163 | 2-Cl | 5-$CF_3$ | H | $CH_3$ | Cl | m.p. 101–103° C. |
| 2.164 | 2-Cl | 5-$CF_3$ | H | $CH_3$ | $CF_3$ | m.p. 84–85° C. |
| 2.165 | 2-Cl | 5-$CF_3$ | H | $CH_3$ | $CClF_2$ | |
| 2.166 | 2-Cl | 5-$CF_3$ | H | $C_2H_5$ | $CF_3$ | |
| 2.167 | 2-Cl | 5-$CF_3$ | H | $OCH_3$ | $CF_3$ | |
| 2.168 | 2-Cl | 6-$CF_3$ | H | $CH_3$ | Cl | |
| 2.169 | 2-Cl | 6-$CF_3$ | H | $CH_3$ | $CH_3$ | |
| 2.170 | 2-Cl | 6-$CF_3$ | H | $CH_3$ | $CF_3$ | m.p. 117–119° C. |
| 2.171 | 2-Cl | 6-$CF_3$ | H | $C_2H_5$ | $CF_3$ | |
| 2.172 | 2-Cl | 6-$CF_3$ | H | $C_3H_7(n)$ | $CF_3$ | |
| 2.173 | 2-Cl | 6-$CF_3$ | H | $C_3H_7(i)$ | $CF_3$ | |
| 2.174 | 2-Cl | 6-$CF_3$ | H | Cyclopropyl | $CF_3$ | |
| 2.175 | 2-Cl | 6-$CF_3$ | H | $C_4H_9(n)$ | $CF_3$ | |
| 2.176 | 2-Cl | 6-$CF_3$ | H | $C_4H_9(i)$ | $CF_3$ | |
| 2.177 | 2-Cl | 6-$CF_3$ | H | $C_4H_9(t)$ | $CF_3$ | |
| 2.178 | 2-Cl | 6-$CF_3$ | H | $CH_3$ | $CF_2CF_3$ | |
| 2.179 | 2-Cl | 6-$CF_3$ | H | $C_2H_5$ | $CF_2CF_3$ | |
| 2.180 | 2-Cl | 6-$CF_3$ | H | $CH_3$ | $CHCl_2$ | |
| 2.181 | 2-Cl | 6-$CF_3$ | H | $CH_3$ | $CClF_2$ | |
| 2.182 | 2-Cl | 6-$CF_3$ | H | $C_2H_5$ | $CClF_2$ | |
| 2.183 | 2-Cl | 6-$CF_3$ | H | $CH_3$ | $CHF_2$ | |
| 2.184 | 2-Cl | 6-$CF_3$ | H | $CH_3$ | $OCHF_2$ | |
| 2.185 | 2-Cl | 6-$CF_3$ | H | $OCH_3$ | $CF_3$ | |
| 2.186 | 2-Cl | 6-$CF_3$ | H | $OC_2H_5$ | $CF_3$ | |
| 2.187 | 2-Cl | 6-$CF_3$ | H | $SC_2H_5$ | $CF_3$ | |
| 2.188 | 2-Cl | 6-$CF_3$ | H | $CH_3$ | $CCl_2CF_3$ | |
| 2.189 | 2-Cl | 6-$CF_3$ | H | $CH_3$ | $CCl_2CH_3$ | |
| 2.190 | 2-Cl | 6-$CF_3$ | H | Phenyl | $CF_3$ | |
| 2.191 | 2-Cl | 3-$CH_3$ | H | $CH_3$ | $CF_3$ | |

TABLE II-continued

Compounds of formula II

| Comp. No. | R¹ | R² | R³ | R⁴ | R⁵ | Physical data |
|---|---|---|---|---|---|---|
| 2.192 | 2-Cl | 3-CH₃ | H | CH₃ | CF₂CF₃ | |
| 2.193 | 2-Cl | 3-CH₃ | H | C₂H₅ | CF₃ | |
| 2.194 | 2-Cl | 3-CH₃ | H | C₃H₇(n) | CF₃ | |
| 2.195 | 2-Cl | 3-CH₃ | H | C₃H₇(i) | CF₃ | |
| 2.196 | 2-Cl | 3-CH₃ | H | CH₃ | Cl | |
| 2.197 | 2-Cl | 3-CH₃ | H | CH₃ | CF₂Cl | |
| 2.198 | 2-Cl | 3-CH₃ | H | CH₃ | CHCl₂ | |
| 2.199 | 2-Cl | 3-CH₃ | H | CH₃ | CHClF | |
| 2.200 | 2-Cl | 3-CH₃ | H | OCH₃ | CF₃ | |
| 2.201 | 2-Cl | 5-CH₃ | H | CH₃ | Cl | m.p. 77–78° C. |
| 2.202 | 2-Cl | 5-CH₃ | H | CH₃ | CHCl₂ | |
| 2.203 | 2-Cl | 5-CH₃ | H | CH₃ | CCl₂CF₃ | |
| 2.204 | 2-Cl | 5-CH₃ | H | CH₃ | CHClF | |
| 2.205 | 2-Cl | 5-CH₃ | H | CH₃ | CF₂Cl | |
| 2.206 | 2-Cl | 5-CH₃ | H | C₂H₅ | CF₂Cl | |
| 2.207 | 2-Cl | 5-CH₃ | H | CH₃ | CF₃ | |
| 2.208 | 2-Cl | 5-CH₃ | H | C₂H₅ | CF₃ | |
| 2.209 | 2-Cl | 5-CH₃ | H | C₃H₇(n) | CF₃ | |
| 2.210 | 2-Cl | 5-CH₃ | H | C₃H₇(i) | CF₃ | |
| 2.211 | 2-Cl | 5-CH₃ | H | C₄H₉(n) | CF₃ | |
| 2.212 | 2-Cl | 5-CH₃ | H | C₄H₉(t) | CF₃ | |
| 2.213 | 2-Cl | 5-CH₃ | H | 2-Furyl | CF₃ | |
| 2.214 | 2-Cl | 5-CH₃ | H | CH₃ | CF₂CF₃ | |
| 2.215 | 2-Cl | 5-CH₃ | H | C₂H₅ | CF₂CF₃ | |
| 2.216 | 2-Cl | 5-CH₃ | H | OCH₃ | CF₃ | |
| 2.217 | 2-Cl | 5-CH₃ | H | OC₂H₅ | CF₃ | |
| 2.218 | 2-Cl | 5-CH₃ | H | SCH₃ | CF₃ | |
| 2.219 | 2-Cl | 6-CH₃ | H | CH₃ | Cl | m.p. 142–143° C. |
| 2.220 | 2-Cl | 6-CH₃ | H | CN | CH₃ | |
| 2.221 | 2-Cl | 6-CH₃ | H | CH₃ | CF₃ | m.p. 143–144° C. |
| 2.222 | 2-Cl | 6-CH₃ | H | CH₃ | CF₂Cl | m.p. 158–162° C. |
| 2.223 | 2-Cl | 6-CH₃ | H | CH₃ | CF₂CF₃ | |
| 2.224 | 2-Cl | 6-CH₃ | H | CH₃ | CCl₂CF₃ | |
| 2.225 | 2-Cl | 6-CH₃ | H | CH₃ | CHF₂ | |
| 2.226 | 2-Cl | 6-CH₃ | H | CH₃ | CHCl₂ | |
| 2.227 | 2-Cl | 6-CH₃ | H | C₂H₅ | CF₃ | m.p. 99–102° C. |
| 2.228 | 2-Cl | 6-CH₃ | H | C₃H₇(i) | CF₃ | m.p. 56–59° C. |
| 2.229 | 2-Cl | 6-CH₃ | H | Cyclopropyl | CF₃ | m.p. 75–77° C. |
| 2.230 | 2-Cl | 6-CH₃ | H | C₄H₉(i) | CF₃ | |
| 2.231 | 2-Cl | 6-CH₃ | H | C₂H₅ | CF₂CF₃ | m.p. 89–91° C. |
| 2.232 | 2-Cl | 6-CH₃ | H | OCH₃ | CF₃ | |
| 2.233 | 2-Cl | 6-CH₃ | H | OCH₂CH₂Cl | CF₃ | |
| 2.234 | 2-Cl | 6-CH₃ | H | OCH₂CH₂OCH₃ | CF₃ | |
| 2.235 | 2-Cl | 6-CH₃ | H | OC₂H₅ | CF₃ | |
| 2.236 | 2-Cl | 6-CH₃ | H | SCH₃ | CF₃ | |
| 2.237 | 2-Cl | 6-CH₃ | H | SC₂H₅ | CF₃ | |
| 2.238 | 2-Cl | 6-CH₃ | H | SC₃H₇(i) | CF₃ | |
| 2.239 | 2-Cl | 6-CH₃ | H | SC₄H₉(i) | CF₃ | |
| 2.240 | 2-Cl | 5-OCH₃ | H | CH₃ | CF₃ | |
| 2.241 | 2-Cl | 5-OCH₃ | H | C₂H₅ | CF₃ | |
| 2.242 | 2-Cl | 5-OCH₃ | H | CH₃ | Cl | |
| 2.243 | 2-Cl | 5-OCH₃ | H | OCH₃ | CF₃ | |
| 2.244 | 2-Cl | 5-OCH₃ | H | CH₃ | CHF₂ | |
| 2.245 | 2-Cl | 5-OCH₃ | H | CH₃ | CF₂CF₃ | |
| 2.246 | 2-Cl | 5-OCH₃ | H | CH₃ | CF₂Cl | |
| 2.247 | 2-Cl | 5-COOH₃ | H | CH₃ | CF₃ | m.p. 88–89° C. |
| 2.248 | 2-Cl | 5-COOH₃ | H | C₂H₅ | CF₃ | |
| 2.249 | 2-Cl | 5-COOC₂H₅ | H | CH₃ | CF₃ | |
| 2.250 | 2-Cl | 5-COOC₂H₅ | H | CH₃ | CF₂CF₃ | |
| 2.251 | 2-Cl | 5-COOC₃H₇(i) | H | CH₃ | CF₃ | |
| 2.252 | 2-Cl | 5-COOC₃H₇(i) | H | C₃H₇(i) | CF₃ | |
| 2.253 | 2-Cl | 5-COOC₃H₇(i) | H | CH₃ | CF₂Cl | |
| 2.254 | 2-Cl | 5-COOC₃H₇(i) | H | Phenyl | CF₃ | |
| 2.255 | 2-Cl | 5-COOC₃H₇(i) | H | Cyclopropyl | CF₃ | |
| 2.256 | 2-Cl | 5-COOC₃H₇(i) | H | CH₃ | CHFCl | |
| 2.257 | 3-Cl | 5-Cl | H | CH₃ | Cl | m.p. 152–153° C. |
| 2.258 | 3-Cl | 5-Cl | H | CH₃ | CF₃ | m.p. 93–94° C. |
| 2.259 | 3-Cl | 5-Cl | H | C₂H₅ | CF₃ | |
| 2.260 | 3-Cl | 5-Cl | H | C₃H₇(n) | CF₃ | |

TABLE II-continued

Compounds of formula II

| Comp. No. | R¹ | R² | R³ | R⁴ | R⁵ | Physical data |
|---|---|---|---|---|---|---|
| 2.261 | 3-Cl | 5-Cl | H | $C_3H_7(i)$ | $CF_3$ | |
| 2.262 | 3-Cl | 5-Cl | H | Cyclopropyl | $CF_3$ | |
| 2.263 | 3-Cl | 5-Cl | H | Phenyl | $CF_3$ | |
| 2.264 | 3-Cl | 5-Cl | H | $CH_3$ | $CHF_2$ | |
| 2.265 | 3-Cl | 5-Cl | H | $CH_3$ | $CF_2Cl$ | |
| 2.266 | 3-Cl | 5-Cl | H | $C_2H_5$ | $CF_2Cl$ | |
| 2.267 | 3-Cl | 5-Cl | H | $OCH_3$ | $CF_3$ | |
| 2.268 | 3-Cl | 5-Cl | H | $OC_2H_5$ | $CF_3$ | |
| 2.269 | 3-Cl | 5-Cl | H | $SCH_3$ | $CF_3$ | |
| 2.270 | 3-Cl | 5-Cl | H | $SC_3H_7(i)$ | $CF_3$ | |
| 2.271 | 2-$CH_3$ | 5-Cl | H | $CH_3$ | Cl | m.p. 118–119° C. |
| 2.272 | 2-$CH_3$ | 5-Cl | H | $CH_3$ | $CF_3$ | |
| 2.273 | 2-$CH_3$ | 5-Cl | H | CN | $CF_3$ | |
| 2.274 | 2-$CH_3$ | 5-Cl | H | $C_2H_5$ | Cl | |
| 2.275 | 2-$CH_3$ | 5-Cl | H | $CH_3$ | $OCHF_2$ | |
| 2.276 | 2-$CH_3$ | 5-Cl | H | $CH_3$ | Br | |
| 2.277 | 2-$CH_3$ | 5-Cl | H | $CH_3$ | F | |
| 2.278 | 2-$CH_3$ | 5-Cl | H | $CH_3$ | $CH_3$ | m.p. 121–122° C. |
| 2.279 | 2-$CH_3$ | 5-Cl | H | $OCH_3$ | $CH_3$ | |
| 2.280 | 2-$CH_3$ | 5-Cl | H | $C_2H_5$ | $CF_3$ | |
| 2.281 | 2-$CH_3$ | 5-Cl | H | $C_3H_7(n)$ | $CF_3$ | |
| 2.282 | 2-$CH_3$ | 5-Cl | H | $C_3H_7(i)$ | $CF_3$ | |
| 2.283 | 2-$CH_3$ | 5-Cl | H | Cyclopropyl | $CF_3$ | |
| 2.284 | 2-$CH_3$ | 5-Cl | H | Phenyl | $CF_3$ | |
| 2.285 | 2-$CH_3$ | 5-Cl | H | $C_4H_9(n)$ | $CF_3$ | |
| 2.286 | 2-$CH_3$ | 5-Cl | H | $C_4H_9(i)$ | $CF_3$ | |
| 2.287 | 2-$CH_3$ | 5-Cl | H | $C_4H_9(t)$ | $CF_3$ | |
| 2.288 | 2-$CH_3$ | 5-Cl | H | $CH_3$ | $CF_2CF_3$ | |
| 2.289 | 2-$CH_3$ | 5-Cl | H | $C_2H_5$ | $CF_2CF_3$ | |
| 2.290 | 2-$CH_3$ | 5-Cl | H | $C_3H_7(i)$ | $CF_2CF_3$ | |
| 2.291 | 2-$CH_3$ | 5-Cl | H | $CH_3$ | $CF_2Cl$ | |
| 2.292 | 2-$CH_3$ | 5-Cl | H | $C_2H_5$ | $CF_2Cl$ | |
| 2.293 | 2-$CH_3$ | 5-Cl | H | $CH_3$ | $CHF_2$ | |
| 2.294 | 2-$CH_3$ | 5-Cl | H | $C_2H_5$ | $CHF_2$ | |
| 2.295 | 2-$CH_3$ | 5-Cl | H | $CH_3$ | $CHFCl$ | |
| 2.296 | 2-$CH_3$ | 5-Cl | H | $C_2H_5$ | $CHFCl$ | |
| 2.297 | 2-$CH_3$ | 5-Cl | H | $CH_3$ | $CHCl_2$ | |
| 2.298 | 2-$CH_3$ | 5-Cl | H | $C_2H_5$ | $CHCl_2$ | |
| 2.299 | 2-$CH_3$ | 5-Cl | H | $CH_3$ | $CCl_2CF_3$ | |
| 2.300 | 2-$CH_3$ | 5-Cl | H | $CH_3$ | $CCl_2CH_3$ | |
| 2.301 | 2-$CH_3$ | 5-Cl | H | $OCH_3$ | $CF_3$ | |
| 2.302 | 2-$CH_3$ | 5-Cl | H | $OC_2H_5$ | $CF_3$ | |
| 2.303 | 2-$CH_3$ | 5-Cl | H | $SCH_3$ | $CF_3$ | |
| 2.304 | 2-$CH_3$ | 5-Cl | H | $SC_2H_5$ | $CF_3$ | |
| 2.305 | 2-$CH_3$ | 5-Cl | H | $SC_4H_9(i)$ | $CF_3$ | |
| 2.306 | 2-$CH_3$ | 3-Cl | H | $CH_3$ | Cl | m.p. 116–117° C. |
| 2.307 | 2-$CH_3$ | 3-Cl | H | $CH_3$ | $CF_3$ | |
| 2.308 | 2-$CH_3$ | 3-Cl | H | $C_2H_5$ | $CF_3$ | |
| 2.309 | 2-$CH_3$ | 3-Cl | H | $C_3H_7(i)$ | $CF_3$ | |
| 2.310 | 2-$CH_3$ | 3-Cl | H | Cyclopropyl | $CF_3$ | |
| 2.311 | 2-$CH_3$ | 3-Cl | H | $CH_3$ | $CF_2Cl$ | |
| 2.312 | 2-$CH_3$ | 3-Cl | H | $CH_3$ | $CF_2CF_3$ | |
| 2.313 | 2-$CH_3$ | 3-Cl | H | $C_2H_5$ | $CF_2CF_3$ | |
| 2.314 | 2-$CH_3$ | 3-Cl | H | $OCH_3$ | $CF_3$ | |
| 2.315 | 2-$CH_3$ | 3-Cl | H | $SCH_3$ | $CF_3$ | |
| 2.316 | 2-$CH_3$ | 5-$NO_2$ | H | $CH_3$ | Cl | m.p. 178–179° C. |
| 2.317 | 2-$CH_3$ | 5-$NO_2$ | H | $CH_3$ | $CF_3$ | |
| 2.318 | 2-$CH_3$ | 5-$NO_2$ | H | $CH_3$ | $CF_2Cl$ | |
| 2.319 | 2-$CH_3$ | 5-$NO_2$ | H | $CH_3$ | $CHF_2$ | |
| 2.320 | 2-$CH_3$ | 5-$NO_2$ | H | $C_2H_5$ | $CF_3$ | |
| 2.321 | 2-$CH_3$ | 5-$NO_2$ | H | $C_3H_7(n)$ | $CF_3$ | |
| 2.322 | 2-$CH_3$ | 5-$NO_2$ | H | $C_3H_7(i)$ | $CF_3$ | |
| 2.323 | 2-$CH_3$ | 5-$NO_2$ | H | $C_4H_9(t)$ | $CF_3$ | |
| 2.324 | 2-$CH_3$ | 3-$NO_2$ | H | $CH_3$ | Cl | m.p. 160–161° C. |
| 2.325 | 2-$CH_3$ | 3-$NO_2$ | H | $CH_3$ | $CF_3$ | |
| 2.326 | 2-$CH_3$ | 3-$NO_2$ | H | $CH_3$ | $CF_2CF_3$ | |
| 2.327 | 2-$CH_3$ | 3-$NO_2$ | H | $C_2H_5$ | $CF_2CF_3$ | |
| 2.328 | 2-$CH_3$ | 3-$NO_2$ | H | Phenyl | $CF_3$ | |

TABLE II-continued

Compounds of formula

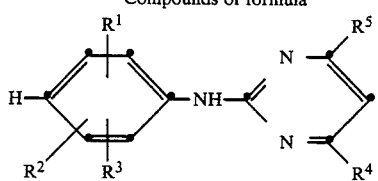

II

| Comp. No. | $R^1$ | $R^2$ | $R^3$ | $R^4$ | $R^5$ | Physical data |
|---|---|---|---|---|---|---|
| 2.329 | 2-$CH_3$ | 3-$NO_2$ | H | $C_2H_5$ | $CF_3$ | |
| 2.330 | 2-$CH_3$ | 3-$NO_2$ | H | $C_3H_7$(i) | $CF_3$ | |
| 2.331 | 2-$CH_3$ | 6-$CF_3$ | H | $CH_3$ | Cl | |
| 2.332 | 2-$CH_3$ | 6-$CF_3$ | H | $CH_3$ | $CF_3$ | m.p. 100–101° C. |
| 2.333 | 2-$CH_3$ | 6-$CF_3$ | H | $CH_3$ | $CHF_2$ | |
| 2.334 | 2-$CH_3$ | 6-$CF_3$ | H | $CH_3$ | $CF_2Cl_2$ | |
| 2.335 | 2-$CH_3$ | 6-$CF_3$ | H | $CH_3$ | $CHCl_2$ | |
| 2.336 | 2-$CH_3$ | 6-$CF_3$ | H | $OCH_3$ | $CF_3$ | |
| 2.337 | 2-$CH_3$ | 6-$CF_3$ | H | $OC_2H_5$ | $CF_3$ | |
| 2.338 | 2-$CH_3$ | 6-$CF_3$ | H | $SCH_3$ | $CF_3$ | |
| 2.339 | 2-$CH_3$ | 6-$CF_3$ | H | $SC_2H_5$ | $CF_3$ | |
| 2.340 | 2-$CH_3$ | 6-$CF_3$ | H | $C_2H_5$ | $CF_3$ | |
| 2.341 | 2-$CH_3$ | 6-$CF_3$ | H | $CH_3$ | $CF_2CF_3$ | |
| 2.342 | 2-$CH_3$ | 6-$CF_3$ | H | $C_2H_5$ | $CF_2CF_3$ | |
| 2.343 | 2-$CH_3$ | 6-$CF_3$ | H | $C_3H_7$(i) | $CF_3$ | |
| 2.344 | 2-$CH_3$ | 6-$CF_3$ | H | $C_3H_7$(n) | $CF_3$ | |
| 2.345 | 2-$CH_3$ | 6-$CF_3$ | H | Cyclopropyl | $CF_3$ | |
| 2.346 | 2-$OCHF_2$ | 5-Cl | H | $CH_3$ | Cl | m.p. 61–62° C. |
| 2.347 | 2-$OCHF_2$ | 5-Cl | H | $CH_3$ | $CH_3$ | |
| 2.348 | 2-$OCHF_2$ | 5-Cl | H | $CH_3$ | $CHCl_2$ | |
| 2.349 | 2-$OCHF_2$ | 5-Cl | H | $CH_3$ | CHFCl | |
| 2.350 | 2-$OCHF_2$ | 5-Cl | H | $CH_3$ | $CHF_2$ | |
| 2.351 | 2-$OCHF_2$ | 5-Cl | H | $CH_3$ | $CF_2Cl$ | |
| 2.352 | 2-$OCHF_2$ | 5-Cl | H | $CH_3$ | $CF_3$ | m.p. 66–67° C. |
| 2.353 | 2-$OCHF_2$ | 5-Cl | H | $CH_3$ | $CF_2CF_3$ | |
| 2.354 | 2-$OCHF_2$ | 5-Cl | H | $CH_3$ | $CCl_2CF_3$ | |
| 2.355 | 2-$OCHF_2$ | 5-Cl | H | $CH_3$ | $CCl_2CH_3$ | |
| 2.356 | 2-$OCHF_2$ | 5-Cl | H | $C_2H_5$ | $CF_3$ | |
| 2.357 | 2-$OCHF_2$ | 5-Cl | H | $C_3H_7$(n) | $CF_3$ | |
| 2.358 | 2-$OCHF_2$ | 5-Cl | H | $C_3H_7$(i) | $CF_3$ | |
| 2.359 | 2-$CH_3$ | 6-Cl | H | Cyclopropyl | $CF_3$ | |
| 2.360 | 2-$CH_3$ | 6-Cl | H | $C_4H_9$(n) | $CF_3$ | |
| 2.361 | 2-$CH_3$ | 6-Cl | H | $C_4H_9$(i) | $CF_3$ | |
| 2.362 | 2-$CH_3$ | 6-Cl | H | $C_4H_9$(t) | $CF_3$ | |
| 2.363 | 2-$CH_3$ | 6-Cl | H | Phenyl | $CF_3$ | |
| 2.364 | 2-$CH_3$ | 6-Cl | H | 2-Furyl | $CF_3$ | |
| 2.365 | 2-$CH_3$ | 6-Cl | H | 2-Thienyl | $CF_3$ | |
| 2.366 | 2-$CH_3$ | 6-Cl | H | $C_2H_5$ | $CF_2CF_3$ | |
| 2.367 | 2-$CH_3$ | 6-Cl | H | $C_2H_5$ | $CCl_2CH_3$ | |
| 2.368 | 2-$CH_3$ | 6-Cl | H | $OCH_3$ | $CF_3$ | |
| 2.369 | 2-$CH_3$ | 6-Cl | H | $OC_2H_5$ | $CF_3$ | |
| 2.370 | 2-$CH_3$ | 6-Cl | H | $SCH_3$ | $CF_3$ | |
| 2.371 | 2-$CH_3$ | 6-Cl | 3-Cl | $CH_3$ | Cl | |
| 2.372 | 2-$CH_3$ | 6-Cl | 3-Cl | $CH_3$ | $CF_3$ | |
| 2.373 | 2-$CH_3$ | 6-Cl | 3-Cl | $C_2H_5$ | $CF_3$ | |
| 2.374 | 2-$CH_3$ | 6-Cl | 3-Cl | $C_3H_7$(i) | $CF_3$ | |
| 2.375 | 2-$CH_3$ | 6-Cl | 3-Cl | $CH_3$ | $CF_2CF_3$ | |
| 2.376 | 2-$CH_3$ | 6-Cl | 3-Cl | Phenyl | $CF_3$ | |
| 2.377 | 2-$CH_3$ | 6-Cl | 3-Cl | $OCH_3$ | $CF_3$ | |
| 2.378 | 2-$CH_3$ | 6-Cl | 3-Cl | $OC_2H_5$ | $CF_3$ | |
| 2.379 | 2-$CH_3$ | 6-Cl | 3-Cl | $SC_2H_5$ | $CF_3$ | |
| 2.380 | 2-$OCH_3$ | 3-Cl | H | $CH_3$ | $CF_3$ | m.p. 41–42° C. |
| 2.381 | 2-$OCH_3$ | 3-Cl | H | $C_2H_5$ | $CF_3$ | |
| 2.382 | 2-$OCH_3$ | 3-Cl | H | $C_3H_7$(n) | $CF_3$ | |
| 2.383 | 2-$OCH_3$ | 3-Cl | H | Cyclopropyl | $CF_3$ | |
| 2.384 | 2-$OCH_3$ | 3-Cl | H | $CH_3$ | Cl | |
| 2.385 | 2-$OCH_3$ | 3-Cl | H | $CH_3$ | $CF_2CF_3$ | |
| 2.386 | 2-$OCH_3$ | 3-Cl | H | $OCH_3$ | $CF_3$ | |
| 2.387 | 2-$OCH_3$ | 3-Cl | H | $SCH_3$ | $CF_3$ | |
| 2.388 | 2-$OCH_3$ | 3-Cl | H | $CH_3$ | $CF_2Cl$ | |
| 2.389 | 2-$OCH_3$ | 3-Cl | H | $CH_3$ | $CHF_2$ | |
| 2.390 | 2-$OCH_3$ | 3-Cl | H | $CH_3$ | Cl | |
| 2.391 | 2-$OCH_3$ | 3-Cl | H | $CH_3$ | $CH_3$ | m.p. 106–107° C. |
| 2.392 | 2-$OCH_3$ | 3-Cl | H | $CH_3$ | $CF_3$ | m.p. 65–66° C. |
| 2.393 | 2-$OCH_3$ | 3-Cl | H | $CH_3$ | Br | |
| 2.394 | 2-$OCH_3$ | 3-Cl | H | CN | $CH_3$ | |
| 2.395 | 2-$OCH_3$ | 3-Cl | H | $CH_3$ | $CF_2Cl$ | |
| 2.396 | 2-$OCH_3$ | 3-Cl | H | $CH_3$ | $CHF_2$ | |

TABLE II-continued

Compounds of formula II

| Comp. No. | R¹ | R² | R³ | R⁴ | R⁵ | Physical data |
|---|---|---|---|---|---|---|
| 2.397 | 2-OCH$_3$ | 3-Cl | H | CH$_3$ | CHCl$_2$ | |
| 2.398 | 2-OCH$_3$ | 3-Cl | H | CH$_3$ | CF$_2$CF$_3$ | m.p. 75-76° C. |
| 2.399 | 2-OCH$_3$ | 3-Cl | H | CH$_3$ | CCl$_2$CF$_3$ | |
| 2.400 | 2-OCH$_3$ | 3-Cl | H | CH$_3$ | CHClF | |
| 2.401 | 2-OCH$_3$ | 3-Cl | H | CH$_3$ | CCl$_2$CH$_3$ | |
| 2.402 | 2-OCH$_3$ | 3-Cl | H | C$_2$H$_5$ | CF$_3$ | |
| 2.403 | 2-OCH$_3$ | 5-Cl | H | C$_2$H$_5$ | CF$_2$CF$_3$ | m.p. 64-65° C. |
| 2.404 | 2-OCH$_3$ | 5-Cl | H | C$_2$H$_5$ | CF$_2$Cl | |
| 2.405 | 2-OCH$_3$ | 5-Cl | H | C$_3$H$_7$(n) | CF$_3$ | n$_D^{25}$: 1,5463 |
| 2.406 | 2-OCH$_3$ | 5-Cl | H | C$_3$H$_7$(i) | CF$_3$ | n$_D^{25}$: 1,5455 |
| 2.407 | 2-OCH$_3$ | 5-Cl | H | C$_3$H$_7$(i) | CF$_2$CF$_3$ | |
| 2.408 | 2-OCH$_3$ | 5-Cl | H | Cyclopropyl | CF$_3$ | |
| 2.409 | 2-OCH$_3$ | 5-Cl | H | C$_4$H$_9$(n) | CF$_3$ | |
| 2.410 | 2-OCH$_3$ | 5-Cl | H | C$_2$H$_5$(i) | CF$_3$ | |
| 2.411 | 2-OCH$_3$ | 5-Cl | H | C$_4$H$_9$(t) | CF$_3$ | m.p. 55-56° C. |
| 2.412 | 2-OCH$_3$ | 5-Cl | H | OCH$_3$ | CF$_3$ | |
| 2.413 | 2-OCH$_3$ | 5-Cl | H | OC$_4$H$_9$(n) | CF$_3$ | |
| 2.414 | 2-OCH$_3$ | 5-Cl | H | SCH$_3$ | CF$_3$ | |
| 2.415 | 2-OCH$_3$ | 5-Cl | H | SC$_2$H$_5$ | CF$_3$ | |
| 2.416 | 2-OCH$_3$ | 5-Cl | H | SC$_3$H$_7$(n) | CF$_3$ | |
| 2.417 | 2-OCH$_3$ | 5-Cl | H | SC$_3$H$_7$(i) | CF$_3$ | |
| 2.418 | 2-OC$_2$H$_5$ | 5-Cl | H | CH$_3$ | Cl | |
| 2.419 | 2-OC$_2$H$_5$ | 5-Cl | H | CH$_3$ | CF$_3$ | |
| 2.420 | 2-OC$_2$H$_5$ | 5-Cl | H | C$_2$H$_5$ | CF$_3$ | |
| 2.421 | 2-OC$_2$H$_5$ | 5-Cl | H | C$_3$H$_7$(i) | CF$_3$ | |
| 2.422 | 2-OC$_2$H$_5$ | 5-Cl | H | Cyclopropyl | CF$_3$ | |
| 2.423 | 2-OC$_2$H$_5$ | 5-Cl | H | Phenyl | CF$_3$ | |
| 2.424 | 2-OC$_2$H$_5$ | 5-Cl | H | OCH$_3$ | CF$_3$ | |
| 2.425 | 2-OC$_2$H$_5$ | 5-Cl | H | CH$_3$ | CF$_2$CF$_3$ | |
| 2.426 | 2-OC$_3$H$_7$(i) | 5-Cl | H | CH$_3$ | Cl | |
| 2.427 | 2-OC$_3$H$_7$(i) | 5-Cl | H | CH$_3$ | CF$_3$ | |
| 2.428 | 2-OC$_3$H$_7$(i) | 5-Cl | H | CH$_3$ | CF$_2$Cl | |
| 2.429 | 2-OC$_3$H$_7$(i) | 5-Cl | H | C$_2$H$_5$ | CF$_3$ | |
| 2.430 | 2-OC$_3$H$_7$(i) | 5-Cl | H | C$_3$H$_7$(n) | CF$_3$ | |
| 2.431 | 2-OC$_3$H$_7$(i) | 5-Cl | H | CH$_3$ | CHF$_3$ | |
| 2.432 | 2-OC$_3$H$_7$(i) | 5-Cl | H | OCH$_3$ | CF$_3$ | |
| 2.433 | 2-OC$_3$H$_7$(i) | 5-Cl | H | SCH$_3$ | CF$_3$ | |
| 2.434 | 2-OCF$_3$ | H | H | CH$_3$ | Cl | |
| 2.435 | 2-OCF$_3$ | H | H | CH$_3$ | CF$_3$ | n$_D^{23}$: 1,4943 |
| 2.436 | 2-OCF$_3$ | H | H | CH$_3$ | CF$_2$Cl | |
| 2.437 | 2-OCF$_3$ | H | H | CH$_3$ | CHF$_2$ | |
| 2.438 | 2-OCF$_3$ | H | H | CH$_3$ | CHFCl | |
| 2.439 | 2-OCF$_3$ | H | H | C$_2$H$_5$ | CF$_3$ | |
| 2.440 | 2-OCF$_3$ | H | H | C$_3$H$_7$(i) | CF$_3$ | |
| 2.441 | 2-OCF$_3$ | H | H | C$_4$H$_9$(n) | CF$_3$ | |
| 2.442 | 2-OCF$_3$ | H | H | C$_4$H$_9$(t) | CF$_3$ | |
| 2.443 | 2-OCF$_3$ | 5-Cl | H | CH$_3$ | CF$_3$ | |
| 2.444 | 2-OCF$_3$ | 5-Cl | H | CH$_3$ | Cl | |
| 2.445 | 2-OCF$_3$ | 5-Cl | H | CH$_3$ | CF$_3$ | |
| 2.446 | 2-OCF$_3$ | 5-Cl | H | CH$_3$ | CF$_2$Cl | |
| 2.447 | 2-OCF$_3$ | 5-Cl | H | CH$_3$ | CHF$_2$ | |
| 2.448 | 2-OCF$_3$ | 5-Cl | H | CH$_3$ | CHCl$_2$ | |
| 2.449 | 2-OCF$_3$ | 5-Cl | H | CH$_3$ | CHFCl | |
| 2.450 | 2-OCF$_3$ | 5-Cl | H | CH$_3$ | CF$_2$CF$_3$ | |
| 2.451 | 2-OCF$_3$ | 5-Cl | H | C$_2$H$_5$ | CF$_2$CF$_3$ | |
| 2.452 | 2-OCF$_3$ | 5-Cl | H | C$_2$H$_5$ | CF$_3$ | |
| 2.453 | 2-OCF$_3$ | 5-Cl | H | C$_3$H$_7$(i) | CF$_3$ | |
| 2.454 | 2-OCF$_3$ | 5-Cl | H | Cyclopropyl | CF$_3$ | |
| 2.455 | 2-OCF$_3$ | 5-Cl | H | Phenyl | CF$_3$ | |
| 2.456 | 2-OCF$_3$ | 5-Cl | H | OC$_2$H$_5$ | CF$_3$ | |
| 2.457 | 2-OCF$_3$ | 5-Cl | H | SC$_2$H$_5$ | CF$_3$ | |
| 2.458 | 2-SCH$_3$ | H | H | CH$_3$ | Cl | |
| 2.459 | 2-SCH$_3$ | H | H | CH$_3$ | CF$_3$ | m.p. 74-75° C. |
| 2.460 | 2-SCH$_3$ | H | H | CH$_3$ | CHF$_2$ | |
| 2.461 | 2-SCH$_3$ | H | H | CH$_3$ | CF$_2$CF$_3$ | |
| 2.462 | 2-SCH$_3$ | H | H | C$_2$H$_5$ | CF$_3$ | |
| 2.463 | 2-SCH$_3$ | H | H | C$_3$H$_7$(i) | CF$_3$ | n$_D^{25}$: 1,5575 |
| 2.464 | 2-SCH$_3$ | H | H | C$_4$H$_9$(n) | CF$_3$ | |

TABLE II-continued

Compounds of formula II

| Comp. No. | R¹ | R² | R³ | R⁴ | R⁵ | Physical data |
|---|---|---|---|---|---|---|
| 2.465 | 2-SCH$_3$ | H | H | C$_4$H$_9$(t) | CF$_3$ | |
| 2.466 | 2-SCH$_3$ | 5-Cl | H | CH$_3$ | Cl | |
| 2.467 | 2-SCH$_3$ | 5-Cl | H | CH$_3$ | CF$_3$ | m.p. 144–145° C. |
| 2.468 | 2-SCH$_3$ | 5-Cl | H | CH$_3$ | CF$_2$CF$_3$ | |
| 2.469 | 2-SCH$_3$ | 5-Cl | H | CH$_3$ | CF$_2$Cl | |
| 2.470 | 2-SCH$_3$ | 5-Cl | H | C$_2$H$_5$ | CF$_3$ | |
| 2.471 | 2-SOCH$_3$ | H | H | CH$_3$ | Cl | |
| 2.472 | 2-SOCH$_3$ | H | H | CH$_3$ | CF$_3$ | |
| 2.473 | 2-SOCH$_3$ | H | H | CH$_3$ | CHF$_2$ | |
| 2.474 | 2-SOCH$_3$ | H | H | CH$_3$ | CF$_2$CF$_3$ | |
| 2.475 | 2-SOCH$_3$ | H | H | C$_2$H$_5$ | CF$_3$ | |
| 2.476 | 2-SOCH$_3$ | H | H | C$_3$H$_7$(i) | CF$_3$ | |
| 2.477 | 2-SOCH$_3$ | H | H | C$_4$H$_9$(n) | CF$_3$ | |
| 2.478 | 2-SOCH$_3$ | H | H | C$_4$H$_9$(t) | CF$_3$ | |
| 2.479 | 2-SO$_2$CH$_3$ | H | H | CH$_3$ | Cl | m.p. 168° C. |
| 2.480 | 2-SO$_2$CH$_3$ | H | H | CH$_3$ | CF$_3$ | m.p. 149° C. |
| 2.481 | 2-SO$_2$CH$_3$ | H | H | C$_2$H$_5$ | CF$_3$ | |
| 2.482 | 2-SO$_2$CH$_3$ | H | H | C$_3$H$_7$(n) | CF$_3$ | |
| 2.483 | 2-SO$_2$CH$_3$ | H | H | C$_3$H$_7$(i) | CF$_3$ | |
| 2.484 | 2-SO$_2$CH$_3$ | H | H | Cyclopropyl | CF$_3$ | |
| 2.485 | 2-SO$_2$CH$_3$ | H | H | C$_4$H$_9$(i) | CF$_3$ | |
| 2.486 | 2-SO$_2$CH$_3$ | H | H | CH$_3$ | CF$_2$CF$_3$ | |
| 2.487 | 2-SO$_2$CH$_3$ | H | H | C$_2$H$_5$ | CF$_2$CF$_3$ | |
| 2.488 | 2-SO$_2$CH$_3$ | H | H | C$_3$H$_7$(i) | CF$_2$CF$_3$ | |
| 2.489 | 2-SOCH$_3$ | 5-Cl | H | CH$_3$ | Cl | |
| 2.490 | 2-SOCH$_3$ | 5-Cl | H | CH$_3$ | CF$_3$ | m.p. 194–195° C. |
| 2.491 | 2-SOCH$_3$ | 5-Cl | H | C$_2$H$_5$ | CF$_3$ | |
| 2.492 | 2-SOCH$_3$ | 5-Cl | H | CH$_3$ | CF$_2$CF$_3$ | |
| 2.493 | 2-SOCH$_3$ | 5-Cl | H | C$_3$H$_7$(i) | CF$_3$ | |
| 2.494 | 2-SO$_2$CH$_3$ | 5-Cl | H | CH$_3$ | Cl | |
| 2.495 | 2-SO$_2$CH$_3$ | 5-Cl | H | CH$_3$ | CF$_3$ | m.p. 183–184° C. |
| 2.496 | 2-SO$_2$CH$_3$ | 5-Cl | H | C$_2$H$_5$ | CF$_3$ | |
| 2.497 | 2-SO$_2$CH$_3$ | 5-Cl | H | CH$_3$ | CF$_2$CF$_3$ | |
| 2.498 | 2-SO$_2$CH$_3$ | 5-Cl | H | C$_3$H$_7$(i) | CF$_3$ | |
| 2.499 | 2-F | 5-F | H | CH$_3$ | OCHF$_2$ | |
| 2.500 | 2-F | 5-F | H | CH$_3$ | Cl | |
| 2.501 | 2-F | 5-F | H | CH$_3$ | CF$_3$ | m.p. 68–69° C. |
| 2.502 | 2-F | 5-F | H | C$_2$H$_5$ | CF$_3$ | |
| 2.503 | 2-F | 5-F | H | C$_3$H$_7$(n) | CF$_3$ | |
| 2.504 | 2-F | 5-F | H | C$_3$H$_7$(i) | CF$_3$ | |
| 2.505 | 2-F | 5-F | H | Cyclopropyl | CF$_3$ | m.p. 103–104° C. |
| 2.506 | 2-F | 5-F | H | CH$_3$ | CF$_2$CF$_3$ | |
| 2.507 | 2-F | 5-F | H | CH$_3$ | CF$_2$CF$_2$CF$_3$ | |
| 2.508 | 2-F | 5-F | H | CH$_3$ | CF$_2$Cl | |
| 2.509 | 2-F | 5-F | H | CH$_3$ | CHF$_2$ | |
| 2.510 | 2-F | 5-F | H | CH$_3$ | CHClF | |
| 2.511 | 2-F | 5-F | H | C$_2$H$_5$ | CF$_2$Cl | |
| 2.512 | 2-F | 5-F | H | C$_3$H$_7$(i) | CF$_2$Cl | n$_D^{25}$: 1,5358 |
| 2.513 | 2-F | 5-F | H | C$_4$H$_9$(n) | CF$_3$ | |
| 2.514 | 2-F | 5-F | H | C$_4$H$_9$(t) | CF$_3$ | m.p. 37–38° C. |
| 2.515 | 2-F | 5-F | H | C$_2$H$_5$ | CF$_2$CF$_3$ | |
| 2.516 | 2-F | 5-F | H | C$_3$H$_7$(i) | CF$_2$CF$_3$ | m.p. 53–54° C. |
| 2.517 | 2-F | 5-F | H | C$_3$H$_7$(n) | CF$_2$CF$_3$ | |
| 2.518 | 2-F | 5-F | H | CH$_3$ | CCl$_2$CF$_3$ | |
| 2.519 | 2-F | 5-F | H | CH$_3$ | CHCl$_2$ | |
| 2.520 | 2-F | 5-F | H | C$_2$H$_5$ | CHCl$_2$ | n$_D^{25}$: 1,5824 |
| 2.521 | 2-F | 5-F | H | CH$_3$ | CCl$_2$CH$_3$ | |
| 2.522 | 2-F | 5-F | H | OCH$_3$ | CF$_3$ | |
| 2.523 | 2-F | 5-F | H | OC$_3$H$_7$(i) | CF$_3$ | |
| 2.524 | 2-F | 5-F | H | SCH$_3$ | CF$_3$ | |
| 2.525 | 2-F | 5-F | H | SC$_3$H$_7$(i) | CF$_3$ | |
| 2.526 | 2-F | 6-F | H | CH$_3$ | Cl | |
| 2.527 | 2-F | 6-F | H | CH$_3$ | CF$_3$ | m.p. 164° C. |
| 2.528 | 2-F | 6-F | H | C$_2$H$_5$ | CF$_3$ | m.p. 120–121° C. |
| 2.529 | 2-F | 6-F | H | C$_3$H$_7$(n) | CF$_3$ | |
| 2.530 | 2-F | 6-F | H | C$_3$H$_7$(i) | CF$_3$ | m.p. 92–94° C. |
| 2.531 | 2-F | 6-F | H | CH$_3$ | CF$_2$CF$_3$ | |
| 2.532 | 2-F | 6-F | H | C$_2$H$_5$ | CF$_2$CF$_3$ | m.p. 85–87° C. |
| 2.533 | 2-F | 6-F | H | CH$_3$ | CF$_2$Cl | m.p. 92–95° C. |

TABLE II-continued

Compounds of formula II

| Comp. No. | R¹ | R² | R³ | R⁴ | R⁵ | Physical data |
|---|---|---|---|---|---|---|
| 2.534 | 2-F | 6-F | H | $CH_3$ | $CHF_2$ | |
| 2.535 | 2-F | 6-F | H | $CH_3$ | $CHClF$ | |
| 2.536 | 2-F | 6-F | H | $OCH_3$ | $CF_3$ | |
| 2.537 | 2-F | 6-F | H | $SCH_3$ | $CF_3$ | |
| 2.538 | 2-F | 6-Cl | H | $CH_3$ | Cl | |
| 2.539 | 2-F | 6-Cl | H | $CH_3$ | $CH_3$ | |
| 2.540 | 2-F | 6-Cl | H | $CH_3$ | $CF_3$ | m.p. 160–161° C. |
| 2.541 | 2-F | 6-Cl | H | $C_2H_5$ | $CF_3$ | |
| 2.542 | 2-F | 6-Cl | H | $C_3H_7(i)$ | $CF_3$ | m.p. 108–109° C. |
| 2.543 | 2-F | 6-Cl | H | Cyclopropyl | $CF_3$ | m.p. 95–96° C. |
| 2.544 | 2-F | 6-Cl | H | $CH_3$ | $CF_2CF_3$ | |
| 2.545 | 2-F | 6-Cl | H | $C_3H_7(i)$ | $CF_2CF_3$ | |
| 2.546 | 2-F | 6-Cl | H | $CH_3$ | $CCl_2CF_3$ | |
| 2.547 | 2-F | 6-Cl | H | $CH_3$ | $CHCl_2$ | |
| 2.548 | 2-F | 6-Cl | H | $CH_3$ | $CHF_2$ | |
| 2.549 | 2-F | 6-Cl | H | $CH_3$ | $CHFCl$ | |
| 2.550 | 2-F | 6-Cl | H | $CH_3$ | $CF_2Cl$ | |
| 2.551 | 2-F | 6-Cl | H | $C_3H_7(i)$ | $CF_2Cl$ | |
| 2.552 | 2-F | 6-Cl | H | $OCH_3$ | $CF_3$ | |
| 2.553 | 2-CN | H | H | $CH_3$ | $CF_3$ | m.p. 117–118° C. |
| 2.554 | 2-CN | H | H | $C_2H_5$ | $CF_3$ | |
| 2.555 | 2-CN | H | H | $C_3H_7(i)$ | $CF_3$ | |
| 2.556 | 2-CN | H | H | $CH_3$ | $CF_2CF_3$ | |
| 2.557 | 2-CN | H | H | $C_2H_5$ | $CF_2CF_3$ | |
| 2.558 | 2-CN | H | H | $C_3H_7(i)$ | $CF_2CF_3$ | |
| 2.559 | 2-CN | H | H | $CH_3$ | $CHF_2$ | |
| 2.560 | 2-CN | H | H | $CH_3$ | $CF_2Cl$ | |
| 2.561 | 2-CN | H | H | $OCH_3$ | $CF_3$ | |
| 2.562 | 2-CN | H | H | $OC_2H_5$ | $CF_3$ | |
| 2.563 | $2-PO(OC_2H_5)_2$ | H | H | $CH_3$ | $CF_3$ | m.p. 60–61° C. |
| 2.564 | $2-PO(OC_2H_5)_2$ | H | H | $C_2H_5$ | $CF_3$ | |
| 2.565 | $2-PO(OC_2H_5)_2$ | H | H | $C_3H_7(i)$ | $CF_3$ | |
| 2.566 | 2-Cl | 5-Cl | H | $SOCH_3$ | $CF_3$ | |
| 2.567 | 2-Cl | 5-Cl | H | $SO_2CH_3$ | $CF_3$ | |
| 2.568 | 2-Cl | 6-Cl | H | $SOCH_3$ | $CF_3$ | m.p. 144–148° C. |
| 2.569 | 2-Cl | 6-Cl | H | $SO_2CH_3$ | $CF_3$ | m.p. 144–146° C. |
| 2.570 | 2-Cl | 6-Cl | H | $SOCH_3$ | $CH_3$ | |
| 2.571 | 2-Cl | 6-Cl | H | $SO_2CH_3$ | $CH_3$ | |
| 2.572 | 2-Cl | 6-Cl | H | CN | $CH_3$ | |
| 2.573 | 2-Cl | 6-Cl | H | CN | $CF_3$ | |
| 2.574 | 2-Cl | 6-Cl | H | $CH=CCl_2$ | Cl | |
| 2.575 | 2-Cl | 5-Cl | H | $CH=CCl_2$ | Cl | |
| 2.576 | $2-CF_3$ | H | H | $CH=CCl_2$ | Cl | |
| 2.577 | 2-Cl | 6-Cl | H | $CH_2OCH_3$ | $CF_3$ | |
| 2.578 | 2-Cl | 6-Cl | H | $CH_2OCH_3$ | $C_2F_5$ | |
| 2.579 | 2-Cl | 5-Cl | H | $CH_2OCH_3$ | $CF_3$ | |
| 2.580 | 2-Cl | 5-Cl | H | $CH_2OCH_3$ | $CF_2Cl$ | |
| 2.581 | $2-OCH_3$ | 5-Cl | H | $CH_2OCH_3$ | $CF_3$ | |
| 2.582 | $2-OCH_3$ | 5-Cl | H | $CH_2OCH_3$ | $CF_2CF_3$ | |
| 2.583 | 2-F | 5-F | H | $CH_2OCH_3$ | $CF_3$ | |
| 2.584 | $2-OCHF_2$ | 5-Cl | H | $CH_2OCH_3$ | $CF_3$ | |
| 2.585 | $2-OCHF_2$ | 5-Cl | H | $CH_2OCH_3$ | $CF_2Cl$ | |
| 2.586 | 3-Br | H | H | $CH_3$ | Cl | m.p. 101–102° C. |
| 2.587 | 3-Br | H | H | $CH_3$ | $CF_3$ | |
| 2.588 | 2-Br | 5-Br | H | $CH_3$ | Cl | |
| 2.589 | 2-Br | 5-Br | H | $CH_3$ | $CF_3$ | m.p. 95–97° C. |
| 2.590 | 2-Br | 5-Br | H | $OCH_3$ | $CF_3$ | |
| 2.591 | 2-Br | 5-Br | H | $C_2H_5$ | $CF_3$ | |
| 2.592 | 2-Br | 5-Br | H | $CH_3$ | $CF_2Cl$ | |
| 2.593 | 2-Br | 5-Br | H | $CH_3$ | $CHF_2$ | |
| 2.594 | $2-CF_3$ | 5-Cl | H | $CH_3$ | $CF_3$ | m.p. 65–67° C. |
| 2.595 | $2-CF_3$ | 5-Cl | H | $CH_3$ | Cl | m.p. 117–118° C. |
| 2.596 | $2-CF_3$ | 5-Cl | H | $C_2H_5$ | $CF_3$ | |
| 2.597 | $2-CF_3$ | 5-Cl | H | $C_3H_7(i)$ | $CF_3$ | |
| 2.598 | $2-CF_3$ | 5-Cl | H | Cyclopropyl | $CF_3$ | |
| 2.599 | $2-CF_3$ | 5-Cl | H | $CH_3$ | $CH_2Cl$ | |
| 2.600 | $2-CF_3$ | 5-Cl | H | $CH_3$ | $CHF_2$ | |
| 2.601 | $2-CF_3$ | 5-Cl | H | $C_2H_5$ | $CF_2Cl$ | |
| 2.602 | $2-CF_3$ | 5-Cl | H | $C_3H_7(i)$ | $CF_2Cl$ | |

TABLE II-continued

Compounds of formula $$\text{structure with } R^1, R^2, R^3 \text{ on phenyl ring, NH linker to pyrimidine with } R^4, R^5$$

II

| Comp. No. | R¹ | R² | R³ | R⁴ | R⁵ | Physical data |
|---|---|---|---|---|---|---|
| 2.603 | 2-CF$_3$ | 5-Cl | H | CH$_3$ | CF$_2$CF$_3$ | |
| 2.604 | 2-CF$_3$ | 5-Cl | H | OCH$_3$ | CF$_3$ | |
| 2.605 | 2-CF$_3$ | 5-Cl | H | SCH$_3$ | CF$_3$ | |
| 2.606 | 2-CF$_3$ | 5-Cl | H | SOCH$_3$ | CF$_3$ | |
| 2.607 | 2-CF$_3$ | 5-Cl | H | SO$_2$CH$_3$ | CH$_3$ | |
| 2.608 | 2-CH$_3$ | 3-CH$_3$ | H | CH$_3$ | Cl | |
| 2.609 | 2-CH$_3$ | 3-CH$_3$ | H | CH$_3$ | CF$_3$ | |
| 2.610 | 2-CH$_3$ | 5-CH$_3$ | H | CH$_3$ | Cl | |
| 2.611 | 2-CH$_3$ | 5-CH$_3$ | H | CH$_3$ | CF$_3$ | |
| 2.612 | 2-CH$_3$ | 6-CH$_3$ | H | CH$_3$ | Cl | |
| 2.613 | 2-CH$_3$ | 6-CH$_3$ | H | CH$_3$ | CF$_3$ | m.p. 145–146° C. |
| 2.614 | 2-CH$_3$ | 6-CH$_3$ | H | CH$_3$ | CF$_2$Cl | m.p. 147–148° C. |
| 2.615 | 2-CH$_3$ | 6-CH$_3$ | H | CH$_3$ | CH$_2$CF$_3$ | |
| 2.616 | 2-CH$_3$ | 6-CH$_3$ | H | OCH$_3$ | CF$_3$ | |
| 2.617 | 2-CH$_3$ | 6-CH$_3$ | H | SCH$_3$ | CF$_3$ | |
| 2.618 | 2-CH$_3$ | 6-C$_2$H$_5$ | H | CH$_3$ | Cl | |
| 2.619 | 2-CH$_3$ | 6-C$_2$H$_5$ | H | CH$_3$ | CF$_3$ | m.p. 90–93° C. |
| 2.620 | 2-CH$_3$ | 6-C$_2$H$_5$ | H | OCH$_3$ | CF$_3$ | |
| 2.621 | 2-CH$_3$ | 5-F | H | CH$_3$ | Cl | |
| 2.622 | 2-CH$_3$ | 5-F | H | CH$_3$ | CF$_3$ | m.p. 78–79° C. |
| 2.623 | 2-CH$_3$ | 5-F | H | CH$_3$ | CHF$_2$ | |
| 2.624 | 2-CH$_3$ | 5-F | H | CH$_3$ | CF$_2$Cl | |
| 2.625 | 2-CH$_3$ | 5-F | H | C$_2$H$_5$ | CF$_3$ | |
| 2.626 | 2-CH$_3$ | 5-F | H | C$_3$H$_7$(i) | CF$_3$ | |
| 2.627 | 2-CH$_3$ | 5-F | H | OCH$_3$ | CF$_3$ | |
| 2.628 | 2-CH$_3$ | 5-F | H | OC$_2$H$_5$ | CF$_3$ | |
| 2.629 | 2-Br | 6-Br | H | CH$_3$ | Cl | |
| 2.630 | 2-Br | 6-Br | H | CH$_3$ | CF$_3$ | |
| 2.631 | 2-Br | 6-Br | H | C$_2$H$_5$ | CF$_3$ | m.p. 104–105° C. |
| 2.632 | 2-Br | 6-Br | H | C$_3$H$_7$(i) | CF$_3$ | |
| 2.633 | 2-Br | 6-Br | H | Cyclopropyl | CF$_3$ | |
| 2.634 | 2-Br | 6-Br | H | CH$_3$ | CHCl$_2$ | |
| 2.635 | 2-Br | 6-Br | H | CH$_3$ | CF$_2$CF$_3$ | |
| 2.636 | 2-Br | H | H | C$_3$H$_7$(i) | CF$_2$CF$_3$ | n$_D^{25}$: 1,5307 |
| 2.637 | 2-CF$_3$ | H | H | CH$_3$ | CHCl$_2$ | m.p. 72–74° C. |
| 2.638 | 2-OCHF$_2$ | H | H | CH$_3$ | CF$_3$ | m.p. 71–72° C. |
| 2.639 | 2-OCHF$_2$ | H | H | C$_3$H$_7$(i) | CF$_3$ | |
| 2.640 | 2-OCHF$_2$ | H | H | Cyclopropyl | CF$_3$ | n$_D^{25}$: 1,5242 |
| 2.641 | 2-OCHF$_2$ | H | H | CH$_3$ | CHF$_2$ | |
| 2.642 | 2-OCHF$_2$ | H | H | CH$_3$ | CHFCl | |
| 2.643 | 2-CF$_3$ | H | H | CH$_3$ | CHF$_2$ | |
| 2.644 | 2-CF$_3$ | H | H | CH$_3$ | CF$_2$Cl | |
| 2.645 | 2-CF$_3$ | H | H | C$_3$H$_7$(i) | CF$_2$Cl | n$_D^{25}$: 1,5184 |
| 2.646 | 2-CF$_3$ | H | H | Cyclopropyl | CF$_3$ | m.p. 63–64° C. |
| 2.647 | 2-CF$_3$ | H | H | 2-Thienyl | CF$_3$ | m.p. 97–98° C. |
| 2.648 | 2-Br | H | H | C$_4$H$_9$(n) | CF$_3$ | m.p. 65–66° C. |
| 2.649 | 2-Br | H | H | C$_3$H$_7$(i) | CF$_3$ | n$_D^{25}$: 1,5583 |
| 2.650 | 2-Br | H | H | CH$_3$ | CHF$_2$ | |
| 2.651 | 2-Br | H | H | CH$_3$ | CF$_2$Cl | |
| 2.652 | 2-Br | H | H | Cyclopropyl | CF$_2$Cl | |
| 2.653 | 2-Br | H | H | C$_2$H$_5$ | CHF$_2$ | |
| 2.654 | 2-Cl | 6-CH$_3$ | H | CH$_3$ | CH$_3$ | m.p. 141–142° C. |
| 2.655 | 2-Cl | 6-Cl | H | CH$_3$ | CHF$_2$ | m.p. 99–101° C. |
| 2.656 | 2-Cl | 6-Cl | H | C$_2$H$_5$ | CHF$_2$ | |
| 2.657 | 2-Cl | 5-Cl | H | C$_5$H$_{11}$(n) | CF$_3$ | m.p. 56–57° C. |
| 2.658 | 2-COOCH$_3$ | H | H | CH$_3$ | CF$_3$ | m.p. 143–145° C. |
| 2.659 | 2-COOCH$_3$ | H | H | C$_2$H$_5$ | CF$_3$ | |
| 2.660 | 2-COOCH$_3$ | H | H | C$_3$H$_7$(i) | CF$_3$ | |
| 2.661 | 2-COOCH$_3$ | H | H | Cyclopropyl | CF$_3$ | |
| 2.662 | 2-COOCH$_3$ | H | H | CH$_3$ | CF$_2$Cl | |
| 2.663 | 2-COOCH$_3$ | H | H | CH$_3$ | CHF$_2$ | |
| 2.664 | 2-COOC$_2$H$_5$ | H | H | CH$_3$ | CF$_3$ | |
| 2.665 | 2-COOC$_3$H$_7$(n) | H | H | CH$_3$ | CF$_3$ | |
| 2.666 | 2-COOC$_3$H$_7$(i) | H | H | CH$_3$ | CF$_3$ | |
| 2.667 | 2-COOC$_4$H$_9$(n) | H | H | CH$_3$ | CF$_3$ | |
| 2.668 | 2-OCH$_3$ | 5-F | H | CH$_3$ | CF$_3$ | m.p. 89–93° C. |

TABLE II-continued

Compounds of formula II

| Comp. No. | R¹ | R² | R³ | R⁴ | R⁵ | Physical data |
|---|---|---|---|---|---|---|
| 2.669 | 2-OCH₃ | 5-F | H | CH₃ | CHF₂ | |
| 2.670 | 2-OCH₃ | 5-F | H | C₂H₅ | CHF₂ | |
| 2.671 | 2-OCH₃ | 5-F | H | C₃H₇(i) | CF₃ | |
| 2.672 | 2-OCH₃ | 5-F | H | Cyclopropyl | CF₃ | |
| 2.673 | 2-OCH₃ | 5-F | H | Cyclopropyl | CF₂Cl | |
| 2.674 | 2-OCHF₂ | 5-F | H | CH₃ | CF₃ | |
| 2.675 | 2-OCHF₂ | 5-F | H | CH₃ | CHF₂ | |
| 2.676 | 2-OCHF₂ | 5-F | H | CH₃ | CF₂Cl | |
| 2.677 | 2-COOCH₃ | 6-CH₃ | H | CH₃ | CF₃ | m.p. 90–91° C. |
| 2.678 | 2-COOCH₃ | 6-CH₃ | H | CH₃ | CHF₂ | |
| 2.679 | 2-COOCH₃ | 6-CH₃ | H | C₃H₇(i) | CF₃ | |
| 2.680 | 2-COOCH₃ | 6-CH₃ | H | Cyclopropyl | CF₃ | |
| 2.681 | 2-COOCH₃ | 6-Cl | H | CH₃ | CF₃ | m.p. 86–87° C. |
| 2.682 | 2-COOCH₃ | 6-Cl | H | CH₃ | CHF₂ | |
| 2.683 | 2-Br | 2-Br | H | H | 2-Furyl | CF₃ | m.p. 108–109° C. |
| 2.684 | 2-Cl | 6-Cl | 3-CH₃ | CH₃ | Cl | m.p. 158–164° C. |
| 2.685 | 2-CF₃ | H | H | C₂H₅ | CHCl₂ | n_D²⁵: 1,5462 |
| 2.686 | 2-Cl | 5-Cl | H | Cl | CF₃ | m.p. 66–67° C. |
| 2.687 | 2-CONH₂ | H | H | CH₃ | CF₃ | m.p. 187–190° C. |
| 2.688 | 2-Cl | 6-Cl | H | CH₃ / CHCH₂CH₃ | CF₃ | m.p. 91–92° C. |
| 2.689 | 2-F | H | H | C₂H₅ | CF₃ | n_D²⁵: 1,5332 |
| 2.690 | 2-F | H | H | CH₂OCH₂ | CF₃ | m.p. 48–50° C. |
| 2.691 | 2-F | H | H | CH₂OCH₃ | CF₂Cl | n_D²⁵: 1,5525 |
| 2.692 | 2-OCH₃ | 6-Cl | H | CH₃ | CF₃ | m.p. 113–114° C. |
| 2.693 | 2-OCH₃ | 6-Cl | H | C₂H₅ | CF₃ | m.p. 68–70° C. |
| 2.694 | 2-OCH₃ | 6-Cl | H | C₃H₇(i) | CF₃ | m.p. 80–81° C. |
| 2.695 | 2-CH₃ | 6-CH₃ | H | C₂H₅ | CF₃ | m.p. 88–89° C. |
| 2.696 | 2-CH₃ | 6-CH₃ | H | C₃H₇(i) | CF₃ | m.p. 64–65° C. |
| 2.697 | 2-F | 6-F | H | C₄H₉(i) | CF₃ | m.p. 97–99° C. |
| 2.698 | 2-F | 6-F | H | cyclopropyl | CF₃ | m.p. 111–113° C. |
| 2.699 | 2-F | 6-F | H | CH₂OCH₂ | CF₃ | m.p. 62–65° C. |
| 2.700 | 2-F | 6-F | H | C₂H₅ | CHCl₂ | m.p. 123–125° C. |
| 2.701 | 2-F | 6-F | H | 2-Furyl | CF₃ | m.p. 122–123° C. |
| 2.702 | 2-CH₃ | 5-F | H | C₂H₅ | CHCl₂ | Oel |
| 2.703 | 2-Cl | 6-CH₃ | H | CH₂OCH₃ | CF₃ | m.p. 95–96° C. |
| 2.704 | 2-Cl | 6-CH₃ | H | CH₂OCH₃ | CF₂Cl | m.p. 103–105° C. |
| 2.705 | 2-Cl | 6-CH₃ | H | C₃H₇(i) | CF₂Cl | m.p. 60–61° C. |
| 2.706 | 2-Cl | 6-CH₃ | H | Cl | CF₃ | m.p. 102° C. |
| 2.707 | 2-Cl | 6-CH₃ | H | CH₂OCH₃ | CHF₂ | n_D²⁵: 1,5375 |
| 2.708 | 2-F | H | H | CH₂OCH₃ | CHF₂ | m.p. 44–45° C. |
| 2.709 | 2-OCH₃ | 6-CH₃ | H | CH₃ | CF₃ | m.p. 94–95° C. |
| 2.710 | 2-Cl | 6-Cl | H | Cl | CF₃ | m.p. 124–125° C. |
| 2.711 | 2-SCHF₂ | H | H | CH₃ | CF₃ | m.p. 78–79° C. |
| 2.712 | 2-OCHF₂ | 6-CH₃ | H | CH₃ | CF₃ | n_D²³: 1,5050 |
| 2.713 | 2-OCHF₂ | 6-CH₃ | H | C₂H₅ | CF₃ | n_D²³: 1,4910 |
| 2.714 | 2-F | 6-Cl | H | 2-Furyl | CF₃ | m.p. 119–120° C. |
| 2.715 | 2-CH₃ | 6-F | H | C₂H₅ | CHCl₂ | |

P. 3. Compounds of formula III

P. 3.1.
N-chlorocarbonyl-N-(4,6-dimethyl-pyrimidin-2-yl)-2,5-dichloroaniline 5.0 g (0.018 mole) of N-(4,6-dimethyl-pyrimidin-2-yl)-2,5-dichloroaniline are dissolved in 100 ml of toluene and heated to reflux. A gentle stream of phosgene is then introduced for a period of 4 hours. The excess phosgene is blown out with nitrogen, and the toluene solution is washed cold with water, dried with magnesium sulfate and then concentrated by evaporation. 5.8 g (95.1%) of the title compound of formula

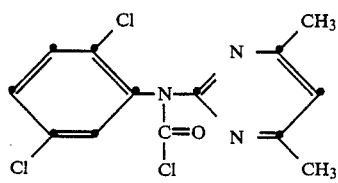

are isolated in the form of crystals having a melting point of 121°–123° C.

BIOLOGICAL EXAMPLES

Example B1: Pre-emergence herbicidal action

In a greenhouse, immediately after sowing the test plants in seed trays the surface of the soil is treated with an aqueous spray mixture corresponding to a rate of application of 4 kg of active ingredient/hectare. The seed trays are kept in a greenhouse at 22°–25° C. and 50–70% relative humidity.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action. Ratings of 6 to 9 (especially 7 to 9) indicate a good tolerance (especially in the case of crop plants).

In this test the following compounds of formula I show good to very good herbicidal action against Setaria italica and Stellaria media: Compound Nos. 1.009, 1.016, 1.020, 1.021, 1.023, 1.032, 1.037, 1.038, 1.042, 1.050, 1.052, 1.055, 1.056, 1.064, 1.065, 1.096, 1.109, 1.113, 1.132, 1.141, 1.144, 1.170, 1.219, 1.221, 1.258, 1.271, 1.332, 1.346, 1.380, 1.392, 1.459, 1.501, 1.505, 1.527, 1.528, 1.540, 1.543, 1.553, 1.638, 1.691, 1.703 and 1.712.

Example B2: Pre-emergence herbicidal action (selective herbicidal action)

Immediately after the test plants have been sawn into beakers with 12 to 15 cm diameter the covering soil was treated with an aqueous formulation containing the active ingredient according to an application rate of 1000 and 500 [g] AS/[ha].

The beakers were kept in a greenhouse at temperature between 22° and 25° C. and a rel. humidity of 50 to 70%.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action. Ratings of 6 to 9 (especially 7 to 9) indicate a good tolerance (especially in case of crop plants).

The results of this experiment are compiled in table III. In this tale T denotes good to very good tolerance (to the crop) and H denotes a good to very good herbicidal action (against the crop).

TABLE III

| Plants tested | Compound No. | | | | | | |
|---|---|---|---|---|---|---|---|
| | 1.020 | 1.055 | 1.056 | 1.141 | 1.219 | 1.528 | 1.540 |
| barley | T | | T | T | T | T | T |
| wheat | T | | T | | T | T | T |
| maize | T | T | T | T | T | T | T |
| soybeans | T | T | T | T | T | T | T |
| cotton | T | T | T | T | T | T | T |
| sunflower | T | T | T | T | T | T | T |
| rape | | | | | | | T |
| Lolium perenne | | H | H | | | | H |
| Alopecurus Myos. | | H | | | | | H |
| Digitaria sang. | H | H | | H | H | H | H |
| Echinochloa crus galli | H | H | | H | | H | H |
| Sorghum halep. | | | | H | H | H | H |
| Chenopodium Sp. | H | H | H | | H | H | H |
| Solanum nigrum | | | | H | H | | |
| Stellaria | H | H | H | H | | H | H |
| Viola tricolor | | | | H | H | H | H |
| Galuim aparine | H | H | | | | | H |
| Veronica Sp. | H | H | H | H | H | H | H |

Example B3: Selective herbicidal action in paddy (transplanted rice)

Water weeds are sown in plastic beakers (425 cm² surface area, 5 l volume). To this rice which is transplanted at the three foliar stage. After sowing and transplantation the beakers are filled to the soil surface with water. 3 days after sowing and transplantation the water level is raised slightly above (3–5 mm) the surface of the soil. The application of the test substance is done three days after sowing and transplantation at an application rate of 1000 and 500 [g/ha] by injecting an aqueous emulsion into the water (the application volume corresponds to 1400 l/ha). The plant beakers are then place in a greenhouse under optimum growth conditions for the rice and the weeds, i.e. 25°–30° C. and high humidity.

The test is evaluated three weeks after application in comparison with an untreated control using a nine-stage evaluation scale.

Ratings of 1 to 4 (especially 1 to 3) indicate good to very good herbicidal action. Ratings of 6 to 9 (especially 7 to 9) indicate a good tolerance (especially in rice).

In this test compounds nos. 1.009, 1.096 and 1.141 exhibit very good herbicidal action against Echinochloa crus galli and show a very good tolerance in rice. Moreover compound 1.141 shows very good herbicidal action against Monocharia.

Example B4: Growth inhibition in cereals

The plants (for example summer barley of the Iban variety) are sown in 15 cm plastics pots containing sterilized soil and cultivated in a climatic chamber at a daytime temperature of 10°–15° C. and a night time temperature of 5°–10° C. The illumination time is 13.5 hours per day at an intensity of approximately 25000 Lux.

Approximately 34 days after sowing and after thinning out to 4 plants per pot, 0.3 to 3 kg of active ingredient/ha, generally as a 25% strength formulation in an aqueous spray mixture, are applied. The amount of water applied is approximately 500 l/ha. After the application the plants are placed in a greenhouse at a daytime temperature of at least 10° C. The illumination time is at least 13.5 hours/day.

The evaluation is carried out approximately 28 days after the treatment. At this point the height of the new growth is measured.

The compounds of formula I tested cause a reduction in new growth compared with the untreated control.

Example B5: Growth inhibition in grasses with trefoil

A mixture of grasses (for example Poa, Festuca, Lolium, Bromus, Cynosurus) and trefoil (*Trifolium pratense/repens*) is sown in 15 cm plastics pots containing sterile soil and cultivated in a greenhouse at a daytime temperature of 21° C. and a night time temperature of 17° C. The illumination time is 13.5 hours/day at a light intensity of at least 7000 Lux. After emergence, the plants are cut back weekly to a height of approximately 6 cm. Approximately 42 days after sowing and 1 day after the last cut, 0.3 to 3 kg of active ingredient/hectare are applied, generally in a 25% strength formulation in an aqueous spray mixture. The amount of water applied is approximately 500 l/ha.

Evaluation is carried out approximately 3 weeks after the treatment. At this point the height of the new growth is measured.

The compounds of formula I tested cause a reduction in new growth compared with the untreated control.

FORMULATION EXAMPLES

Example F1: Formulation Examples for active ingredients of formula I, (throughout, percentages are by weight)

| (a) Emulsifiable concentrates | (a) | (b) | (c) |
|---|---|---|---|
| a compound according to Preparation Example 1 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
|---|---|---|---|
| a compound according to Preparation Example 1 | 80% | 10% | 5% |
| ethylene glycol monomethyl ether | 20% | — | — |
| polyethylene glycol MW 400 | — | 70% | — |
| N-methyl-2-pyrrolidone | — | 20% | 5% |
| epoxidised coconut oil | — | — | 90% |

These solutions are suitable for application in the form of micro-drops.

| (c) Granulates | (a) | (b) |
|---|---|---|
| a compound according to Preparation Example 1 | 5% | 10% |
| kaolin | 94% | — |
| highly dispersed silicic acid | 1% | — |
| attapulgite | — | 90% |

A solution of the active ingredient is sprayed onto the carrier, and the solvent is subsequently evaporated off in vacuo.

| (d) Dusts | (a) | (b) |
|---|---|---|
| a compound according to Preparation Example 1 | 2% | 5% |
| highly dispersed silicic acid | 1% | 5% |
| talcum | 97% | — |
| kaolin | — | 90% |

Ready-for-use dusts are obtained by homogeneously mixing the carriers with the active ingredient.

| (e) Wettable powders | (a) | (b) |
|---|---|---|
| a compound according to Preparation Example 1 | 20% | 60% |
| sodium lignosulfonate | 5% | 5% |
| sodium lauryl sulfate | — | 6% |
| octylphenol polyethylene glycol ether (7-8 moles of ethylene oxide) | — | 2% |
| highly dispersed silicic acid | 5% | 27% |
| kaolin | 70% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| a compound according to Preparation Example 1 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (g) Coated granulate | |
|---|---|
| a compound according to Preparation Example 1 | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound according to Preparation Example 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | ad 100% |

The active ingredient is intimately mixed with the adjuvants, giving a suspension concentrate from which suspensions of any desired concentration can be obtained by dilution with water.

What is claimed is:

1. A compound of formula I

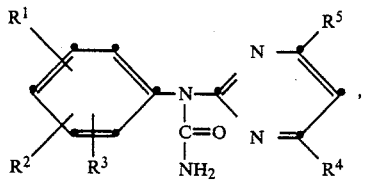

in which

R$^1$, R$^2$ and R$^3$ are each, independently of the others, hydrogen; halogen; C$_1$-C$_4$alkyl, C$_1$-C$_4$alkoxy; C$_1$-C$_4$haloalkyl; C$_1$-C$_4$haloalkoxy; C$_1$-C$_4$alkyl-S(O)$_n$-; nitro; cyano; C$_1$-C$_4$alkoxycarbonyl; di-(C$_1$-C$_4$alkylamino)-carbonyl; mono-(C$_1$-C$_4$alkylamino)carbonyl; carbamoyl; C$_1$-C$_4$haloalkyl-S(O)$_n$-; C$_1$-C$_4$alkylcarbonyl; or -PO(O-(C$_1$-C$_4$)-alkyl)$_2$;

R$^4$ is C$_1$-C$_6$alkyl; C$_1$-C$_4$alkoxy; C$_1$-C$_4$alkyl-S(O)$_n$-; C$_1$-C$_4$haloalkyl; C$_1$-C$_4$haloalkoxy; phenyl that is unsubstituted or is substituted by up to three identical or different substituents from halogen, C$_1$-C$_4$alkyl, C$_1$-C$_4$haloalkyl and C$_1$-C$_4$alkoxy; 2-furanyl; 2-thienyl; 3-thienyl; C$_3$-C$_6$cycloalkyl that is unsubstituted or is substituted by up to three identical or different C$_1$-C$_4$alkyl radicals; cyano; C$_2$-C$_4$haloalkenyl; C$_1$-C$_4$alkoxy-C$_1$-C$_4$alkyl; C$_1$-C$_4$alkoxy-C$_1$-C$_4$alkoxy; or halo-C$_1$-C$_4$alkylthio;

R$^5$ is hydrogen; C$_1$-C$_3$alkyl; C$_1$-C$_3$haloalkyl; halogen; or C$_1$-C$_3$haloalkoxy; and n is 0, 1 or 2, with the proviso that when R$^4$ and R$^5$ are both methyl, at least one of R$^1$, R$^2$ and R$^3$ is other than hydrogen and when one of the radicals R$^1$, R$^2$ and R$^3$ is nitro, that substituent may not be bonded in the 2- or 6-position of the phenyl ring, or a salt or addition compound of formula I with an acid, base or complex former.

2. A compound according to claim 1 of formula

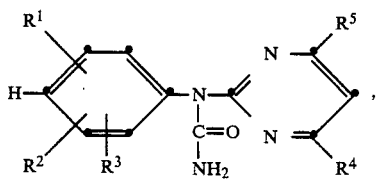

in which

R$^1$ is halogen; cyano; C$_1$-C$_4$alkoxy; C$_1$-C$_4$haloalkoxy; C$_1$-C$_4$alkyl-S(O)$_n$-; C$_1$-C$_4$alkyl; C$_1$-C$_4$haloalkyl; C$_1$-C$_4$alkoxycarbonyl; di-(C$_1$-C$_4$alkylamino)carbonyl; mono-(C$_1$-C$_4$alkylamino)carbonyl; carbamoyl; C$_1$-C$_4$haloalkyl-S(O)$_n$-; or -PO[O-(C$_1$-C$_4$)alkyl]$_2$;

R$^2$ is hydrogen; halogen; cyano; nitro; C$_1$-C$_4$alkyl; C$_1$-C$_4$alkoxy; C$_1$-C$_4$haloalkyl; C$_1$-C$_4$alkoxycarbonyl; or C$_1$-C$_4$alkylcarbonyl;

R$^3$ is hydrogen; halogen; or C$_1$-C$_4$alkyl, and n and the radicals R$^4$ and R$^5$ are as defined hereinbefore.

3. A compound according to claim 1 in which

R$^1$ is halogen; cyano; C$_1$-C$_3$alkoxy; C$_1$-C$_2$haloalkoxy; methyl-S(O)$_n$-; C$_1$-C$_3$alkyl; C$_1$-C$_2$haloalkyl; C$_1$-C$_4$alkoxycarbonyl; carbamoyl; difluoromethylthio or -PO[O-(C$_1$-C$_2$)-alkyl]$_2$;

R$^2$ is hydrogen; fluorine; chlorine; bromine; cyano; nitro; C$_1$-C$_3$alkyl; C$_1$-C$_2$haloalkyl; or C$_1$-C$_3$alkoxycarbonyl;

R$^3$ is hydrogen; chlorine; fluorine; or C$_1$-C$_3$alkyl;

R$^4$ is C$_1$-C$_5$alkyl; C$_1$-C$_4$alkoxy, C$_1$-C$_4$alkylthio; cyclopropyl; phenyl; furan-2-yl; thiophen-2-yl; cyano, C$_1$-C$_3$haloalkoxy; C$_1$-C$_2$alkoxy-C$_1$-C$_2$alkyl; C$_1$-C$_2$alkoxy-C$_1$-C$_2$alkoxy; methylsulfinyl; methylsulfonyl; or C$_2$-C$_3$haloalkenyl;

R$^5$ is C$_1$-C$_3$alkyl; fluorine; chlorine; bromine; C$_1$-C$_3$haloalkyl; or C$_1$-C$_3$haloalkoxy; and n is 0, 1 or 2.

4. A compound according to claim 1 in which

R$^1$ is fluorine, chlorine, bromine, trifluoromethyl, cyano, difluoromethoxy, trifluoromethoxy, methyl or methoxy, each bonded in the 2-position of the phenyl ring, R$^2$ and R$^3$ are each hydrogen, R$^4$ is methyl, furan-2-yl or cyclopropyl, and R$^5$ is chlorine, methyl, trifluoromethyl or chlorodifluoromethyl.

5. A compound according to claim 1 in which

R$^1$ is fluorine, chlorine, bromine, trifluoromethyl, difluoromethoxy, trifluoromethoxy, cyano or methoxy, each bonded in the 2-position of the phenyl ring, R$^2$ is fluorine or chlorine, each bonded in the 3-, 5- or 6-position of the phenyl ring, R$^4$ is methyl, furan-2-yl or cyclopropyl, and R$^5$ is chlorine, methyl, trifluoromethyl or chlorodifluoromethyl.

6. A compound according to claim 1 in which

R$^1$ is chlorine bonded in the 3-position of the phenyl ring,

R$^2$ is chlorine bonded in the 5-position of the phenyl ring,

R$^4$ is methyl, furan-2-yl or cyclopropyl, and

R$^5$ is chlorine, methyl, trifluoromethyl or chlorodifluoromethyl.

7. A herbicidal composition which comprises as active ingredient a herbicidally effective amount of a compound according to claim 1, together with an agrochemically acceptable adjuvant or carrier.

8. A plant growth-regulating composition which comprises as active ingredient a growth-regulatingly effective amount of a compound according to claim 1, together with an agrochemically acceptable adjuvant or carrier.

9. A method of controlling undesired plant growth which comprises allowing a herbicidally effective amount of a compound according to claim 1 to act on the plant to be controlled or the locus thereof.

10. A method according to claim 9 for the pre- or post-emergence control of undesired plant growth in cereals, cotton, soybeans, sunflowers, rape, maize or rice.

11. A method of influencing plant growth which comprises allowing an amount of a compound according to claim 1 that is effective in plant growth regulation, to act on the plant or the locus thereof.

12. A method according to claim 11 for regulating the growth of intersown plants in maize crops.

13. A method according to claim 11 for regulating the growth of grasses.

* * * * *